US010953055B2

(12) United States Patent
Antony

(10) Patent No.: US 10,953,055 B2
(45) Date of Patent: Mar. 23, 2021

(54) MEDICINAL COMPOSITION OF EXTRACT OF SEED OF EMBLICA OFFICINALIS AND METHOD OF PREPARING THE SAME

(71) Applicant: Benny Antony, Angamaly (IN)

(72) Inventor: Benny Antony, Angamaly (IN)

(*) Notice: Subject to any disclaimer, the term of this patent is extended or adjusted under 35 U.S.C. 154(b) by 193 days.

(21) Appl. No.: 16/297,272

(22) Filed: Mar. 8, 2019

(65) Prior Publication Data

US 2019/0201465 A1 Jul. 4, 2019

Related U.S. Application Data

(60) Division of application No. 15/429,748, filed on Feb. 10, 2017, which is a continuation-in-part of application No. 14/722,035, filed on May 26, 2015, now Pat. No. 9,775,869, which is a division of application No. 14/608,680, filed on Jan. 29, 2015, now Pat. No. 9,066,911, which is a division of application No. 14/508,998, filed on Oct. 7, 2014, now Pat. No. 8,980,340, which is a continuation of application No. PCT/IN2014/000642, filed on Oct. 7, 2014.

(30) Foreign Application Priority Data

Oct. 8, 2013 (IN) .......................... 4565/CHE/2013

(51) Int. Cl.
| | | |
|---|---|---|
| *A61K 36/00* | (2006.01) | |
| *A61K 36/185* | (2006.01) | |
| *B01D 11/02* | (2006.01) | |
| *A61Q 7/00* | (2006.01) | |
| *A61K 8/97* | (2017.01) | |
| *A61K 31/202* | (2006.01) | |
| *A61K 31/045* | (2006.01) | |
| *A61K 31/192* | (2006.01) | |
| *A61K 31/575* | (2006.01) | |
| *A61K 36/47* | (2006.01) | |
| *A61K 8/11* | (2006.01) | |
| *A61K 9/48* | (2006.01) | |
| *A61K 9/00* | (2006.01) | |
| *A61K 31/201* | (2006.01) | |

(52) U.S. Cl.
CPC .............. *A61K 36/185* (2013.01); *A61K 8/11* (2013.01); *A61K 8/97* (2013.01); *A61K 9/0053* (2013.01); *A61K 9/48* (2013.01); *A61K 31/045* (2013.01); *A61K 31/192* (2013.01); *A61K 31/201* (2013.01); *A61K 31/202* (2013.01); *A61K 31/575* (2013.01); *A61K 36/47* (2013.01); *A61Q 7/00* (2013.01); *B01D 11/02* (2013.01); *A61K 2236/15* (2013.01); *A61K 2236/33* (2013.01); *A61K 2236/333* (2013.01); *A61K 2236/39* (2013.01); *A61K 2800/92* (2013.01)

(58) Field of Classification Search
None
See application file for complete search history.

(56) References Cited

U.S. PATENT DOCUMENTS

| | | |
|---|---|---|
| 5,405,613 A | 4/1995 | Rowland |
| 6,124,268 A | 9/2000 | Ghosal |
| 6,235,721 B1 | 5/2001 | Ghosal |
| 6,290,996 B1 | 9/2001 | Ghosal |
| 6,362,167 B1 | 3/2002 | Ghosal |
| 7,001,619 B2 | 2/2006 | Johri |
| 7,780,996 B2 | 8/2010 | Antony |
| 8,158,167 B2 | 4/2012 | Antony |
| 8,455,020 B2 | 6/2013 | Antony |
| 2001/0016213 A1 | 8/2001 | Singh-Verma |
| 2003/0008048 A1 | 1/2003 | Winston |
| 2003/0194452 A1 | 10/2003 | Agarwal |
| 2005/0089590 A1 | 4/2005 | Chaudhuri |
| 2005/0281901 A1* | 12/2005 | Antony ............... A61K 36/185 424/769 |

FOREIGN PATENT DOCUMENTS

| | | |
|---|---|---|
| CA | 1334578 | 2/1995 |
| EP | 345571 A1 | 12/1989 |
| JP | 10/028549 A | 2/1998 |
| JP | 06/028091 A | 2/2006 |
| JP | 06/335708 A | 12/2006 |

(Continued)

OTHER PUBLICATIONS

Ghosal, S, Tripathi, VK and Chauhan S, Active Constituents of Emblica officinalis: Part 1—The Chemistry and Antioxidative Effects of Two New Hydrolysable Tannins, Emblicanin A and B, Indian Journal of Chemistry, 35B: 941-948 (1996).

(Continued)

*Primary Examiner* — Qiuwen Mi
(74) *Attorney, Agent, or Firm* — Jyoti C Iyer

(57) ABSTRACT

An extract of seeds of *Emblica officinalis* which has triterpenoids and hydroxycinnamic acids is provided. A blend of extracts of seeds of *Emblica officinalis* which includes an extract of seeds of *Emblica officinalis* having triterpenoids and hydroxycinnamic acids and an extract of seeds of *Emblica officinalis* having fatty acids, such as, alpha linolenic acid, linoleic acid and oleic acid is provided. Methods of preparing the extracts of seeds of *Emblica officinalis* and methods of preparing the blend of extracts of seeds of *Emblica officinalis* are provided. Methods of treatment administering the extracts of seeds of *Emblica officinalis* and methods of preparing the blend of extracts of seeds of *Emblica officinalis* are provided.

2 Claims, 15 Drawing Sheets

(56) References Cited

FOREIGN PATENT DOCUMENTS

| WO | WO 96/24327 A | 8/1996 |
|---|---|---|
| WO | WO 00/048551 A1 | 8/2000 |
| WO | WO 00/066135 A1 | 11/2000 |
| WO | WO 02/23995 A | 3/2002 |
| WO | WO 03/080090 A1 | 10/2003 |
| WO | WO 04/041231 A1 | 5/2004 |
| WO | WO 2009/060304 | 5/2009 |
| WO | WO 2011/001441 | 1/2011 |

OTHER PUBLICATIONS

Anila, L, and Vijayalakshmi, NR, Flavonoids from Emblica officinalis and Mangifera indica—Effectiveness for Dyslipedemia, Journal of Ethnopharmacology, 79: 81-87 (2002).
Brewer, HB, High-Density Lipoproteins: A New Potential Therapeutic Target for the Prevention of Cardiovascular Disease, Arterioscler. Thromb. Vase. BioL, 24: 387-391 (2004).
Brewer, HB, Increasing HDL Cholesterol Levels, N. Engl. J. Med., 350 (15): 1491-1494 (2004),Massachusetts Medical Society.
Furberg, CD, Adams, HP, Applegate, WB, Byington, RP, Espeland, MA, Hartwell, T, Hunninghake, DB, Lefkowitz, DS, Probstfield, J, and Riley, WA, Effect of Lovastatin on Early Carotid Artherosclerosis and Cardiovascular Events. Asymptomatic Carotid Artery Progression Study (ACAPS) Research Group, Circulation, 90: 1679-1687 (1994), American Heart Association.
Navab,M, Anantharamaiah, GM, Hama, S, Garber, DW, Chaddha, M, Hough,G,Lallone,R, and Fogelman,A, Oral Administration of an Apo A-1 Mimetic Peptide Synthesized From D-Amino Acids Dramatically Reduces Atherosclerosis in Mice Independent of Plasma Cholesterol, Circulation, 105: 290-292 (2002), American Heart Association.
Grundy, S, Statin Trials and Goals of Cholesterol-Lowering Therapy, Circulation, 97: 1436-1439 (1998), American Heart Association.
Ridker, PM, Clinical Application of C-Reactive Protein for Cardiovascular Disease Detection and Prevention, Circulation, 107: 363-369 (2003), American Heart Association.
Ridker, P, Cannon, CP, Morrow, D, Rifai, N, Rose, LM, McCabe, CH, Pfeffer, MA, and Braunwald, E, C-Reactive Protein Levels and Outcomes after Statin Therapy, N. Engl. J. Med., 352:20-28 (2005), Massachusetts Medical Society.
Chew, DP, Bhatt, DL, Robbins, MA, Penn, MS, Schneider, JP, Lauer, MS, Topol, EJ, and Ellis, SG, Incremental Prognostic Value of Elevated Baseline C-Reactive Protein Among Established Markers of Risk in Percutaneous Coronary Intervention, Circulation, 104: 992-997 (2001), American Heart Association.
Haffner, SM, Lehto, S, Ronnemaa, T, Pyorala, K, and Laakso, M, Mortaliy from Coronary Heart Disease in Subjects with Type 2 Diabetes and in Nondiabetic Subjects With and Without Prior Myocardial Infarction, N. Engl. J. Med., 339 (4): 229-234 (1998), Massachusetts, Medical Society.
Malmberg, K, Yusuf, S, Gerstein, HC, Brown, J, Zhao, F, Hunt, D, Piegas, L, Calvin, J, Keltai, M, Budaj, A, and for the OASIS Registry Investigators, Impact of Diabetes on Long-Term Prognosis in Patients with Unstable Angina and Non-Q-Wave Myocardial Infarction: Results of the OASIS (Organization to Assess Strategies for Ischemic Syndromes) Registry, Circulation, 102: 1014-1019 (2000), American Heart Association.
Sawin, CT, Geller, A, Wolf, PA, Belanger, AJ, Baker, E, Bachrach, P, Wilson, P, Benjamin, EJ, and D'Agostino RB, Low Serum Thyotropin Concentrations as a Risk Factor for Atrial Fibrillation in Older Persons, N. Engl. J. Med., 331: 1249-1252 (1994).
Klein, I, and Ojamaa, K, Thyroid Hormone and the Cardiovascular System, N. Engl. J. Med., 344(7): 501-509 (2001), Massachusetts Medical Society.
Pasceri, V, Willerson, JT, and Yeh, ETH, Direct Proinflammatoly Effect of G Reactive Protein on Human Endothelial Cells, Circulation, 102: 2165-2168 (2000), American Heart Association.
Sacks, FM, Pfeffer, MA, Moye, LA, Rouleau, JL, Rutherford, JD, Cole, TG, Brown, L, Warnica, JW, Arnold, JMO, Wun, C-C, Davis, BR, and Braunwald, E, for the Cholesterol and Recurrent Events Trial Investigators, The Effect of Pravastatin on Coronary Events After Myocardial Infarction in Patients with Average Cholesterol Levels, N. Engl. J. Med., 335(14): 1001-1009 (1996), Massachusetts Medical Society.
Ross, R, Atherosclerosis—An Inflammatory Disease, N. EngL J. Med., 340(2): 115-126 (1999), Massachusetts Medical Society.
Stefanick, ML, Mackey, S, Sheehan, M, Ellsworth, N, Haskell, WL, and Wood, PD, Effects of Diet aand Exercise in Men and Postmenopausal Women with Low Levels of HDL Cholesterol and High Levels of LDL Cholesterol, N. Engl. J. Med., 339(1): 12-20 (1998), Massachusetts Medical Society.
Pederson, TR, Olsson, AG, Faergeman, O, Kjekshus, J, Wedel, H, Berg, K, Wilhelmsen, L, Haghfelt, T, Thorgeirsson, G, Pyorala, K, Miettinen, T,Christophersen, B, Tobert, JA, Musliner, TA, Cook, TJ, for the Scandinavian Simvastatin Survival Study Group, Lipoprotein Changes and Reduction in the Incidence of Major Coronary Heart Disease Events in the Scandinavian Simvastatin Survival Study (4S), Circulation, 97: 1453-1460 (1998), American Heart Association.
Sacks, FM, Moye, LA, Davis, BR, Cole, TG, Rouleau, JL, Nash, DT, Pfeffer, MA, and Braunwald, E, Relationship Between Plasma LDL Concentrations During Treatment With Pravastatin and Recurrent Coronary Events in the Cholesterol and Recurrent Events Trial, Circulation, 97: 1446-1452 (1998), American Heart Association.
Ridker, PM, Rifai, N, Pfeffer, MA, Sacks, F, and Braunwald, E, Long-Term Effects of Pravastatin on Plasma Concentration of C-Reactive Protein, Circulation, 100:230-235 (1999), American Heart Association.
West of Scotland Coronary Prevention Study Group, Influence of Pravastatin and Plasma Lipids on Clinical Events in the West of Scotland Coronary Prevention Study (WOSCOPS), Circulation, 97: 1440-1445 (1998), American Heart Association.
Juonala, M, Viikari, JSA, Laitinen, T, Marniemi, J, Helenius, H, Ronnemaa, T, and Raitakari, OT, Interrelations Between Brachial Endothelial Function and Carotid Intima-Media Thickness in Young Adults: The Cardiovascular Risk in Young Finns Study, Circulation, 110: 2918-2923 (2004), American Heart Association.
Chen, Z, Fukutomi, T, Zago, AC, Ehlers, R, Detmers, PA, Wright, SD, Rogers, C, and Simon, DI, Simvastatin Reduces Neointimal Thickening in Low-Density Lipoprotein Receptor-Deficient Mice After Experimental Angioplasty Without Changing Plasma Lipids, Circulation, 106: 20-23 (2002), American Heart Association.
Sheperd, J, Cobbe, SM, Ford, I, Isles, CG, Lorimer, RA, Macfarlane, PW, McKillop, JH, and Packard, CJ, For the West of Scotland Coronary Prevention Study Group, Prevention of Coronary Heart Disease with Pravastatin in Men With Hypercholesterolmia, N. Engl. J. Med., 333(20):1301-1307 (1995), Massachusetts Medical Society.
Thakur, CP, Thakur, B, Singh, S, Sinha, PK, and, Sinha SK, The Ayurvedic medicines Haritaki, Amla and Bahira Reduce Cholesterol-Induced Atherosclerosis in Rabbits, Intl. J. Cardiology, 21: 167-175(1988).
Thakur, CP, and Mandal, K, Effect of Emblica officinalis on Cholesterol-Induced Atherosclerosis in Rabbits, Indian J Med. Res., 79: 142-146 (1984), Indian Council of Medical Research.
Sai Ram, M, Neetu, D, Deepti, P, Vandana, M, Ilavazhagan, G, Kumar, D, and Selvamurthy, W, Cytoprotective Activity of Amla (Emblica officinalis) Against Chromium (VI) Induced Oxidative Injury in Murine Macrophages, Phytother. Res., 17: 430-433 (2003), John Wiley &Sons, Ltd.
Nemmani, KVS, Jena, GB, Dey, CS, Kaul, CL, and, Ramarao, P, Cell Proliferation and Natural Killer Cell Activity by Polyherbal Formulation, Immu-21 in Mice, Indian Journal of Experimental Biology,40: 282-287 (2002).
Panda, S, and Kar, A, Fruit Extract of Emblica officinalis Ameliorates, Hyperthyroidism and Hepatic Lipid Peroxidation in Mice, Pharmazie, 58: 753-755 (2003).
Sabu, MC, and Kuttan, R, Anti-diabetic Activity of Medicinal Plants and its Relationship with their Antioxidant Property, J Ethnopharmacology, 81: 155-160 (2002).

(56) References Cited

OTHER PUBLICATIONS

Sai Ram, M, Neetu, D, Yogesh, B, Anju, B, Dipti, P, Pauline, T, Sharma, SK, Sarada, SKS, Ilavazhagan, G, Kumar, D, and Selvamurthy, W, Cytoprotective and Immunomodulation Properties of Amla (Emblica officinalis) on Lymphocytes: An In-Vitro Study, J Ethnopharmacology, 81:5-10 (2002).

Muruganandam, AV, Kumar, V, and Bhattacharya, SK, Effect of Poly Herbal Formulation, EuMil, on Chronic Stress-Induced Homeostatic Perturbations in Rats, Indian J Experimental Biology, 40:1151-1160(2002).

Babu, PS, and Prince, PSM, Antihyperglycaemic and Antioxidant Effect of Hyponidd, An Ayurvedic Herbomineral Formulation in Streptozotocin-Induced Diabetic Rats, J Pharmacy and Pharmacology, 56:1435-1442(2004).

Duan, W, Yu, Y, and Zhang, L, Antiatherogenic Effects of Phyllanthus Emblica Associated with Corilagin and its Analogue, Yakugaku Zasshi, 125(7): 587-591 (2005), The Pharmaceutical Society of Japan.

Tariq, M, Hussain, SJ, Asif, M, and Jahan, M, Protective Effect of Fruit Extracts of Emblica officinalis (Gaertn.) & Terminalia belerica (Roxb.) in Experimental Myocardial Necrosis in Rats, Indian J. exp. Biol., 15(6): 485-486 (1977).

Mishra, M, Pathak, UN, and Khan, AB, Emblica officinalis Gaetn and Serum Cholesterol Level in Experimental Rabbits, Br. J. exp. Path., 62: 526-528 (1981).

Mathur, R, Sharma, A, Dixit, VP, and Varma, M, Hypolipidaemic Effect of Fruit Juice of Emblica officinalis in Cholesterol-Fed Rabbits, J. Ethnopharmacology, 50: 61-68 (1996), Elsevier Science Ireland Ltd.

Kim, HJ, Yokozawa, T, Kim, HY, Tohda,C, Rao, TP, and Juneja, LR, Influence of Amla (Emblica officinalis Gaetn.) on Hypercholesterolemia and Lipid Peroxidation in Cholesterol-Fed Rats, J. Nutr. Sci. Vitaminol., 51: 413-418 (2005).

Bhattacharya, A, Muruganandam, AV, Kumar, V, and Bhattacharya, SK, Effect of Poly Herbal Formulation, EuMil, on Neurochemical Perturbations Induced by Chronic Stress, Indian J.exp. Biol., 40: 1 161-1163 (2002).

Bhattacharya, SK, Bhattacharya, D, and Muruganandam, AV, Effect of Emblica officinalis Tannoids on a Rat Model of Tardive Dyskinesia, Indian J. exp. Biol., 38:945-947 (2000).

One page of International Search Repot dated Dec. 1, 2003, from International Appl. No. PCT/IN03/00137.

Seven (7) pages of European Search Repot dated Jun. 18, 2009.

Nalini D and Kapoor R, Effect of Plant Fruits: Indian Gall Nut, Bedda Nut and Gooseberry—On Hypercholesterolemic Rats, Plant Foods for Human Nutrition, 53(4):343-349 (1999).

Reza MS, Khan BR, Islam B, Muhsin AUM, and Quddus R, Effects of Emblica officinalis (amlaki) and Vitamin C on Cholesterol Induced Atherosclerosis in Rabbits, Journal of Bangladesh College of Physicians and Surgeons 1994 BD, 12(1):3-7 (1994).

Rader, DJ, High-density Lipoproteins and Atherosclerosis, American Journal of Cardiology, 90(8A), 62i-70i (2002).

Protest Documents filed by Third Party on Jul. 3, 2011, thirteen (13) pages, in U.S. Appl. No. 12/805,191, filed Jul. 16, 2010.

Four (4) pages copy of International Search Report received in PCT/IN2009/000460 dated Apr. 13, 2010.

Khopde,SM, Indira Priyadarsini,K, Mohan,H, Gawandi,VB, Satav,JG, Yakhmi, JV, Banavaliker, MM, Biyani, MK, Mittal , JP, Characterizing the Antioxidant Activity of Amla(phyllanthus emblica) Extract, Current Science,vol. 81,No. 2,Jul. 25, 2001.

Majeed Muhammed, Bhat Beena, Jahav N. Atul, Srivastava S. Jyotish, Nagabhushanam Kalyanam, Ascorbic acid and Tannins from Emblica officinalis Gaertn. Fruits #A Revisit, J. Agric. Food Chem., 2009, 57 (1), 220-225.

Mishra Poonam, Lata Mahanta Charu, Comparative analysis of functional and nutritive values of Amla fruit, Seed and Seed Coat powder, American Journal of Food Technology 2014, 9(3), 151-161 (2014).

Dhar, D C, Dhar, M L, Shrivastave, DL, Chemical Examination of the Seeds of Emblica officinalis Gartn: Part I—The Fatty Oils & Its components Fatty Acids, J. Sci. Industr. Res., V. 1OB: 88-91 (1951).

Nain, Parminder, Saini Vipin, Sharma Sunil, Antidiabetic Activity of *Emblica Officinalis* Seed Extract in Streptozotocin Induced Type-2 Diabetes Mellitus in Rat, International Journal of Natural Product Science 2012; Spl Issue 1: 135.

Priya, Gupta, Parminder Nain, Jaspreet Sidana, Antimicrobial and antioxidant activity of Emblica officinalis seed extract, IJRAP, 3(4):591-596 (2012).

Protest Documents filed by Third Party on Mar. 4, 2014, nineteen (19) pages, in U.S. Appl. No. 13/886,287, filed May 3, 2013.

Antony, B, Merina, B,Sheeba,V, Mukkadan, J, Effect of standardized Amla extract on atherosclerosis and dyslipidemia, Indian J Pharm Science, 68(4), 437-441 (2006).

Antony, B, Merina,B, Kaimal,TNB, A Pilot clinical study to evaluate the effect of Emblica officinalis extract (Amlamax™) on markers of systemic inflammation and dyslipidemia, Indian Journal of Clinical Biochemistry , 23(4):378-81 (2008).

Antony, B, Merina, B, Sheeba, V ,Amlamax™ in the Management of Dyslipidemia in Humans, Indian J Pharm Sci, Indian J. Pharm. Sci., 70 (4): 504-507 (2008).

Antony, B, Merina, B,Sheeba, V ,Toxicity studies of Amlamax™— Purified standardized Extract of Emblica officinalis, Indian J . Nat. Prod., 23(2), 14-17 (2007).

Martelanc, M, Vovk, L, Simonovska, B,Separation and identification of some common isomeric plant triterpenoids by thin-layer chromatography and high-performance liquid chromatography, Journal of Chromatography A ;1216:6662-6670 (2009).

Bahri, M, Hance, P,Grec,S, Quillet,M-C, Trotin, F, Hilbert, J-L, Hendriks,T, A Novel Protocol for the Analysis of Hydroxycinnamic Acids in Leaf Tissue of Chicory (Chichorium intybus L., Asteraceae) , the scientific world journal, vol. 2012,Article 142983, 8 pages, doi:10.1100/2012/142983.

Gupta, M, Saumyakanti, S, Sohini, M and Arup,M, HPLC Profiles of Standard Phenolic Compounds Present in Medicinal Plants, International Journal of Pharmacognosy and Phytochemical Research; 4(3); 162-167(2012).

Eleven (11) pages of International Search Report received in PCT/IN2014/000642 dated Apr. 12, 2016.

Arora, A, Kumar, I, Sen, R and Singh, J, Physico-Chemical and Fatty acid Analysis from Arid Zone of Rajasthan, International Journal of Basic and Applied Chemical Sciences, 1(1): 89-92 (1982).

Yanga, CB, Zhangb, F, Denga, MC, Hea, GY,Yuec, JM and Lua, RH, A New Ellagitannin from the Fruit of Phyllanthus Emblica L, Journal of the Chinese Chemical Society, 54( 6):1615-1618 (2007).

Bhide, MM, Nitave, SA, Roles of Emblica Officinalis (Amla) in Medicine, World Journal of Pharmacy and Pharmaceutical Sciences, 3(6): 604-615(2014).

Eight (8) pages of extended European supplementary search report dated Aug. 16, 2016.

\* cited by examiner

MEDICINAL COMPOSITION OF EXTRACT OF SEED OF EMBLICA OFFICINALIS AND METHOD OF PREPARING THE SAME

FIELD

The disclosure relates a medicinal composition of the extract of seed of *Emblica officinalis*, a method of preparing a composition consisting of extract of seed of *Emblica officinalis* more particularly which has application as a nutraceutical or pharmaceutical for reducing the total cholesterol, reducing triglyceride, reducing blood glucose level, enhancing HDL-Cholesterol, increasing the HDL-Cholesterol to total cholesterol ratio, lowering LDL-Cholesterol levels, reducing the CRP level, decreasing the intima media thickening, reducing hair fall, reducing atherogenic index of plasma, increasing Apo A-I levels, decreasing Apo B levels, decreasing Apo B to Apo A-I ratio, reducing Homocysteine level, reduction in glycosylated Hb, modulating Thyroid stimulating Hormone (TSH) level, decrease in HMGCoA reductase activity, lowering total cholesterol without a change in CoQ10 levels in mammals especially human beings. The composition is effective even at lower dosage for reducing the total cholesterol, reducing triglyceride, reducing blood glucose level, enhancing HDL-Cholesterol levels, increasing the HDL-Cholesterol to total cholesterol ratio, lowering LDL-Cholesterol levels, reducing the CRP level, decreasing the intima media thickening, reducing hair fall, reducing atherogenic index of plasma, increasing Apo A-I levels, decreasing Apo B levels, decreasing Apo B to Apo A-I ratio, reducing Homocysteine level, reduction in glycosylated Hb, modulating TSH level, decrease in HMG-CoA reductase activity, lowering total cholesterol without a change in CoQ10 levels.

BACKGROUND

Amla (or Amlaka, Amlaki, or other variants) is one of the most frequently used of the Ayurvedic herbs; it is the fruit of *Phyllanthus emblica*, also called *Emblica officinalis*. The fruit is similar in appearance to the common gooseberry (*Ribes* spp., a type of currant), which is botanically unrelated to amla. However, due to the similar appearance of the fruit clusters, amla is usually called the "Indian gooseberry." The plant, a member of the Euphorbiaceae, grows to become a medium-sized tree that is found growing in the plains and sub-mountain regions all over the Indian subcontinent from 200 to nearly 2000 meters above sea level. Indian gooseberry is a wonder herbs and one of the precious gifts of nature to man. It contributes towards health and longevity.

*Emblica officinalis* (EO) enjoys a hallowed position in Ayurveda-an Indian indigenous system of medicine. According to ancient Indian mythology, it is the first tree to be created in the universe. *Emblica officinalis* fruit is one of the key constituents of the celebrated Ayurvedic preparation, Chyavanaprash, used in India for thousands of years as a vitalizing and rejuvenating health tonic. According to Ayurveda, amla balances all three doshas. While amla is unusual in that it contains five out of the six tastes recognized by Ayurved, it is most important to recognize the effects of the "virya", or potency, and "vipaka", or post-digestive effect. The fruits of EO are widely used in the Ayurveda and are believed to increase defense against diseases. I Coronary heart disease (CHD) continues to be the major cause of premature death in most developed and developing countries. A low level of HDL cholesterol is the second most important risk factor for CHD, as demonstrated in numerous clinical and epidemiological studies (Gorden, D. and Rifkind, H. M., N. Engl. J. Med., 1989, 321:1311-1315; Brewer, Jr., H. B., New Engl. J. Med, 2004, 350:1491-94) and HDL has emerged, during the past decade, as a new potential target for the treatment of cardiovascular diseases. The key role of HDL as a carrier of excess cellular cholesterol in the reverse cholesterol transport pathway is believed to provide protection against atherosclerosis. In reverse cholesterol transport, peripheral tissues, for example, vessel-wall macrophages, remove their excess cholesterol through the ATP-binding cassette transporter 1 (ABCA1) to poorly lipidated apolipoprotein A-I, forming pre-.beta.-HDL. Lecithin-cholesterol acyltransferase then esterifies free cholesterol to cholesteryl esters, converting pre-$\beta$-HDL to mature spherical $\alpha$-HDL.

HDL cholesterol is transported to the liver by two pathways: 1) it is delivered directly to the liver through interaction with the scavenger receptor, class B, type I (SR-BI); 2) cholesteryl esters in HDL are transferred by the cholesterol ester transferase protein (CETP) to very-low-density-lipoproteins (VLDL) and low-density lipoproteins (LDL) and are then returned to the liver through the LDL receptor. HDL cholesterol that is taken up by the liver is then excreted in the form of bile acids and cholesterol, completing the process of reverse cholesterol transport (Brewer, H. B. Jr., Arterioscl. Thromb. Vasc. Biol., 2004, 24:387-91). HDL is believed to have the ability to remove cholesterol from macrophages, thus preventing the formation of foam cells.

A second beneficial role of HDL in atherosclerosis is in protecting LDL from oxidation (Navab, M. et al, Circulation, 2002, 105:290-92). Unlike normal LDL, oxidized LDL is readily taken up by macrophage scavenger receptor SR-A or CD36 resulting in the formation of foam cells. Foam cells are a major component of the early atherosclerotic lesion. Further, HDL may slow the progression of lesions by selectively decreasing the production of endothelial cell-adhesion molecules that facilitate the uptake of cells into the vessel wall (Barter, P. J., et al, Curr. Opin. Lipid, 2002, 13:285-88). HDL may also prolong the half-life of prostacycline and preserve its vasodilatory effect (Mackness, M. I. et al, Atherosclerosis, 1993, 104:129-35).

Several lines of evidence support the concept that increasing the HDL level may provide protection against the development of atherosclerosis. Epidemiologic studies have shown an inverse relation between HDL cholesterol levels and the risk of cardiovascular disease. Increasing the HDL cholesterol level by 1 mg may reduce the risk of cardiovascular disease by 2 to 3 percent. Over expressing the apo-A-I gene in transgenic mice and rabbits and infusing complexes consisting of Apo A-1 and phospholipids into hyperlipidemic rabbits increase HDL cholesterol levels and decrease the development of atherosclerosis (Brewer, H B, Jr., loc. cit). In humans, infusing either of these complexes or pro-apo-A-I results in short term increase in HDL cholesterol, biliary cholesterol and fecal cholesterol loss, reinforcing the concept that elevating the HDL cholesterol level decreases the risk of cardiovascular disease.

More than 40 percent of patients with myocardial infarction have low HDL-C as a cardiac risk factor. (Genest, J. J., et al, Am. J. Cardiol., 1991, 67:1185-89). In the prospective and multicentric European Concerted Action on Thrombosis and Disabilities (ECAT) Angina Pectoris Study, Bolibar et al (Thromb. Haemost., 2000, 84:955-61) identified low HDL-C and low apoA-I as the most important biochemical risk factors for coronary events in patients with angiographically assessed CHD. By convention, the risk threshold value of HDL-C has been defined as 35 mg/dL (0.9 mmol/L) in men and 45 mg/dL (1.15 mmol/L) in women [Expert panel on detection, evaluation and treatment of high blood cholesterol in adults. The second report of the National Cholesterol Education Program (NCEP) expert panel on detection, evaluation and treatment of high blood cholesterol in adults (Adult Treatment Panel II). Circulation. 1994; 89:1329-1445)]. Because of interaction, the strength of the association between HDL-C and cardiovascular risk depends on the presence of additional risk factors. Therefore, threshold values are higher in men with diabetes mellitus or hypercholesterolemia or in the presence of multiple risk factors (von Eckardstein A, and Assmann G. Curr Opin Lipidol. 2000; 11:627-637). Low HDL-C has been identified as the most frequent familial dyslipoproteinemia in patients with premature myocardial infarction (Genest, J. J. Jr., Circulation. 1992; 85:2025-2033). Finally, in the Helsinki Heart Study (Manninen, V. et al, Circulation. 1992; 85:37-45) and the High-Density-Lipoprotein Cholesterol Intervention Trial of the Department of Veterans Affairs (VA-HIT) study (Rubins, H. B. et al, N Engl J Med. 1999; 341:410-418), increases of HDL-C on treatment with gemfibrozil were correlated with the prevention of CHD events. Thus, HDL-C has become an important component of algorithms to assess the global cardiovascular risk of patients and also a target for therapeutic intervention and for the definition of treatment goals.

Strategies to correct dyslipidemia in atherosclerosis generally involve diet and/or drugs. The threshold serum total cholesterol and LDL cholesterol concentrations above which diet and drug therapy should be initiated, as well as the goals of therapy, have been defined by the National Cholesterol Education Program (JAMA, 1993, 269:3015-23). The target serum LDL-C is <160 mg/dl (4.3 mmol/1) for patients with no risk factors or only one risk factor for CHD; <130 mg/dl (3.4 mmol/1) for patients with 2 or more risk factors and less than 100 mg/dl (2.6 mmol/1) for those with CHD. Persons with diabetes also fall into the third category. A reasonable target for triglyceride concentration is 200 mg/dl or less; higher values are associated with a doubling of the risk of cardiovascular disease when serum cholesterol concentration exceeds 240 mg/dl or when the LDL-C/HDL-C ratio exceeds 5:1.

A number of studies have shown that reducing serum LDL-C below the target levels does not necessarily result in proportional reduction in the risk of CHD [(The Scandinavian Simvastatin Survival Study Group. Randomized trial of cholesterol lowering in 4444 patients with coronary heart disease, Lancet, 1994, 344:1383-89; Shepherd, J. et al, N. Engl. J. Med., 1995, 333:1301-7; Sachs, F. M. et al, N. Engl. J. Med., 1998, 315:1001-9; Circulation, 1998, 97:1446-52; The West of Scotland Coronary Prevention Study Group, Circulation, 1998, 97:1440-45; Pederson, T. R., Circulation, 1998, 97:1453-60] because of the attenuation of the cholesterol-heart disease relation at lower serum cholesterol concentrations (Grundy, S. M., Circulation, 1998, 97:1436-39).

Dietary treatment of hyperlipidemia is a necessary foundation for drug treatment. Depending on the degree of hyperlipidemia, the Step I and Step II diets can be introduced sequentially. The Step II diet contains no more than 30% of calories from fat, less than 7% of calories from saturated fatty acids and less than 200 mg of cholesterol per day. In long term studies, the Step II diet decreased serum LDL-C concentrations 8-15% (Knopp, R. H., et al, JAMA, 1997, 278:1509-15; Walden, C. E., Arterioscl. Thromb. Vasc. Biol., 1997, 17:375-82; Denke, M. A., Arch. Intern. Med., 1995, 156:17-26). Diets more restricted in fat than the Step II diet result in little additional reduction in LDL-C, raise serum TG concentration and lower HDL-C.

The point to note, from the above, is that reducing LDL-C alone is of little value in reducing the risk of CHD. Further, diets meant for reducing LDL-C may reduce HDL-C to a similar degree (Hunninghake, D. B. et al, N. Engl. J. Med., 1993, 328:1213-19; Schaefer, E. J., et al, Arterioscl. Thromb. Vasc. Biol., 1995, 15:1079-85); Stefanick, M. L., N. Engl. J Med, 1998, 339:12-20).

Drug therapy is resorted to when the desired effects are not achieved with diets alone. Statins are the most popular among the lipid lowering drugs. These drugs lower serum LDL-C concentrations by upregulating LDL-receptor activity as well as reducing the entry of LDL into the circulation. The maximal reductions achieved with a statin ranges from 24-60%. Statins also reduce the serum TG levels; but they are often insufficient. Statins are ineffective in the treatment of patients with chylomicronemia. Adverse effects of statins include, gastrointestinal upset, muscle aches and hepatitis. Rarer problems include myopathy (muscle pain with serum creatine kinase concentrations more than 1,000 U per litre), rashes, peripheral neuropathy, insomnia, bad or vivid dreams and difficulty in sleeping or concentrating (Abramowica, M., Med Lett., 1996, 38:67-70; Vgontzas, A. N. et al, Clin. Pharmacol. Ther., 1991, 50:730-37; Roth, T. et al, Clin. Cardiol., 1992, 15:426-32; Partinen, M. et al, Am. J. Cardiol., 1994, 73:876-80). Other lipid-lowering drugs include bile acid-binding resins (e.g., cholesteramine and colestipol), nicotinic acid, and fibrates.

Drug therapy is not recommended for premenopausal women and men under 35 years of age unless they have serum LDL-C concentrations of more than 220 mg/dl (5.7 mmol/1), because their immediate risk of heart disease is low [Summary of the second report of the National Cholesterol Education Program (NCEP): expert panel on detection, evaluation and treatment of high blood cholesterol in adults, JAMA, 1993, 269:3015-23].

Thus, diets alone or in conjunction with lipid lowering drugs fail to yield the desired goal of safe lipid lowering. However, this goal is achievable with the present inventive composition containing the active principles of seed of *Emblica officinalis*. *Emblica* has been in safe use in India for thousands of years as component of Ayurvedic preparations. The composition from seed of *Emblica officinalis* offers the twin benefits of reducing the harmful LDL cholesterol and enhancing the desirable HDL cholesterol.

A number of studies have shown that *Emblica officinalis* is useful for reducing total cholesterol, reducing triglyceride, reducing LDL cholesterol and enhancing HDL cholesterol.

Ritu Mathur et al show the hypolipidaemic effect of fruit juice of *Emblica officinalis* in cholesterol fed rabbits. The juice is obtained from deseeded *Emblica officinalis*. U.S. Pat. No. 6,124,268, Ghosal discloses a natural antioxidant composition from *Emblica officinalis* using pericarp of fresh berries (*Emblica officinalis*). Biswas Gopa et al show the hypolipidemic efficacy of Amla (*Emblica officinalis*). The Amla used is dried Amla fruit juice powder. Muhammed et al evaluated the anti-hyperglycemic and lipid-lowering properties of *Emblica officinalis* powder in normal and diabetic human volunteers. Zhang et al discloses the phenolic constituents of *Emblica officinalis* juice. Chatterjee et al discloses a novel compounds with hypocholesteremic activity from crude *Embilica officinialis* (EO) fruit extracts. U.S. Pat. Nos. 7,780,996, 8,158,167 and 8,455,020 discloses the method of reducing cholesterol, method of treating dyslipidemia and method of reducing triglyceride by extract of *Emblica officinalis*.

Amla is a fruit with wide range of medicinal properties. Our effort was to find the most bioactive molecule/(s) or purified fraction having bioactivity from Amla fruit. The fleshy part (pericarp) of Amla fruit is used for human consumption whereas Amla seeds are not edible and discarded. We evaluated different Amla extracts. Extracts prepared from fresh fruit of Amla; fruit juice of whole Amla including the fleshy part and seeds of Amla; juice of fleshy part (pericarp); dried fruit; flesh of Amla fruit without seed; or Amla seed alone were evaluated for anti hyperlipidemic activity. The methanol extract of all groups showed beneficial activity, but the most unexpected and superior result was obtained from the Amla seed alone extract. Amla seed alone extract was able to significantly reduce the total cholesterol, LDL cholesterol, triglycerides, VLDL cholesterol and enhance the HDL cholesterol levels. Though Amla seed is not known to have any history of human consumption, we followed the lead with various extracts of Amla seed and found that the ethyl acetate portion of Amla seed extract is the most active. The ethyl acetate part was showing far superior activity compared to other extracts with Amla seed and also against other extracts of Amla.

In view of the above, the disclosure provides a composition and method of preparing an extract from the seed of *Emblica officinalis* unlike other references where the extract is prepared from *Emblica officinalis*, especially from its fruits which found its application for the treatment of reducing bad cholesterol, dyslipidemia and for reducing triglyceride. The disclosure provides a method of preparation of an extract of *Emblica officinalis* from the seed of *Emblica officinalis* and composition derived contain polyphenolic components and lipophilic components. The extract prepared from the seed of *Emblica officinalis* is useful for decreasing total cholesterol, decreasing triglyceride, reducing blood glucose level, enhancing HDL-Cholesterol level, increasing the HDL-Cholesterol to total cholesterol ratio, lowering LDL-Cholesterol level, reducing the CRP level, decreasing the intima media thickening, reducing atherogenic index of plasma, increasing Apo A-1 levels, decreasing Apo B levels, decreasing Apo B to Apo A-1 ratio, reducing homocysteine level, reduction in glycosylated Hb, modulating TSH level, decreasing HMGCoA reductase activity, lowering total cholesterol without changing CoQ10 levels even at a lower dosage level. The extract prepared from the seed of *Emblica officinalis* is useful for reducing hair fall in humans by applying topically or by oral administration.

SUMMARY

The disclosure provides a medicinal composition of the extracts of seed of *Emblica officinalis* (Amla seed extract). The amla seed extract composition has applications as a nutraceutical or pharmaceutical including for reducing the total cholesterol, reducing triglyceride, reducing blood glucose level, enhancing HDL-Cholesterol level, increasing the HDL-Cholesterol to total cholesterol ratio, lowering LDL-Cholesterol level, reducing the CRP level, decreasing the intima media thickening, reducing hair fall, reducing atherogenic index of plasma, increasing Apo A-I levels, decreasing Apo B levels, decreasing Apo B to Apo A-I ratio, reducing Homocysteine level, reduction in glycosylated Hb, modulating TSH level, decrease in HMGCoA reductase activity and lowering total cholesterol without a change in CoQ10 levels in mammals especially human beings.

The composition of the extracts of seed of *Emblica officinalis* is superior compared to extract from fruits of *Emblica officinalis* for indications including decreasing total cholesterol, decreasing triglyceride, decreasing blood glucose level, enhancing HDL-Cholesterol level, increasing the HDL-Cholesterol to total cholesterol ratio, lowering LDL-Cholesterol levels, decreasing CRP level, decreasing the intima media thickening, decreasing hair fall, reducing atherogenic index of plasma, increasing Apo A-I levels, decreasing Apo B levels, decreasing Apo B to Apo A-I ratio, reducing Homocysteine level, reduction in glycosylated Hb, modulating TSH level, decreasing HMGCoA reductase activity and lowering total cholesterol without changing CoQ10 levels. When same dosages of amla seed extract or amla fruit extract were administered, amla seed extract showed superior results compared to amla fruit extract.

Even if the dosage of amla fruit extract was increased compared to amla seed extract, amla seed extract administration showed superior results compared to amla fruit extract.

Some embodiments provide an amla seed blend composition (also referred to amla seed blend or Product 3). Product 3 is a blend of product 1 and product 2. Product 1 includes alpha linolenic acid, linoleic acid and oleic acid. Product 2 includes triterpenoids and hydroxycinnamic acids. In some embodiments, product 2 and product 1 are blended in a ratio of Product 2 to Product 1 ranging from about 1:60 to about 99:1.

The disclosure provides methods for preparing extracts of seed of *Emblica officinalis* or blends of extracts of seeds of *Emblica officinalis*. In some embodiments, the disclosed extracts of seed of *Emblica officinalis* or blends of extracts of seeds of *Emblica officinalis* can be used as a nutraceutical. In some embodiments, the disclosed extracts of seed of *Emblica officinalis* or blends of extracts of seeds of *Emblica officinalis* can be used as a pharmaceutical. In some embodiments, administering the disclosed extracts of seed of *Emblica officinalis* or blends of extracts of seeds of *Emblica officinalis* decreased the total cholesterol level. In some embodiments, administering the disclosed extracts of seed of *Emblica officinalis* decreased triglyceride level. In some embodiments, administering the disclosed extracts of seed of *Emblica officinalis* or blends of extracts of seeds of *Emblica officinalis* decreased blood glucose level. In some embodiments, administering the disclosed extracts of seed of *Emblica officinalis* or blends of extracts of seeds of *Emblica officinalis* increased level of HDL-Cholesterol. In some embodiments, administering the disclosed extracts of seed of *Emblica officinalis* or blends of extracts of seeds of *Emblica officinalis* increased the HDL-Cholesterol to total cholesterol ratio. In some embodiments, administering the disclosed extracts of seed of *Emblica officinalis* or blends of extracts of seeds of *Emblica officinalis* lowered LDL-Cholesterol level. In some embodiments, administering the disclosed seed extracts or blends of extracts of seeds of *Emblica officinalis* decreased the CRP level. In some embodiments, administering the disclosed extracts of seed of *Emblica officinalis* decreased thickening of the intima media thickening. In some embodiments, administering the disclosed seed extracts or blends of extracts of seed of *Emblica officinalis* decreased hair fall. In some embodiments, administering the disclosed seed extracts or blends of extracts of seed of *Emblica officinalis* decreases the atherogenic index of plasma. In some embodiments, administering the disclosed seed extracts or blends of extracts of seeds of *Emblica officinalis* increased the Apo A-I levels, decreased the Apo B levels and decreased the Apo B to Apo A-I ratio. In some embodiments, administering the disclosed seed extracts or blends of extracts of seed of *Emblica officinalis* lowered Homocysteine level and glycosylated Hb level. In some embodiments, administering the disclosed seed extracts of seed or blends of extracts of seeds of *Emblica officinalis* modulated the TSH level. In some embodiments, administering the disclosed seed extracts or blends of extracts of seed of *Emblica officinalis* decreased HMGCoA reductase activity. In some embodiments, administering the disclosed seed extracts or blends of extracts of seeds of *Emblica officinalis* lowered total cholesterol without a change in CoQ10 levels.

In some embodiments, a method of producing the extract of seed of *Emblica offcinalisis* disclosed. The method includes selecting the raw material (fresh fruit of *Emblica officinalis*), followed by deseeding the fruits of *Emblica officinalis*. Then the seeds of *Emblica officinalis* are crushed and extracted with solvents. Solvents include methanol, ethanol, isopropanol, n-butanol, methyl acetate, ethyl acetate, propyl acetate, n-butyl acetate and combinations thereof to obtain mixture. The mixture is filtered. The filtrate is concentrated to obtain a concentrated extract. The concentrated extract is dried to form a dried extract. The dried extract is macerated with water and partitioned with ethyl acetate. The ethyl acetate part and aqueous part are formed and collect the ethyl acetate part. Ethyl acetate part is concentrated and dried to form powder of ethyl acetate extract of seed of *Emblica officinalis*.

The extract of seed of *Emblica officinalis* can be prepared from fresh or dried seed of *Emblica officinalis*.

Some embodiments provide a blend of extracts of seeds of *Emblica officinalis*. The blend includes a first extract of seeds of *Emblica officinalis* having triterpenoids and hydroxycinnamic acids and a second extract of seeds of *Emblica officinalis* having fatty acids, such as, alpha linolenic acid, linoleic acid and oleic acid. Methods of preparing blend of extracts of seeds of *Emblica officinalis* are provided. Methods of treatment by administering blend of extracts of seeds of *Emblica officinalis* are provided.

The disclosure also provides a dosage form of the extract of seed of *Emblica officinalis*. The disclosure provides a dosage form of an extract of seed of *Emblica officinalis* for oral administration. Dosage forms of the extract are selected from the group consisting of a capsule, tablet, granule, sachet, powder, paste, ointment, infusion, injection, ampoule, solution, suspension, emulsion, pills, oil, cream etc.

Further a dosage form of an extract of seed of *Emblica officinalis* is disclosed for administering in a dosage ranging from about 5 mg to about 500 mg to a human subject.

BRIEF DESCRIPTION OF THE DRAWINGS

The above objectives and advantages of the disclosed teachings will become more apparent by describing in detail preferred embodiments thereof with reference to the attached drawings in which:

FIG. 14A provides a flow chart depicting a method of preparation of an extract of amla seed (first extract or sample 1). FIG. 14B provides method of preparing second extract of amla seed (product 1) and method of blending sample 1 and product 1 to form an amla seed blend composition containing enriched triterpenoids and fatty acids.

DETAILED DESCRIPTION

Figure 1:
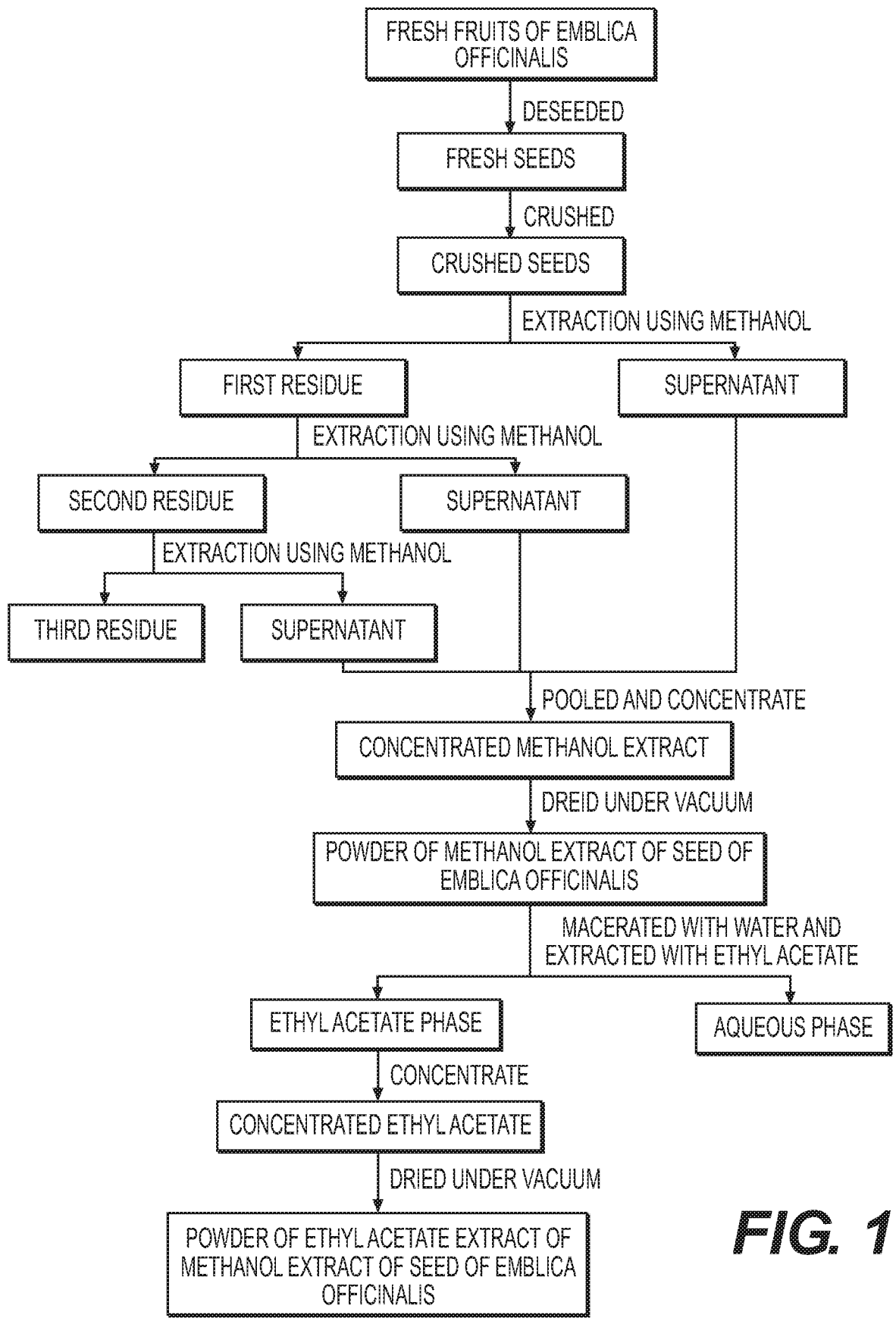
FIG. 1: Flow chart depicting a method of preparation of ethyl acetate extract of methanol extract of seed of *Emblica officinalis*.

The disclosure provides an extract of seed of *Emblica officinalis*. The disclosure also provides amla seed extract blend compositions. The disclosure relates to a medicinal composition of the extracts of seed of *Emblica officinalis* with tripertenoids up to 70%.

The disclosure provides seed extracts of *Emblica officinalis* prepared from fresh or dry seeds of *Emblica officinalis*. In some embodiments, the disclosed extracts of seed of *Emblica officinalis* can be used as a nutraceutical. In some embodiments, the disclosed extracts of seed of *Emblica officinalis* can be used as a pharmaceutical. In some embodiments, administering the disclosed extracts of seed of *Emblica officinalis* decreased the total cholesterol level. In some embodiments, administering the disclosed extracts of seed of *Emblica officinalis* decreased triglyceride level. In some embodiments, administering the disclosed extracts of seed of *Emblica officinalis* decreased blood glucose level. In some embodiments, administering the disclosed extracts of seed of *Emblica officinalis* increased level of HDL-Cholesterol. In some embodiments, administering the disclosed extracts of seed of *Emblica officinalis* increased the HDL-Cholesterol to total cholesterol ratio. In some embodiments, administering the disclosed extracts of seed of *Emblica officinalis* lowered LDL-Cholesterol level. In some embodiments, administering the disclosed extracts of seed of *Emblica officinalis* decreased the CRP level. In some embodiments, administering the disclosed extracts of seed of *Emblica officinalis* decreased thickening of the intima media thickening. In some embodiments, administering the disclosed extracts of seed of *Emblica officinalis* decreased hair fall. In some embodiments, administering the disclosed extracts of seed of *Emblica officinalis* decreases the atherogenic index of plasma. In some embodiments, administering the disclosed extracts of seed of *Emblica officinalis* increased the Apo A-1 levels, decreased the Apo B levels and decreased the Apo B to Apo A-1 ratio. In some embodiments, administering the disclosed extracts of seed of *Emblica officinalis* lowered Homocysteine level and glycosylated Hb level. In some embodiments, administering the disclosed extracts of seed of *Emblica officinalis* modulated the TSH level. In some embodiments, administering the disclosed extracts of seed of *Emblica officinalis* decreased HMGCoA reductase activity, lowering total cholesterol without a change in CoQ10 levels.

In some embodiments, administering the disclosed extracts of seed of *Emblica officinalis* promoted hair growth.

Atherogenic index of the plasma (AIP) is the logarithmically transformed ratio of molar concentrations of triglycerides (TGs) to HDL-cholesterol (log (TG/HDL [mmol]). It has recently been proposed as a marker of plasma atherogenecity because it is increased in people at higher risk for coronary heart disease and is inversely correlated with LDL particle size. The association of TGs and HDL-C in this simple ratio theoretically reflects the balance between risk and protective lipoprotein forces, and both TGs and HDL-C are widely measured and available. The strong correlation of AIP with lipoprotein particle size may explain its high predictive value. The Adult Treatment Panel III has recognized the important roles of HDL-C and TGs, calling this combination atherogenic dyslipidemia.

It has been suggest that AIP values of −0.3 to 0.1 are associated with low, 0.1 to 0.24 with medium and above 0.24 with high CV risk. [Ref: Shabnam Niroumand, Mohammad Khajedaluee, Majid Khadem-Rezaiyan, Maryam Abrishami, Mohammadreza Juya, Gholamhasan Khodaee, and Maliheh Dadgarmoghaddam. Atherogenic Index of Plasma (AIP): A marker of cardiovascular disease. Med J Islam Repub Iran. 2015; 29: 240.]. In our study, the AIP has been reduced from 0.44 to 0.09 in amla seed extract group whereas in placebo group, there was very minor increase in AIP. This indicates the benefits of amla seed extract in managing cardiovascular health and reducing the risk of future cardio vascular disease (CVD).

Apolipoprotein B (Apo B) is an important component of many lipoproteins that are involved in atherosclerosis and cardiovascular disease. Lipoproteins are the particles that transport cholesterol and triglycerides in the blood stream. Lipoproteins are comprised of proteins (apolipoproteins), phospholipids, triglycerides and cholesterol. The lipoproteins vary in the major lipoprotein present, and the relative contents of the different lipid components. Apo B is an important component of many of the most atherogenic lipoprotein particles. ApoB occurs in 2 main forms, apo B 48 and apo B 100. Apo B 48 is synthesized mainly by the small intestine. Apo B 100 is the apolipoprotein found in lipoproteins synthesized by the liver. Therefore, from the viewpoint of atherosclerosis and cardiovascular risk, apoB100 is the important one. Apo B 48 is primarily found in chylomicrons. Apo B 100 is found in chylomicrons, VLDL, IDL and LDL. All these particles are atherogenic. Each of these particles contains a single apoB molecule. Therefore, measurements of apo B represent the total burden of the main lipoprotein particles involved in the atherosclerotic process. Usually, 85-90 percent of apo B represent LDL particles. Thus, apoB reflects particle concentration, similar to LDL. Apo B containing lipoproteins are the ones that are most likely to enter the wall of the arteries. They are capable of trafficking cholesterol into the artery wall, and if present in increased numbers they may be the main initiating factor in atherosclerosis. Several studies have shown that apoB may be a better predictor of cardiovascular disease risk than LDL-C. The reference range of apoB levels in adults is less than 130 mg/dL (1.3 g/L). Apo B levels are higher in males than in females and tend to increase with age.

In our study, the apo B decreased from 1.52 g/L to 1.11 g/L in amla seed extract group whereas in placebo group there was no change. This indicates the benefits of amla seed extract in reducing the risk of CVD.

Apo A-1 is a protein that has a specific role in the metabolism of lipids and is the main protein component in HDL, the "good cholesterol". HDL removes excess cholesterol from cells and takes it to the liver for recycling or disposal. Levels of Apo A-1 tend to rise and fall with HDL levels, and deficiencies in Apo A-1 correlate with an increased risk of developing CVD. Low levels of Apo A-1 are associated with low levels of HDL and impaired clearance of excess cholesterol from the body. There are some genetic disorders that lead to deficiencies in Apo A-1 (and therefore to low levels of HDL). People with these disorders tend to have abnormal lipid levels. Apolipoprotein A-1 (Apo-A1) is a structural and functional protein that constitutes approximately 70% of the protein in high density lipoprotein (HDL). The reference range of Apo-A1 varies by sex, as follows: Men: Greater than 120 mg/dL (1.2 g/L) and Women: Greater than 140 mg/dL (1.4 g/L). These levels decrease with age.

In our study, the Apo A-1 increased from 1.05 g/L to 1.32 g/L in amla seed extract group whereas in placebo group there was no change. This indicates the benefits of amla seed extract in reducing the risk of CVD.

Low levels of Apo A-1, along with high concentrations of apo B, are associated with an increased risk of cardiovascular disease. One study found that the apo B/Apo A1 ratio is more effective at predicting heart attack risk, than either the apo B or apoA1 measure alone. The normal values are 0.5 to 1.0.

In our study, the ratio of Apo B to Apo A-1 has been decreased from 1.45 g/L to 0.84 g/L in amla seed extract group whereas in placebo group there was no change. This indicates the benefits of amla seed extract in reducing the risk of CVD. [Ref: Min Lu, Qun Lu, Yong Zhang, and Gang Tian. Apo B/Apo A1 is an effective predictor of coronary heart disease risk in overweight and obesity. J Biomed Res. 2011; 25(4): 266-273.]

Homocysteine is an amino acid and breakdown product of protein metabolism that, when present in high concentrations, has been linked to an increased risk of heart attacks and strokes. Amino acids are the building blocks of proteins. When proteins break down, elevated levels of amino acids like homocysteine may be found in the bloodstream. Having elevated levels of homocysteine in the blood (hyperhomocysteinemia) is associated with atherosclerosis and blood clots. Elevated homocysteine levels are thought to contribute to plaque formation by damaging arterial walls. High levels may also act on blood platelets and increase the risks of clot formation. Foods containing methionine are transformed into homocysteine in the bloodstream. Homocysteine is converted in the body to cysteine, with vitamin B6 facilitating this reaction. Homocysteine can also be recycled back into methionine using vitamin B12-related enzymes. If homocysteine cannot be converted into cysteine or returned to the methionine form, levels of homocysteine in the body increase. Elevated homocysteine levels have been associated with heart attack, stroke, blood clot formation, and perhaps the development of Alzheimer's disease.

Homocysteine levels are typically higher in men than women, and increase with age. Common levels are in range of 10-15 µmol/L in plasma. In our study, the homocystein level has been reduced from 23.58 to 15.61 µmol/L in amla seed extract group whereas in placebo group, there was no change as compared to baseline value. This indicates the benefits of amla seed extract in managing cardiovascular health and preventing the risk of stroke, heart attack and other related risks. [Ref: Paul Ganguly and Sreyoshi Fatima Alam. Role of homocysteine in the development of cardiovascular disease. Nutr J. 2015; 14: 6.]

Coenzyme Q10 is the coenzyme for mitochondrial enzyme complexes involved in oxidative phosphorylation in the production of ATP. That bio energetic effect of CoQ10 is believed to be of fundamental importance in its clinical application, particularly as it relates to cells with exceedingly high metabolic demands such as cardiac myocytes. The second fundamental property of CoQ10 involves its antioxidant (free radical scavenging) functions. CoQ10 is the only known naturally occurring lipid soluble antioxidant for which the body has enzyme systems capable of regenerating the active reduced ubiquinol form. CoQ10 is carried in the blood with low density lipoprotein and serves to diminish the oxidation of LDL cholesterol in settings of oxidative stress. Other more recently discovered aspects of CoQ10 function include its involvement in extramitochondrial electron transfer, e.g. plasma membrane oxidoreductase activity, involvement in cytosolic glycolysis, and potential activity in both Golgi apparatus and lysosomes. CoQ10 also plays a role in improvement in membrane fluidity. CoQ10 is essential for all cellular ATP production and is of particular importance in heart muscle function given that tissue's extreme energy requirements. A deficiency of CoQ10 in the blood and the heart muscle has been documented in congestive heart failure. Primary and secondary deficiencies of CoQ10 result in a number of neurologic and myopathic syndromes. [Ref: Langsjoen P. H. and Langsjoen A. M. Overview of the Use of CoQ10 in Cardiovascular Disease. BioFactors 1999; 9(2-4): 273-284].

HMG-CoA reductase (3-hydroxy-3-methyl-glutaryl-coenzyme A reductase) is the rate-controlling enzyme of the mevalonate pathway, the metabolic pathway that produces cholesterol and other isoprenoids. Normally in mammalian cells this enzyme is suppressed by cholesterol derived from the internalization and degradation of low density lipoprotein (LDL) via the LDL receptor as well as oxidized species of cholesterol. Competitive inhibitors of the reductase induce the expression of LDL receptors in the liver, which in turn increases the catabolism of plasma LDL and lowers the plasma concentration of cholesterol, an important determinant of atherosclerosis. This enzyme is thus the target of the widely available cholesterol-lowering drugs known collectively as the statins. [Ref: DeBose-Boyd R A. Feedback Regulation of Cholesterol Synthesis: Sterol-Accelerated Ubiquitination and Degradation of HMG CoA Reductase. Cell Res. 2008; 18(6): 609-621.]

In the present study, amla seed extract has reduced the level of HMGCoA reductase, which is beneficial to reduce the cholesterol level. The synthetic HMGCoA reductase inhibitors (statins) also decrease the cholesterol level but at the same time, CoQ10 level also decreases which is responsible for severe side effect. Amla seed extract reduced the HMGCoA level in dyslipidemia patients without affecting the CoQ10 level after treatment with Amla seed extract or placebo. This is very important finding and unlike statins keeps Amla seed extract free from severe side effects associated with CoQ10 deficiency. In this study, highly significant reduction in HMGCoA reductase enzyme by Amla seed extract explains its mechanism of decreasing blood cholesterol and management of cardio vascular health. At the same time, no change in CoQ10 level puts an advantage of Amla seed extract over statin therapy and makes it better choice than statins for treatment of dyslipidemia.

In an in vitro assay on HMG-CoA reductase inhibition, the amla seed extract inhibited the enzyme more than 98% at 200 µg/mL concentration and IC50 value was calculated as 31.07. Low value of IC50 indicates strong inhibition of HMGCoA reductase enzyme and thus better for reduction of cholesterol. The IC50 for standard lovastatin was recorded as 29.7 which is very near to the IC50 of amla seed extract. Thus amla seed extract is almost equally effective as standard lovastatin in the inhibiting of HMGCoA reductase in vitro. The water extract of dried amla seed was less effective than amla seed extract and IC50 was found as 142.7. [Ref: Holdgate, G. A., et. al., Molecular mechanism for inhibition of 3-hydroxy-3-methylglutaryl CoA (HMG-CoA) reductase by rosuvastatin. Biochem. Soc. Trans., 31, 528-531 (2003)].

Glycated hemoglobin (HbA1c) is a form of hemoglobin that is measured primarily to identify the three month average plasma glucose concentration. It is formed in a non-enzymatic glycation pathway by hemoglobin's exposure to plasma glucose. HbA1c is a measure of the beta-N-1-deoxy fructosyl component of hemoglobin. Normal levels of glucose produce a normal amount of glycated hemoglobin. As the average amount of plasma glucose increases, the fraction of glycated hemoglobin increases in a predictable way. This serves as a marker for average blood glucose levels over the previous three months before the measurement as this is the lifespan of red blood cells. Excessive formation of early glycation products may adversely affect several functions of blood vessels, lipid metabolism and prone to develop diabetic complications. In blood vessels, uptake of LDL may be enhanced; resulting in atherogenesis and also increases the free radical mediated damage. These reversible biochemical abnormalities probably play a role in the pathogenesis of the early functional changes in the diabetic microvasculature. Higher amounts of HbA1c in diabetic patients, indicating poorer control of blood glucose levels, have been associated with diabetic complications like; cardiovascular disease, nephropathy, and retinopathy.

HbA1c level below 5.7 percent is considered normal whereas between 5.7 and 6.4 percent signals pre-diabetes. In our study, the level of HbA1c has been reduced from 6.7% to 5.59% in amla seed extract group whereas in placebo group, there was no change in HbA1c level. This indicates the benefits of amla seed extract in managing the blood sugar level and preventing diabetes.[Ref: Babbar A, Kaul N, Gupta S. Clinical significance of glycosylated haemoglobin (HbA1C) over fasting blood sugar for monitoring metabolic control in diabetic patients with or without complications. J Indian Med Assoc. 1996; 94(11):414-6.]

Thyroid function regulates a wide array of metabolic parameters. Thyroid function significantly affects lipoprotein metabolism as well as some cardiovascular disease (CVD) risk factors, thus influencing overall CVD risk.

Thyroid hormones induce the 3-hydroxy-3-methylglutaryl-coenzyme A (HMG-CoA) reductase, which is the first step in cholesterol biosynthesis. Moreover, triiodothyronine (T3) upregulates LDL receptors by controlling the LDL receptor gene activation. This T3-mediated gene activation is done by the direct binding of T3 to specific thyroid hormone responsive elements (TREs). Furthermore, T3 controls the sterol regulatory element-binding protein-2 (SREBP-2), which in turn regulates LDL receptor's gene expression. T3 has also been associated with protecting LDL from oxidation. Thyroid hormones can influence HDL metabolism by increasing cholesteryl ester transfer protein (CETP) activity, which exchanges cholesteryl esters from HDL2 to the very low density lipoproteins (VLDL) and TGs to the opposite direction. In addition, thyroid hormones stimulate the lipoprotein lipase (LPL), which catabolizes the TG-rich lipoproteins, and the hepatic lipase (HL), which hydrolyzes HDL2 to HDL3 and contributes to the conversion of intermediate-density lipoproteins (IDL) to LDL and in turn LDL to small dense LDL.

Normal TSH level ranges from 0.4 to 4 µIU/ml. In our study, the amla seed extract has increased the TSH level from 2.43 to 3.19, thus increasing the lipoprotein lipase which reflects in decreasing the TGs. In placebo group there was slight decrease in TSH level. [Ref: Klemperer J D. Thyroid hormone and cardiac surgery. Thyroid. 2002; 12(6): 517-21.]

The composition of the extracts of seed of *Emblica officinalis* is superior compared to extract from fruits of *Emblica officinalis* for reducing the total cholesterol, reducing triglyceride, reducing blood glucose level, enhancing HDL-Cholesterol level, increasing the HDL-Cholesterol to total cholesterol ratio, lowering LDL-Cholesterol levels, reducing the CRP level, decreasing the intima media thickening, reducing atherogenic index of plasma, increasing Apo A-1 levels, decreasing Apo B levels, decreasing Apo B to Apo A-1 ratio, reducing Homocysteine level, reduction in glycosylated Hb, modulating TSH level, decreasing HMG-CoA reductase activity, lowering total cholesterol without changing CoQ10 levels, reducing hair fall and promoting hair growth.

When same dosages of amla seed extract or amla fruit extract were administered, amla seed extract administration showed superior results compared to administering amla fruit extract.

Even if the dosage of amla fruit extract was increased compared to amla seed extract, amla seed extract administration showed superior results compared to amla fruit extract.

Some embodiments provide an extract of seeds of *Emblica officinalis*. The extract of *Emblica officinalis* includes triterpenoids, hydroxycinnamic acids, fatty acids and polyphenols. The triterpenoids includes beta sito sterol, beta amyrin and lupeol. The hydroxycinnamic acids include ferulic acid and p coumaric acid. The fatty acids include alpha linolenic acid, linoleic acid, oleic acid, stearic acid and palmitic acid. In some embodiments, the extract prepared from seed of *Emblica officinalis* includes polyphenolic components and lipophilic components.

In some embodiments of the extract of seeds of *Emblica officinalis*, triterpenoids ranges from about 0.5 to about 20% of the extract. In some embodiments, the extract of seeds of *Emblica officinalis* has about 0.5% to about of 5% of hydroxy cinnamic acids. In some embodiments, the extract of seeds of *Emblica officinalis* has about 25% to about 50% of fatty acids. In some embodiments, the extract of seeds of *Emblica officinalis* has about 10% to about 95% of polyphenols. In some embodiments, the extract of seeds of *Emblica officinalis* has about 10% to about 20% of polyphenols. Some embodiments provide an extract of seeds of *Emblica officinalis* having about 0.5 to about 20% triterpenoids, about 25% to about 50% fatty acids and about 10% to about 20% polyphenol. The triterpenoids include beta sito sterol, beta amyrin and lupeol, the hydroxycinnamic acids include ferulic acid and p-coumaric acid, the fatty acids include alpha linolenic acid, linoleic acid, oleic acid, stearic acid and palmitic acid, and about 2.5% to about 50% of the polyphenols are hydroxycinnamic acids.

In some embodiments, the extract of seeds of *Emblica officinalis* has about 9.5% triterpenoids. In some embodiments, the extract of seeds of *Emblica officinalis* has about 4.3% of hydroxycinnamic acids. In some embodiments, the extract of seeds of *Emblica officinalis* has about 41.8% fatty acids. In some embodiments, the extract of seeds of *Emblica officinalis* has about 15% polyphenols.

In some embodiments of the extract of seeds of *Emblica officinalis*, triterpenoids enriched up to 70% of the extract. In some embodiments, the extract of seeds of *Emblica officinalis* has about 20% to about of 70% of triterpenoids. In some embodiments, the extract of seeds of *Emblica officinalis* has about 10% to about of 40% of hydroxy cinnamic acids. In some embodiments, the extract of seeds of *Emblica officinalis* has about 30% to about 60% of polyphenols.

In some embodiments, the extract of seeds of *Emblica officinalis* has about 63.5% triterpenoids. In some embodiments, the extract of seeds of *Emblica officinalis* has about 27% of hydroxycinnamic acids.

Some embodiments provide a seed extract product having the extract of seed of *Emblica officinalis*. The seed extract product includes fillers such as lactose, spray dried lactose, starch, dibasic calcium phosphate, tribasic calcium phosphate, microcrystalline cellulose, hydroxy propyl methyl cellulose, or calcium carbonate.

The disclosure relates to a composition having polyphenolic and lipophilic components obtained from extract of seed of *Emblica officinalis* wherein the polyphenolic components present in the extract of seed of *Emblica officinalis* ranges from 10% to 95%. Similarly the extract of seed of *Emblica officinalis* contains lipophilic components ranges from 5% and above.

Some embodiments provide a method of preparing an extract of seeds of *Emblica officinalis*. The method includes deseeding fresh fruits of *Emblica officinalis* to obtain seeds of *Emblica officinalis*. The seeds are crushed. The crushed seeds are extracted with 95% methanol to obtain a residue and a supernatant. The supernatant is concentrated to obtain a concentrated methanol extract. The concentrated methanol extract is dried to obtain a powder of methanol extract of seeds of *Emblica officinalis*. The method further includes macerating the powder of methanol extract of seeds of *Emblica officinalis* in water to obtain a liquid. The liquid is extracted with ethyl acetate to obtain an ethyl acetate phase. The ethyl acetate phase is concentrated to obtain a concentrated ethyl acetate phase. The concentrated ethyl acetate phase is dried to obtain a powder of ethyl acetate extract of methanol extract of seed of *Emblica officinalis*.

Powder of ethyl acetate extract of methanol extract of seed of *Emblica officinalis* is blended with microcrystalline cellulose to obtain a blend of powder of ethyl acetate extract of methanol extract of seed of *Emblica officinalis* and microcrystalline cellulose.

Some embodiments provide a method of preparing an extract of seeds of *Emblica officinalis*. The method includes deseeding fresh fruits of *Emblica officinalis* to obtain seeds of *Emblica officinalis*. The seeds are crushed. The crushed seeds are extracted with ethyl acetate to obtain a supernatant. The supernatant is concentrated to obtain a concentrated ethyl acetate extract. The concentrated ethyl acetate extract is dried to obtain a powder of ethyl acetate extract of seeds of *Emblica officinalis*.

In some embodiments, the fresh fruit of *Emblica officinalis* is cleaned and deseeded. Seeds are crushed and extracted for about 1 hr using methanol in an extractor with reflux condenser to obtain residue and supernatant. The residue and supernatant is separated by draining out the supernatant from the extractor bottom through the filter cloth. The resultant supernatant is concentrated in an Agitated thin film evaporator (ATFE) at a temperature of 65° C. to form concentrated extract. Later the concentrated extract is dried under vacuum at above 500 mm of mercury to form powder of methanol extract of seed of *Emblica Officinalis*.

The powder of methanol extract of seed of *Emblica officinalis* is macerated with water and partitioned with ethyl acetate. Collect the ethyl acetate part. Concentrate the ethyl acetate part in an Agitated thin film evaporator and dried under vacuum at above 500 mm of mercury to form powder of ethyl acetate extract of methanol extract of seed of *Emblica officinalis*. Method of preparing the extract is provided in FIG. 1.

Figure 2:
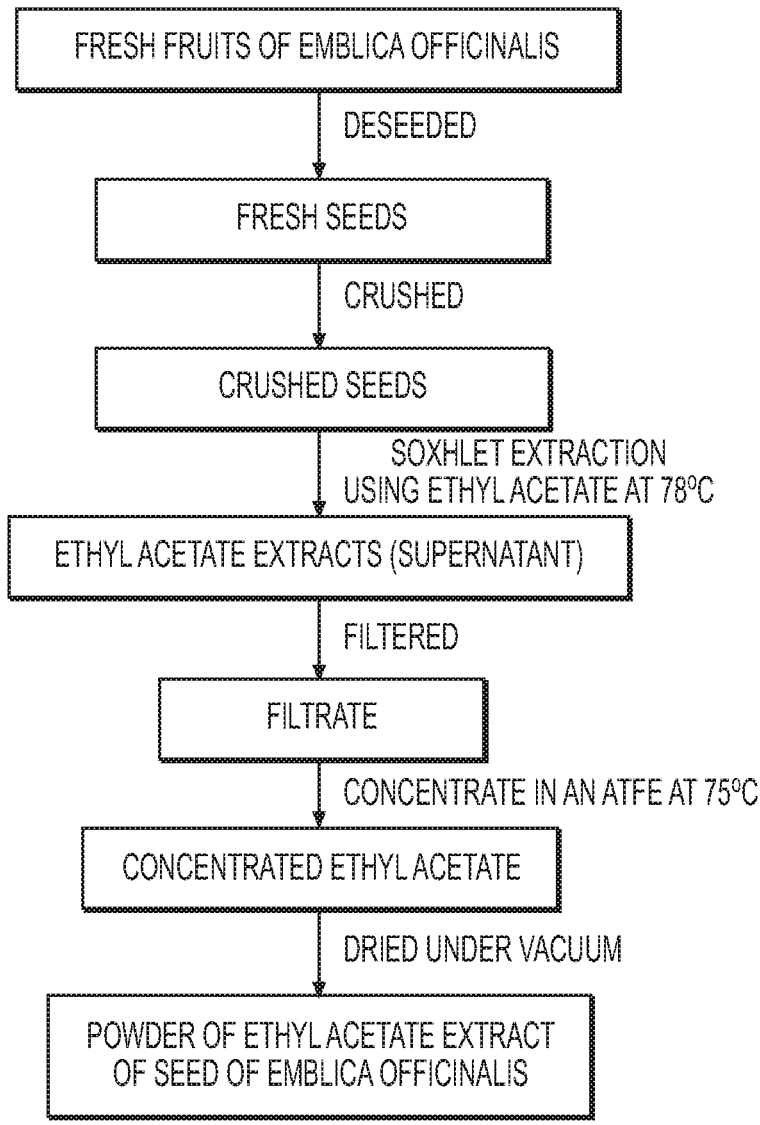
FIG. 2: Flow chart depicting a method of preparation of ethyl acetate extract of seed of *Emblica officinalis*.

In one embodiment fresh fruit of *Emblica officinalis* is cleaned and deseeded. Seeds are crushed and extracted for 5 hrs using ethyl acetate at 78° C. in a Soxhlet extractor and then filtered. The resultant extract is concentrated in an Agitated thin film evaporator (ATFE) at a temperature of 75° C. to form concentrated extract. Later the concentrated extract is dried under vacuum at above 500 mm of mercury to form powder of ethyl acetate extract of seed of *Emblica officinalis*. Method of preparing the extract is provided in FIG. 2.

Figure 3:
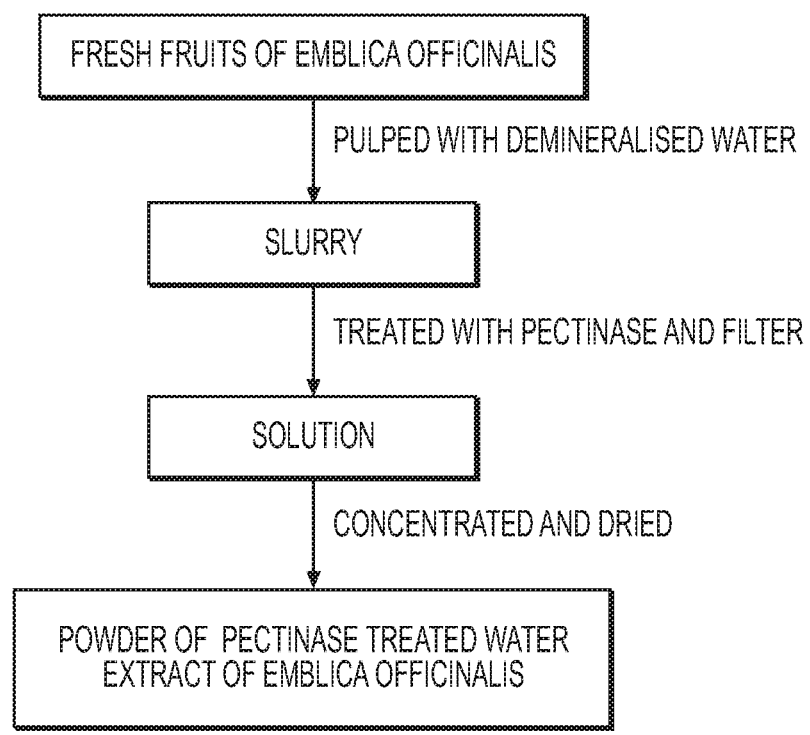
FIG. 3: Flow chart depicting a method of preparation of pectinase treated water extract of fruits of *Emblica officinalis*.

In another embodiment the method of manufacture of a powder of a pectinase treated water extract of fruits of *Emblica officinalis* is by pulping fruits of *Emblica officinalis* with demineralized water to create slurry. The slurry is treated with pectinase and then filtered to obtain a solution. The solution is concentrated and dried under vacuum. Dried product is pulverized and sieved through 30 mesh to obtain a powder of the pectinase treated water extract of fruits of *Emblica officinalis*. Method of preparing the extract is provided in FIG. 3.

Figure 4:
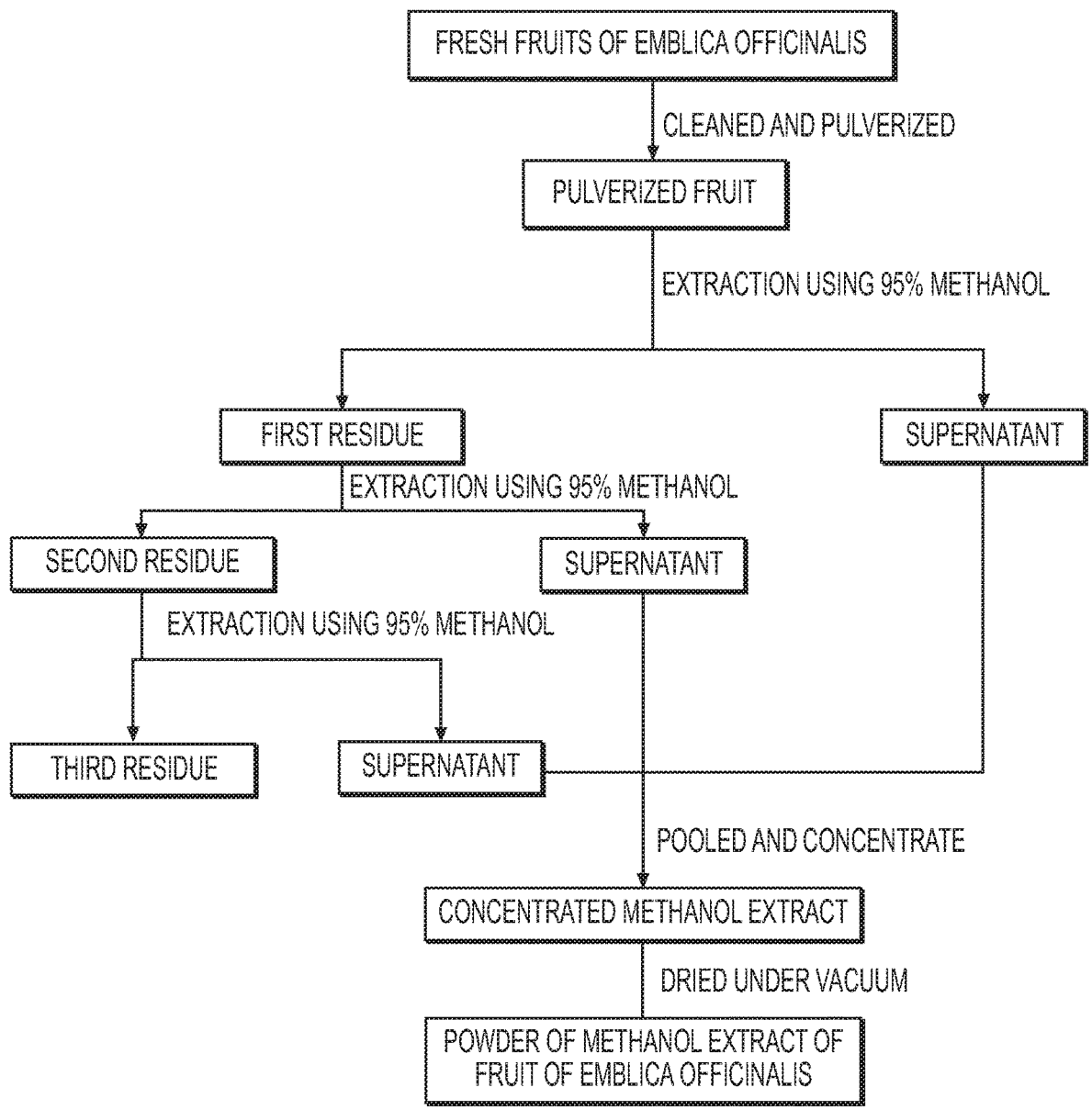
FIG. 4: Flow chart depicting a method of preparation of alcoholic extract of fruits of *Emblica officinalis*.

Some embodiments disclose a method of preparing a powder of an alcoholic extract of fruits of *Emblica officinalis*. Fresh fruits of *Emblica officinalis* are pulverized and extracted for about 1 hr using 95% methanol in an extractor with reflux condenser to obtain residue and supernatant. The residue and supernatant is separated by draining out the supernatant from the extractor bottom through the filter cloth. The resultant supernatant is concentrated in an Agitated thin film evaporator (ATFE) at a temperature of 65° C. to form concentrated extract. Later the concentrated extract is dried under vacuum at above 500 mm of mercury to form powder of methanol extract of fruit of *Emblica Officinalis*. Method of preparing the extract is provided in FIG. 4.

Figure 5:
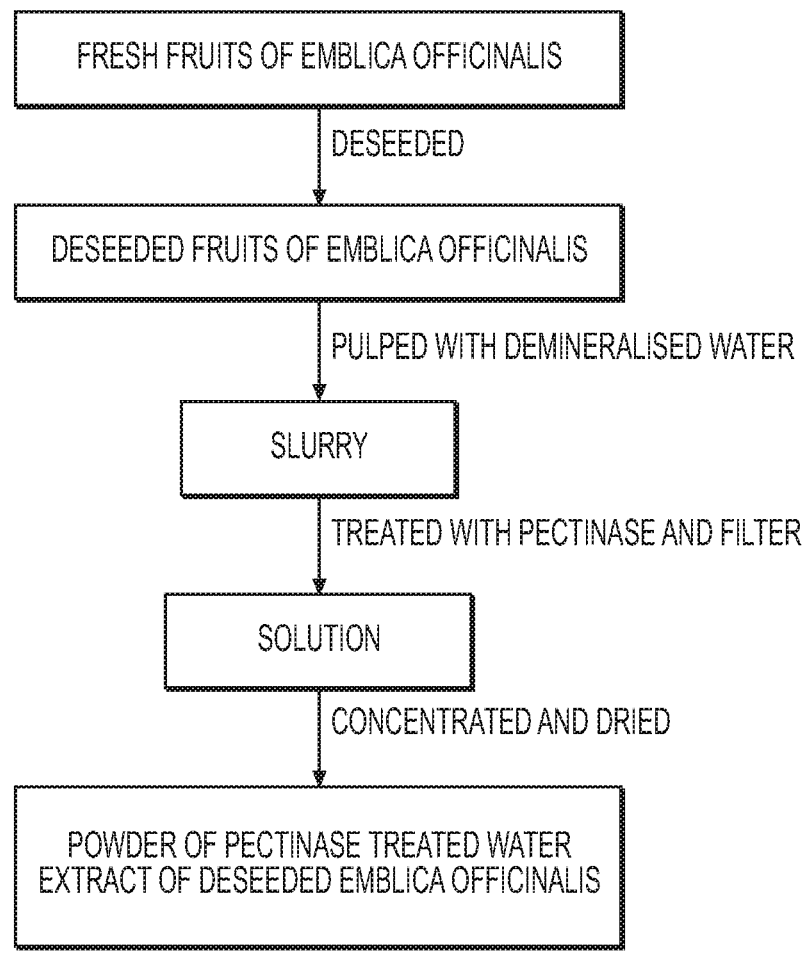
FIG. 5: Flow chart depicting a method of preparation of pectinase treated water extract of fruits of *Emblica officinalis* without seed.

In some embodiments, a method of manufacture of a powder of a pectinase treated water extract of fruits of deseeded *Emblica officinalis* is disclosed. Fruit of deseeded *Emblica officinalis* is made into a pulp along with demineralized water to create slurry. The slurry is treated with pectinase and then filtered to obtain a solution. The solution is concentrated and dried under vacuum. The dried material is pulverized and sieved through 30 mesh to obtain a powder of the pectinase treated water extract of fruits of deseeded *Emblica officinalis*. Method of preparing the extract is provided in FIG. 5.

Figure 6:
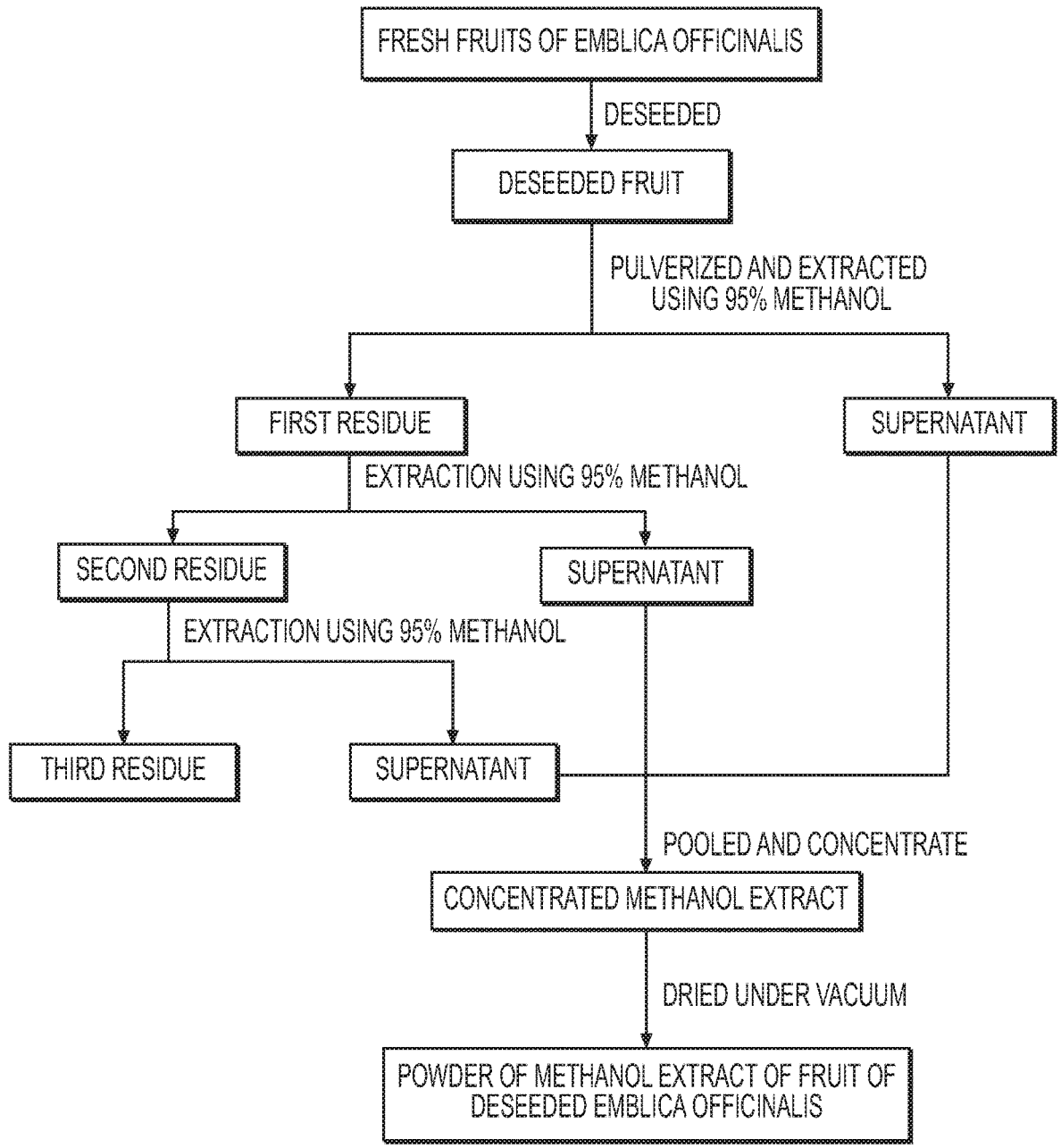
FIG. 6: Flow chart depicting a method of preparation of alcoholic extract of fruits of *Emblica officinalis* without seed.

In another embodiment, a method of preparing a powder of an alcoholic extract of fruits of deseeded *Emblica officinalis* is disclosed. Fresh fruits of *Emblica officinalis* are deseeded and deseeded fruits are pulverized and extracted for about 1 hr using 95% methanol in an extractor with reflux condenser to obtain residue and supernatant. The residue and supernatant is separated by draining out the supernatant from the extractor bottom through the filter cloth. The resultant supernatant is concentrated in an Agitated thin film evaporator (ATFE) at a temperature of 65° C. to form concentrated extract. Later the concentrated extract is dried under vacuum at above 500 mm of mercury to form powder of methanol extract of fruit of deseeded *Emblica Officinalis*. Method of preparing the extract is provided in FIG. 6.

Some embodiments provide a composition having the extract of seeds of *Emblica officinalis*. Some embodiments provide a method of treatment by administering to a human subject about 5 mg to about 500 mg of the extract of seeds of *Emblica officinalis*. Some embodiments provide a dosage form having the extract of seeds of *Emblica officinalis*. The dosage form includes a dosage of the extract of seeds of *Emblica officinalis* ranging from about 5 mg to about 500 mg. Some embodiments of the method administer a dose of about 5 mg to about 500 mg per day to a human. Some embodiments administer a dose of about 5 mg to about 500 mg two or three times per day to a human. In some embodiments, the extract of seed of *Emblica officinalis* is administered in a dosage of 5 mg to 100 mg in humans. The dosage form is administered in single or multiple doses per day. Some embodiments provide a dosage form such as a capsule, tablet, granule, sachet, powder, paste, ointment, infusion, injection, ampoule, solution, suspension, emulsion, pills, oil, or, cream.

Some embodiments provide a method of reducing total cholesterol by administering an extract of seeds of *Emblica officinalis*. Some embodiments provide a method of reducing triglyceride by administering an extract of seeds of *Emblica officinalis*. Some embodiments provide a method of reducing blood glucose level by administering an extract of seeds of *Emblica officinalis*. Some embodiments provide a method of enhancing HDL-Cholesterol by administering an extract of seeds of *Emblica officinalis*. Some embodiments provide a method of increasing a ratio of HDL cholesterol to total cholesterol by administering an extract of seeds of *Emblica officinalis*. Some embodiments provide a method of lowering LDL-Cholesterol levels by administering an extract of seeds of *Emblica officinalis*. Some embodiments provide a method of lowering VLDL by administering an extract of seeds of *Emblica officinalis*. Some embodiments provide a method of reducing CRP level by administering an extract of seeds of *Emblica officinalis*. Some embodiments provide a method of decreasing the intima media thickening by administering an extract of seeds of *Emblica officinalis*. Some embodiments provide a method of reducing hair fall by administering an extract of seeds of *Emblica officinalis*. Some embodiments provide a method of reducing atherogenic index of plasma by administering an extract of seeds of *Emblica officinalis*. Some embodiments provide a method of increasing Apo A-1 levels, method of decreasing Apo B levels and method of decreasing the Apo B to Apo A-1 ratio by administering an extract of seeds of *Emblica officinalis*. Some embodiments provide a method of lowering homocysteine level and glycosylated Hb level by administering an extract of seeds of *Emblica officinalis*. Some embodiments provide a method to modulate the TSH level by administering an extract of seeds of *Emblica officinalis*. Some embodiments provide a method of lowering HMGCoA reductase activity by administering an extract of seeds of *Emblica officinalis*. Some embodiments provide a method of lowering total cholesterol without changing CoQ10 levels by administering an extract of seeds of *Emblica officinalis*. Some embodiments provide a method of decreasing risk for coronary heart disease by administering an extract of seeds of *Emblica officinalis*. Some embodiments provide a method of decreasing atherogenic dyslipidemia by administering an extract of seeds of *Emblica officinalis*.

Some embodiments provide an amla seed blend composition. Some embodiments of the amla seed blend composition are referred to as product 3. The amla seed blend composition is a blend of varying ratios of product 1 and product 2. Product 1 includes alpha linolenic acid, linoleic acid and oleic acid. Product 2 includes triterpenoids and hydroxycinnamic acids. Product 2 includes triterpenoids and polyphenols. In some embodiments, product 2 and product 1 are blended in a ratio of product 2 to product 1 ranging from about 1:1 to about 99:1. In some embodiments, product 2 and product 1 are blended in a ratio of product 2 to product 1 ranging from about 1:60 to about 99:1. In some embodiments, product 2 and product 1 are blended in a ratio of product 2 to product 1 ranging from about 1:1 to about 1:10. In some embodiments, product 2 and product 1 are blended in a ratio of product 2 to product 1 of about 2:3. In some embodiments, product 2 and product 1 are blended in a ratio of product 2 to product 1 of about 1:2. In some embodiments, product 2 and product 1 are blended in a ratio of product 2 to product 1 of about 1:1. In some embodiments, product 2 and product 1 are blended in a ratio of product 2 to product 1 of about 3:2. In some embodiments, product 2 and product 1 are blended in a ratio of product 2 to product 1 of about 10:1 or 90:9. In some embodiments, product 2 and product 1 are blended in a ratio of product 2 to product 1 of about 95:5 or 19:1. In some embodiments, product 2 and product 1 are blended in a ratio of product 2 to product 1 of about 3:1 or 75:25. In some embodiments, product 2 and product 1 are blended in a ratio of product 2 to product 1 of about 1:5. In some embodiments, product 2 and product 1 are blended in a ratio of product 2 to product 1 of about 1:10. In some embodiments, product 2 and product 1 are blended in a ratio of product 2 to product 1 of about 1:3.

In some embodiments, the blending of product 2 and product 1 provides an amla seed blend composition having about 6% to about 50% of triterpenoids. The triterpenoids include among others beta-sitosterol, beta amyrin and lupeol. In some embodiments, the blending of product 2 and product 1 provides an amla seed product having about 2% to about 20% of hydroxycinnamic acids. The hydroxycinnamic acids include ferulic acid and p-coumaric acid. In some embodiments, combining product 2 and product 1 results in an amla seed product having about 10% to about 60% of fatty acids. The fatty acids include unsaturated and saturated fatty acids. The unsaturated fatty acids include alpha linolenic acid, linoleic acid and oleic acid.

Some embodiments provide an amla seed blend composition as a blend of varying ratios of product 1 (extract from Example 13) and product 2 (extract from Example 13). Product 2 includes triterpenoids and hydroxycinnamic acids. Product 1 includes alpha linolenic acid, linoleic acid and oleic acid. In some embodiments, product 2 and product 1 are blended in a ratio of product 2 to product 1 ranging from about 1:60 to about 99:1. Table A provides how blending of product 2 and product 1 in 1:5 ratio results in a composition having about triterpenoids 8.3%, hydroxycinnamic acid 4.8% and fatty acids 64.6%. Blending of product 2 and product 1 in 1:2 ratio provides an amla seed blend composition having about triterpenoids 16%, hydroxycinnamic acid 9.8% and fatty acids 51.6%. Blending of product 2 and product 1 in 1:1 ratio provides an amla seed blend composition having about triterpenoids 25%, hydroxycinnamic acid 14.65% and fatty acids 38.8%. Blending of product 2 and product 1 in 3:2 ratio provides an amla seed blend composition having about triterpenoids 30%, hydroxycinnamic acid 17.6% and fatty acids 31%. Blending of product 2 and product 1 in 2:1 ratio provides an amla seed blend composition having about triterpenoids 33.3%, hydroxycinnamic acid 19.5% and fatty acids 25.8%. Blending of product 2 and product 1 in 3:1 ratio provides an amla seed blend composition having about triterpenoids 37.5%, hydroxycinnamic acid 22.1% and fatty acids 19.4%. Blending of product 2 and product 1 in 5:1 ratio provides an amla seed blend composition having about triterpenoids 41.6%, hydroxycinnamic acid 24.6% and fatty acids 12.9%. Blending of product 2 and product 1 in 10:1 ratio provides an amla seed blend composition having about triterpenoids 45%, hydroxycinnamic acid 26.6% and fatty acids 7.1%. Blending of product 2 and product 1 in 20:1 ratio provides an amla seed blend composition having about triterpenoids 47.6%, hydroxycinnamic acid 27.9% and fatty acids 3.69%. Blending of product 2 and product 1 in 2:3 ratio provides an amla seed blend composition having about triterpenoids 20%, hydroxycinnamic acid 11.7% and fatty acids 46.2%.

Some embodiments provide a dosage form having the amla seed blend composition, which is a blend of product 2 and product 1 in 1:5, 1:2, 2:3, 1:1, 3:2, 2:1, 3:1, 5:1, 10:1 and 20:1 ratios of product 2 to product 1 but not limited to the above ratios. Some embodiments provide a dosage form having amla seed blend composition and a filler. In some embodiments, amla seed blend composition and filler are blended in a ratio of amla seed blend composition to filler ranging from about 10:1 to about 3:1. In some embodiments, amla seed blend composition and filler are blended in a ratio of extract of seeds of *Emblica officinalis* to filler of about 4.5:1.

In some embodiments, administering theamla seed blend composition which is a blend of product 2 and product 1 in 1:5, 1:2, 2:3, 1:1, 3:2, 2:1, 3:1, 5:1, 10:1 and 20:1 ratios of product 2 to product 1 but not limited to the above ratios, is useful for decreasing total cholesterol, decreasing triglyceride, reducing blood glucose level, enhancing HDL-Cholesterol level, increasing the HDL-Cholesterol to total cholesterol ratio, lowering LDL-Cholesterol level, reducing the CRP level, decreasing the intima media thickening, reducing atherogenic index of plasma, increasing Apo A-1 levels, decreasing Apo B levels, decreasing Apo B to Apo A-1 ratio, reducing Homocysteine level, reduction in glycosylated Hb, modulating TSH level, decreasing HMGCoA reductase activity, lowering total cholesterol without changing CoQ10 levels even at a lower dosage level.

TABLE A

Amla seed blend composition of product 2 and product 1 in different ratios.

| | Product 2 | | Product 1 |
| --- | --- | --- | --- |
| Ratios product 2:product 1 | Triterpenoids (%) | Hydroxycinnamic acid (%) | Fatty acids (%) |
| 1:5 | 8.3 | 4.8 | 64.6 |
| 1:2 | 16 | 9.8 | 51.6 |
| 2:3 (product 3) | 20 | 11.7 | 46.2 |
| 1:1 | 25 | 14.7 | 38.8 |
| 3:2 | 30 | 17.6 | 31 |
| 2:1 | 33.3 | 19.5 | 25.8 |
| 3:1 | 37.5 | 22.1 | 19.4 |
| 5:1 | 41.6 | 24.6 | 12.9 |
| 10:1 | 45 | 26.6 | 7.1 |
| 20:1 | 47.6 | 27.9 | 3.69 |

Figure 13:
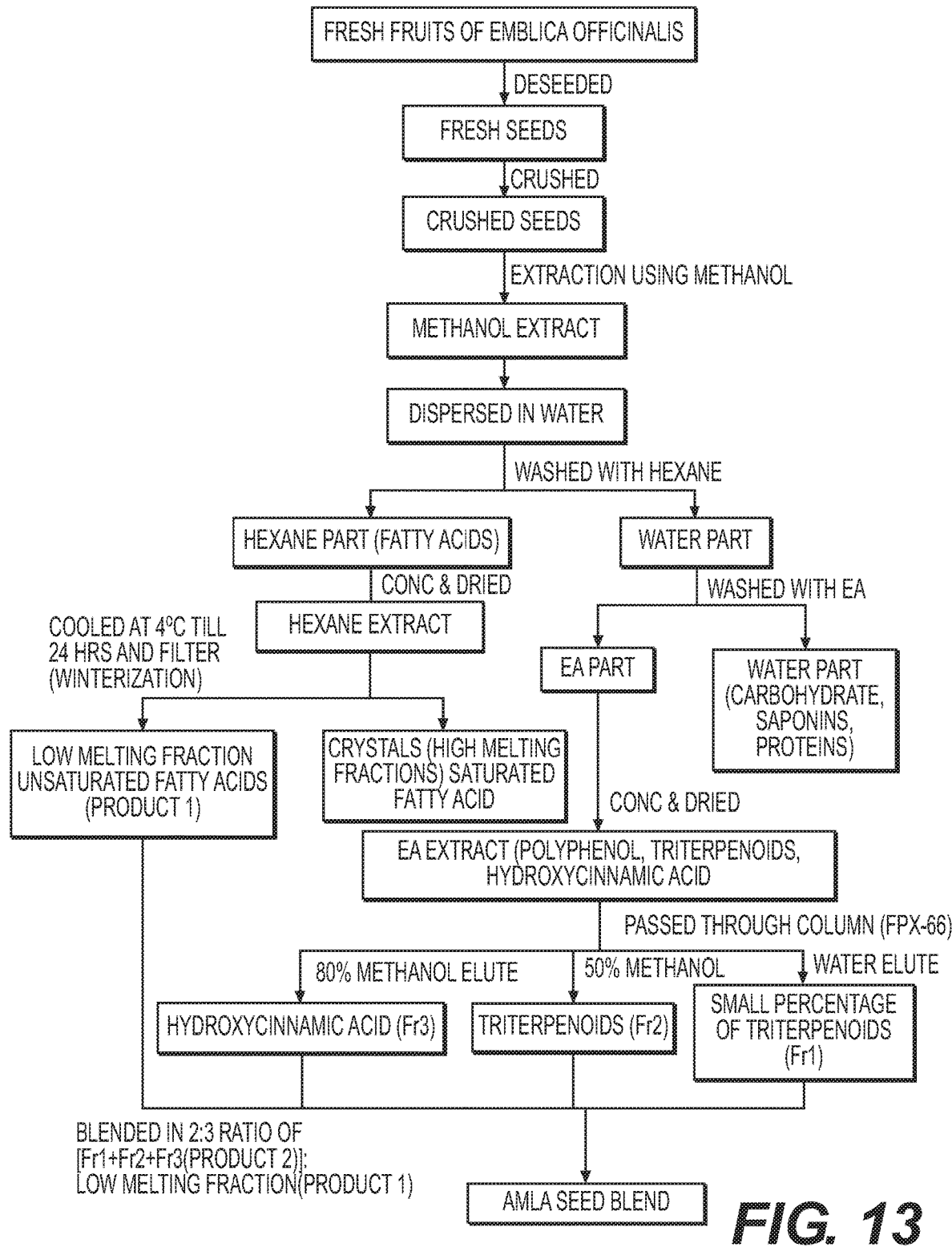
FIG. 13: Flow chart depicting a method of preparation of Amla seed blend composition.

Some embodiments provide a method of preparing an amla seed blend having product 1 and the product 2. Some embodiments provide a method of preparing the product 1. Fresh fruits of *Emblica officinalis* are deseeded to obtain seeds of *Emblica officinalis*. The seeds are crushed. The crushed seeds are extracted with 95% methanol to obtain a residue and a supernatant. The supernatant is concentrated resulting in a concentrated methanol extract. The concentrated methanol extract is dried to obtain a powder of methanol extract of seeds of *Emblica officinalis*. The powder of methanol extract of seeds of *Emblica officinalis* is dispersed in water to obtain a dispersion. The dispersion is extracted with hexane in a liquid-liquid extractor following which a hexane and a water phase is collected. The hexane phase is concentrated to obtain a liquid form of a concentrated hexane extract. The liquid form of the concentrated hexane extract is cooled, whereby obtain precipitates or crystals are formed and a liquid portion is obtained. The liquid portion is separated from the precipitates or crystals to obtain a liquid product 1. Some embodiments provide a method of preparing product 2 from Amla seed. The method includes extracting the water phase collected above after hexane extraction with ethyl acetate to obtain an ethyl acetate phase. The ethyl acetate phase is concentrated to obtain a concentrated ethyl acetate phase. The concentrated ethyl acetate phase is dried to obtain a powder of an ethyl acetate extract. The powder of ethyl acetate extract is mixed with water to obtain a liquid of powder of ethyl acetate extract. The liquid of powder of ethyl acetate extract is loaded onto an ion exchange column. The ion exchange column is eluted with water to obtain a water fraction (also referred to as Fraction 1). Next, the ion exchange column is eluted with 50% methanol to obtain a Fraction 2. Then the ion exchange column is eluted with 80% methanol to obtain a Fraction 3. Fraction 1 is concentrated to obtain a concentrate of Fraction 1. The concentrate of Fraction 1 is dried to obtain a powder of Fraction 1. Fraction 2 is concentrated to obtain a concentrate of Fraction 2. The concentrate of Fraction 2 is dried to obtain a powder of Fraction 2. Fraction 3 is concentrated to obtain a concentrate of Fraction 3. The concentrate of Fraction 3 is dried to obtain a powder of Fraction 3. The powder of Fraction 1, the powder of Fraction 2 and the powder of Fraction 3 are combined to obtain Product 2. Some embodiments of Product 2 have the powder of Fraction 1, the powder of Fraction 2 and the powder of Fraction 3 in a 0.5:1:0.75 ratio of Fraction 1:Fraction 2:Fraction 3. Product 1 includes alpha linolenic acid, linoleic acid and oleic acid. Product 2 includes triterpenoids and hydroxycinnamic acids. In some embodiments, product 2 and product 1 are blended in a ratio of product 2 to product 1 ranging from about 1:1 to about 99:1. In some embodiments, product 2 and product 1 are blended in a ratio of product 2 to product 1 ranging from about 1:60 to about 99:1. In some embodiments, product 2 and product 1 are blended in a ratio of product 2 to product 1 ranging from about 10:1 to about 1:10. In some embodiments, product 2 and product 1 are blended in a ratio of product 2 to product 1 of about 2:3. In some embodiments, product 2 and product 1 are blended in a ratio of product 2 to product 1 of about 1:2. In some embodiments, product 2 and product 1 are blended in a ratio of product 2 to product 1 of about 1:1. In some embodiments, product 2 and product 1 are blended in a ratio of product 2 to product 1 of about 3:2. In some embodiments, product 2 and product 1 are blended in a ratio of product 2 to product 1 of about 10:1 or 90:9. In some embodiments, product 2 and product 1 are blended in a ratio of product 2 to product 1 of about 95:5 or 19:1. In some embodiments, product 2 and product 1 are blended in a ratio of product 2 to product 1 of about 3:1 or 75:25. In some embodiments, product 2 and product 1 are blended in a ratio of product 2 to product 1 of about 1:5. In some embodiments, product 2 and product 1 are blended in a ratio of product 2 to product 1 of about 1:10. In some embodiments, product 2 and product 1 are blended in a ratio of product 2 to product 1 of about 1:3. Method of preparing the extract is provided in FIG. 13.

Some embodiments provide a dosage form having the amla seed blend composition, which is a blend of product 1 and product 2. The dosage forms include a dosage of the amla seed blend composition ranging from about 5 mg to about 500 mg per dose in human subject. The dosage form is administered in single or multiple doses per day. Some embodiments provide a dosage form such as a capsule, tablet, granule, sachet, powder, paste, ointment, infusion, injection, ampoule, solution, suspension, emulsion, pills, oil, or, cream.

Some embodiments provide an amla seed blend composition, which is a blend of product 1 and product 2. Some embodiments provide a method of reducing total cholesterol by administering the amla seed blend composition. Some embodiments provide a method of reducing triglyceride by administering the amla seed blend composition. Some embodiments provide a method of reducing blood glucose level by administering an amla seed blend composition. Some embodiments provide a method of enhancing HDL-Cholesterol by administering an amla seed blend composition. Some embodiments provide a method of increasing a ratio of HDL cholesterol to total cholesterol by administering an amla seed blend composition. Some embodiments provide a method of lowering LDL-Cholesterol levels by administering an amla seed blend composition. Some embodiments provide a method of lowering VLDL by administering an amla seed blend composition. Some embodiments provide a method of reducing CRP level by administering an amla seed blend composition. Some embodiments provide a method of decreasing the intima media thickening by administering an amla seed blend composition. Some embodiments provide a method of reducing hair fall by administering an amla seed blend composition. Some embodiments provide a method of reducing atherogenic index of plasma by administering an amla seed blend composition having Product 1 and Product 2. Some embodiments provide a method of increasing Apo A-1 levels, method of decreasing Apo B levels and method of decreasing the Apo B to Apo A-1 ratio by administering an amla seed blend composition. Some embodiments provide a method of lowering homocysteine level and glycosylated Hb level by administering an amla seed blend composition. Some embodiments provide a method to modulate TSH level by administering an amla seed blend composition. Some embodiments provide a method of lowering HMGCoA reductase activity by administering an amla seed blend composition. Some embodiments provide a method of lowering total cholesterol without a change in CoQ10 levels by administering an amla seed blend composition.

Some embodiments provide a first extract of seeds of *Emblica officinalis* having about 20% to about 70% triterpenoids; and, about 10% to about 40% hydroxycinnamic acids.

Some embodiments provide a blend of extracts of seeds of *Emblica officinalis* having the first extract of seeds of *Emblica officinalis* (some embodiments are provided in Example 27), and, a second extract of *Emblica Officinalis* (some embodiments are provided in Example 13). In the blend of extracts of *Emblica officinalis*, a weight ratio of the first extract of *Emblica Officinalis* to the second extract of *Emblica officinalis* in the blend ranges from about 1:60 to about 99:1. The second extract of *Emblica officinalis* includes fatty acids, such as, alpha linolenic acid, linoleic acid and oleic acid. In some embodiments of the blend of extracts of seeds of *Emblica officinalis*, the weight ratio of the first extract of seeds of *Emblica Officinalis* to the second extract of *Emblica officinalis* in the blend is about 1:1. Some embodiments of the blend of extracts of seeds of *Emblica officinalis* include: about 10% to about 50% triterpenoids; about 3% to about 30% hydroxycinnamic acids, and, about 10% to about 60% of second extract of seeds of *Emblica officinalis*. In some embodiments, the blending of sample 1 and product 1 provides an amla seed blend composition having about 10% to about 50% of triterpenoids. The triterpenoids include among others beta-sitosterol, beta amyrin and lupeol. The hydroxycinnamic acids include ferulic acid and p-coumaric acid. In some embodiments, combining sample 1 and product 1 results in an amla seed product having about 10% to about 60% of fatty acids. The fatty acids include unsaturated and saturated fatty acids. The unsaturated fatty acids include alpha linolenic acid, linoleic acid and oleic acid.

Some embodiments provide an extract of seeds of *Emblica officinalis* having about 0.5% to about 20% triterpenoids, about 0.5% to about 5% of hydroxycinnamic acids, and, about 25% to about 50% fatty acids. In some embodiments, the extract of seeds of *Emblica officinalis* has about 9.5% triterpernoids, about 4.3% hydroxycinnamic acids and about 41.8% fatty acids. Some embodiments provide a dosage form having the extract and a filler. The filler can be lactose, spray dried lactose, starch, dibasic calcium phosphate, tribasic calcium phosphate, microcrystalline cellulose, hydroxy propyl methyl cellulose, calcium carbonate, or combinations thereof. The dosage form can be capsule, tablet, granule, sachet, powder, paste, ointment, infusion, injection, ampoule, solution, suspension, emulsion, pills, oil, or, cream. Some embodiments provide a method of decreasing atherogenic index of plasma in a mammal by administering the extract of seeds of *Emblica officinalis*. The atherogenic index of plasma is a logarithmic ratio of triglycerides to HDL cholesterol. Some embodiments include methods of use of extracts or blends or compositions of *Emblica officinalis* by administering a dosage of extract ranging from about 6 mg to about 500 mg daily for 12 weeks. Other dosages administered include administering about 250 mg to about 500 mg of extracts of *Emblica officinalis*, blend of *Emblica officinalis* or composition having extract or blend of *Emblica officinalis*. Dosages can be administered about two to three times per day for a duration of 12 weeks resulting in the physiological or treatment effects of the disclosed extracts, blends or compositions. Some embodiments provide a method of decreasing risk for coronary heart disease by administering the extract of seeds of *Emblica officinalis*. Some embodiments provide a method of decreasing atherogenic dyslipidemia administering the extract of seeds of *Emblica officinalis*. Some embodiments provide a method of decreasing ratio of Apo B to Apo A1 by administering the extract of seeds of *Emblica officinalis*. Some embodiments provide a method of lowering homocysteine level by administering the extract of seeds of *Emblica officinalis*. Some embodiments provide a method of lowering glycosylated hemoglobin level by administering the extract of seeds of *Emblica officinalis*. Some embodiments provide a method of modulating TSH levels by administering the extract of seeds of *Emblica officinalis*. Some embodiments provide a method of lowering HMGCoA reductase by administering the extract of seeds of *Emblica officinalis*. Some embodiments provide a method of lowering total cholesterol without altering CoQ10 level by administering the extract of seeds of *Emblica officinalis*.

Some embodiments provide a dosage form of the extract of seeds of *Emblica officinalis* and a filler. In some embodiments, extract of seeds of *Emblica officinalis* and filler are blended in a ratio of extract of seeds of *Emblica officinalis* to filler ranging from about 10:1 to about 3:1. In some embodiments, extract of seeds of *Emblica officinalis* and filler are blended in a ratio of extract of seeds of *Emblica officinalis* to filler of about 5:1. In some embodiments, extract of seeds of *Emblica officinalis* and filler are blended in a ratio of extract of seeds of *Emblica officinalis* to filler of about 6:1. In some embodiments, extract of seeds of *Emblica officinalis* and filler are blended in a ratio of extract of seeds of *Emblica officinalis* to filler of about 4.5:1.

In another embodiment, 500 mg capsule having extract of seeds of *Emblica officinalis* and filler includes a first extract to filler ratio of about 10:1 to about 3:1. Some embodiments have a ratio extract of seeds of *Emblica officinalis* to fillers of about 4.5:1. A 500 mg capsule of extract of seeds of *Emblica officinalis* with filler has about 400 mg to about 440 mg of extract of seeds of *Emblica officinalis*. Some embodiments have about 430 mg of the extract of seeds of *Emblica officinalis*. Some embodiments have about 410 mg of extract of seeds of *Emblica officinalis*. A 500 mg capsule of extract of seeds of *Emblica officinalis* with filler can have about 60 mg to about 100 mg of filler. Some embodiments have about 90 mg filler. A 500 mg capsule of extract of seeds of *Emblica officinalis* and filler can have triterpenoids ranging from about 25 mg to about 40 mg, hydroxycinnamic acid ranging from about 10 mg to about 20 mg and fatty acids ranging from about 130 mg to about 150 mg. In some embodiments of the dosage form, the triterpenoids can be about 31.98 mg, hydroxycinnamic acid about 14.35 mg and fatty acid about 140.6 mg.

Some embodiments of the amla seed blend composition are referred to as Sample 2. Sample 2 is a blend of varying ratios of sample 1 and product 1. Product 1 includes alpha linolenic acid, linoleic acid and oleic acid. Sample 1 includes triterpenoids and hydroxycinnamic acids. In some embodiments, sample 1 and product 1 are blended in a ratio of sample 1 to product 1 ranging from about 1:1 to about 99:1. In some embodiments, sample 1 and product 1 are blended in a ratio of sample 1 to product 1 ranging from about 1:60 to about 99:1. In some embodiments, sample 1 and product 1 are blended in a ratio of sample 1 to product 1 ranging from about 1:1 to about 1:10. In some embodiments, sample 1 and product 1 are blended in a ratio of sample 1 to product 1 of about 2:3. In some embodiments, sample 1 and product 1 are blended in a ratio of sample 1 to product 1 of about 1:2. In some embodiments, sample 1 and product 1 are blended in a ratio of sample 1 to product 1 of about 1:1. In some embodiments, sample 1 and product 1 are blended in a ratio of sample 1 to product 1 of about 3:2. In some embodiments, sample 1 and product 1 are blended in a ratio of sample 1 to product 1 of about 10:1 or 90:9. In some embodiments, sample 1 and product 1 are blended in a ratio of sample 1 to product 1 of about 95:5 or 19:1. In some embodiments, sample 1 and product 1 are blended in a ratio of sample 1 to product 1 of about 3:1 or 75:25. In some embodiments, sample 1 and product 1 are blended in a ratio of sample 1 to product 1 of about 1:5. In some embodiments, sample 1 and product 1 are blended in a ratio of sample 1 to product 1 of about 1:10. In some embodiments, sample 1 and product 1 are blended in a ratio of sample 1 to product 1 of about 1:3.

Some embodiments provide an amla seed blend composition. The amla seed blend composition is a blend of varying ratios of sample 1 (extract from Example 27) and product 1 (extract from Example 13). Sample 2 includes triterpenoids and hydroxycinnamic acids. Product 1 includes alpha linolenic acid, linoleic acid and oleic acid. In some embodiments, sample 1 and product 1 are blended in a ratio of sample 1 to product 1 ranging from about 1:60 to about 99:1. Table B provides how blending of sample 1 and product 1 in 1:5 ratio provides an amla seed blend composition having about triterpenoids 10.6%, hydroxycinnamic acid 4.5% and fatty acids 64.6%. Blending of sample 1 and product 1 in 1:2 ratio provides an amla seed blend composition having about triterpenoids 21.2%, hydroxycinnamic acid 9% and fatty acids 51.6%. Blending of sample 1 and product 1 in 2:3 ratio provides an amla seed blend composition having about triterpenoids 25.4%, hydroxycinnamic acid 10.8% and fatty acids 46.2%. Blending of sample 1 and product 1 in 3:2 ratio provides an amla seed blend composition having about triterpenoids 38.1%, hydroxycinnamic acid 16.2% and fatty acids 31%. Blending of sample 1 and product 1 in 2:1 ratio provides an amla seed blend composition having about triterpenoids 42.3%, hydroxycinnamic acid 18% and fatty acids 25.8%. Blending of sample 1 and Product 1 in 3:1 ratio provides an amla seed blend composition having about triterpenoids 37.5%, hydroxycinnamic acid 22.1% and fatty acids 19.4%. Blending of Sample 1 and product 1 in 5:1 ratio provides an amla seed blend composition having about triterpenoids 52.9%, hydroxycinnamic acid 22.5% and fatty acids 12.9%. Blending of sample 1and product 1 in 10:1 ratio provides an amla seed blend composition having about triterpenoids 57.7%, hydroxycinnamic acid 24.5% and fatty acids 7.1%. Blending of sample 1 and product 1 in 20:1 ratio provides an amla seed blend composition having about triterpenoids 60.5%, hydroxycinnamic acid 25.7% and fatty acids 3.7%. Blending of sample 1 and product 1 in 1:1 ratio provides an amla seed blend composition having about triterpenoids 31.8%, hydroxycinnamic acid 13.5% and fatty acids 38.8%.

Some embodiments provide a dosage form having the amla seed blend composition, which is a blend of sample 1 and product 1 in 1:5, 1:2, 2:3, 1:1, 3:2, 2:1, 3:1, 5:1, 10:1 and 20:1 ratios of sample 1 to product 1 but not limited to the above ratios. Some embodiments provide a dosage form having amla seed blend composition and a filler. In some embodiments, amla seed blend composition and filler are blended in a ratio of amla seed blend composition to filler ranging from about 10:1 to about 3:1. In some embodiments, amla seed blend composition and filler are blended in a ratio of extract of seeds of *Emblica officinalis* to filler of about 4.5:1.

Sample 1 and product 1 in 1:5, 1:2, 2:3, 1:1, 3:2, 2:1, 3:1, 5:1, 10:1 and 20:1 ratios of sample 1 to product 1 but not limited to the above ratios, is useful for decreasing total cholesterol, decreasing triglyceride, reducing blood glucose level, enhancing HDL-Cholesterol level, increasing the HDL-Cholesterol to total cholesterol ratio, lowering LDL-Cholesterol level, reducing the CRP level, decreasing the intima media thickening, reducing atherogenic index of plasma, increasing Apo A-1 levels, decreasing Apo B levels, decreasing Apo B to Apo A-1 ratio, reducing Homocysteine level, reduction in glycosylated Hb, modulating TSH level, decreasing HMGCoA reductase activity, lowering total cholesterol without changing CoQ10 levels even at a lower dosage level.

TABLE B

Amla seed blend composition of sample1 and product 1 in different ratios

| Ratios Sample 1:Product 1 | Sample 1 | | Product 1 |
|---|---|---|---|
| | Triterpenoids (%) | Hydroxycinnamic acid (%) | Fatty acids (%) |
| 1:5 | 10.6 | 4.5 | 64.6 |
| 1:2 | 21.2 | 9 | 51.6 |
| 2:3 | 25.4 | 10.8 | 46.2 |
| 1:1(Sample 2) | 31.8 | 13.5 | 38.8 |
| 3:2 | 38.1 | 16.2 | 31 |
| 2:1 | 42.3 | 18 | 25.8 |
| 3:1 | 47.6 | 20.3 | 19.4 |
| 5:1 | 52.9 | 22.5 | 12.9 |
| 10:1 | 57.7 | 24.5 | 7.1 |
| 20:1 | 60.5 | 25.7 | 3.7 |

Some embodiments provide a dosage form of the first extract of seeds of *Emblica officinalis* and a filler. The filler can be lactose, spray dried lactose, starch, dibasic calcium phosphate, tribasic calcium phosphate, microcrystalline cellulose, hydroxy propyl methyl cellulose, or calcium carbonate, or combinations thereof. The dosage form can be capsule, tablet, granule, sachet, powder, paste, ointment, infusion, injection, ampoule, solution, suspension, emulsion, pills, oil, or, cream.

Some embodiments provide a dosage form of the first extract of seeds of *Emblica officinalis* and a filler. In some embodiments, first extract of seeds of *Emblica officinalis* and filler are blended in a ratio of first extract of seeds of *Emblica officinalis* to filler ranging from about 10:1 to about 3:1. In some embodiments, first extract of seeds of *Emblica officinalis* and filler are blended in a ratio of first extract of seeds of *Emblica officinalis* to filler of about 5:1. In some embodiments, first extract of seeds of *Emblica officinalis* and filler are blended in a ratio of first extract of seeds of *Emblica officinalis* to filler of about 6:1. In some embodiments, first extract of seeds of *Emblica officinalis* and filler are blended in a ratio of first extract of seeds of *Emblica officinalis* to filler of about 4.5:1.

In another embodiment, 500 mg capsule having a first extract of seeds of *Emblica officinalis* and filler includes a first extract to filler ratio of about 10:1 to about 3:1. Some embodiments have a ratio of first extract to fillers of about 4.5:1. A 500 mg capsule of first extract of seeds of *Emblica officinalis* with filler has about 400 mg to about 440 mg of first extract of seeds of *Emblica officinalis*. Some embodiments have about 430 mg of the first extract. Some embodiments have about 410 mg of the first extract of seeds of *Emblica officinalis*. A 500 mg capsule of first extract of seeds of *Emblica officinalis* with filler can have about 60 mg to about 100 mg of filler. Some embodiments have about 90 mg filler. A 500 mg capsule of first extract of seeds of *Emblica officinalis* and filler can have triterpenoids ranging from about 200 mg to about 240 mg and hydroxycinnamic acid ranging from about 80 mg to about 100 mg. In some embodiments of the dosage form, the triterpenoids can be about 213.5 mg and hydroxycinnamic acid can be about 90.8 mg.

Some embodiments provide a dosage form of the blend of extracts of seeds of *Emblica officinalis* and a filler. The blend of extracts of seeds of *Emblica officinalis* has a first extract of seeds of *Emblica officinalis*, and, a second extract of *Emblica Officinalis* (referred to as Product 1 from Example 13). The fillers include lactose, spray dried lactose, starch, dibasic calcium phosphate, tribasic calcium phosphate, microcrystalline cellulose, hydroxy propyl methyl cellulose, or calcium carbonate, or combinations thereof. The dosage forms include capsule, tablet, granule, sachet, powder, paste, ointment, infusion, injection, ampoule, solution, suspension, emulsion, pills, oil, or, cream.

Some embodiments provide a dosage form of the blend of extracts of seeds of *Emblica officinalis* and a filler. The blend of extracts of seeds of *Emblica officinalis* has a first extract of seeds of *Emblica officinalis*, and, a second extract of *Emblica Officinalis* (referred to as Product 1 from Example 13). In some embodiments, blend of extracts of seeds of *Emblica officinalis* and filler are blended in a ratio of blend of extracts of seeds of *Emblica officinalis* to filler ranging from about 10:1 to about 3:1. In some embodiments, blend of extracts of seeds of *Emblica officinalis* and filler are blended in a ratio of blend of extracts of seeds of *Emblica officinalis* to filler of about 5:1. In some embodiments, blend of extract of seeds of *Emblica officinalis* and filler are blended in a ratio of blend of seeds of *Emblica officinalis* to filler of about 6:1. In some embodiments, blend of extract of seeds of *Emblica officinalis* and filler are blended in a ratio of blend of seeds of *Emblica officinalis* to filler of about 4.5:1.

In another embodiment, 500 mg capsule having blend of extract of seeds of *Emblica officinalis* and filler includes blend of extract of seeds of *Emblica officinalis* to filler ratio of about 10:1 to about 3:1. Some embodiments have a ratio of blend of extract of seeds of *Emblica officinalis* to fillers of about 4.5:1. A 500 mg capsule of blend of extract of seeds of *Emblica officinalis* with filler has about 400 mg to about 440 mg of blend of extract of seeds of *Emblica officinalis*. Some embodiments have about 430 mg of the blend of extract of seeds of *Emblica officinalis*. Some embodiments have about 410 mg of the blend of extract of seeds of *Emblica officinalis*. A 500 mg capsule of blend of extract of seeds of *Emblica officinalis* with filler can have about 60 mg to about 100 mg of filler. Some embodiments have about 90 mg filler. A 500 mg capsule of blend of extract of seeds of *Emblica officinalis* and filler can have triterpenoids ranging from about 100 mg to about 120 mg, hydroxycinnamic acid ranging from about 40 mg to about 55 mg and fatty acid ranging from about 120 mg to about 140 mg. In some embodiments of the dosage form, the triterpenoids can be about 107.6 mg, hydroxycinnamic acid can be about 45.4 mg and fatty acids can be about 129.8 mg.

Some embodiments provide a method of preparing a first extract (sample 1) of seeds of *Emblica officinalis*. The method includes deseeding fresh fruits of *Emblica officinalis* to obtain fresh seeds. Then crushing fresh seeds to obtain crushed seeds. Next, the crushed seeds are extracted with methanol to obtain a residue and a supernatant. The supernatant is concentrated to obtain a concentrated methanol extract. The concentrated methanol extract is dried to obtain a first powder. The first powder of methanol extract of seeds of *Emblica officinalis* is macerated with water to obtain a mixture. The mixture is extracted with ethyl acetate to obtain an ethyl acetate phase and an aqueous phase. The ethyl acetate phase is concentrated to obtain a concentrated ethyl acetate extract. The concentrated ethyl acetate extract is dried to obtain a second powder. The second powder is refluxed with 50% methanol to obtain a 50% methanol part and an oil part. The 50% methanol part is concentrated to obtain a concentrated methanol part. The concentrated methanol part is loaded onto an HP20 column to obtain an extract loaded HP20 column. The loaded HP20 column is eluted first with ethyl acetate and then eluted with 100% methanol to obtain an ethyl acetate elute and a methanol elute. The methanol elute is concentrated to obtain a concentrated methanol elute. The methanol elute is dried to obtain a third powder, which is referred to as the first extract of seeds of *Emblica officinalis*. The first extract of seeds of *Emblica officinalis* includes about 20% to about 70% triterpenoids, and, about 10% to about 40% hydroxycinnamic acids.

Figure 14A:
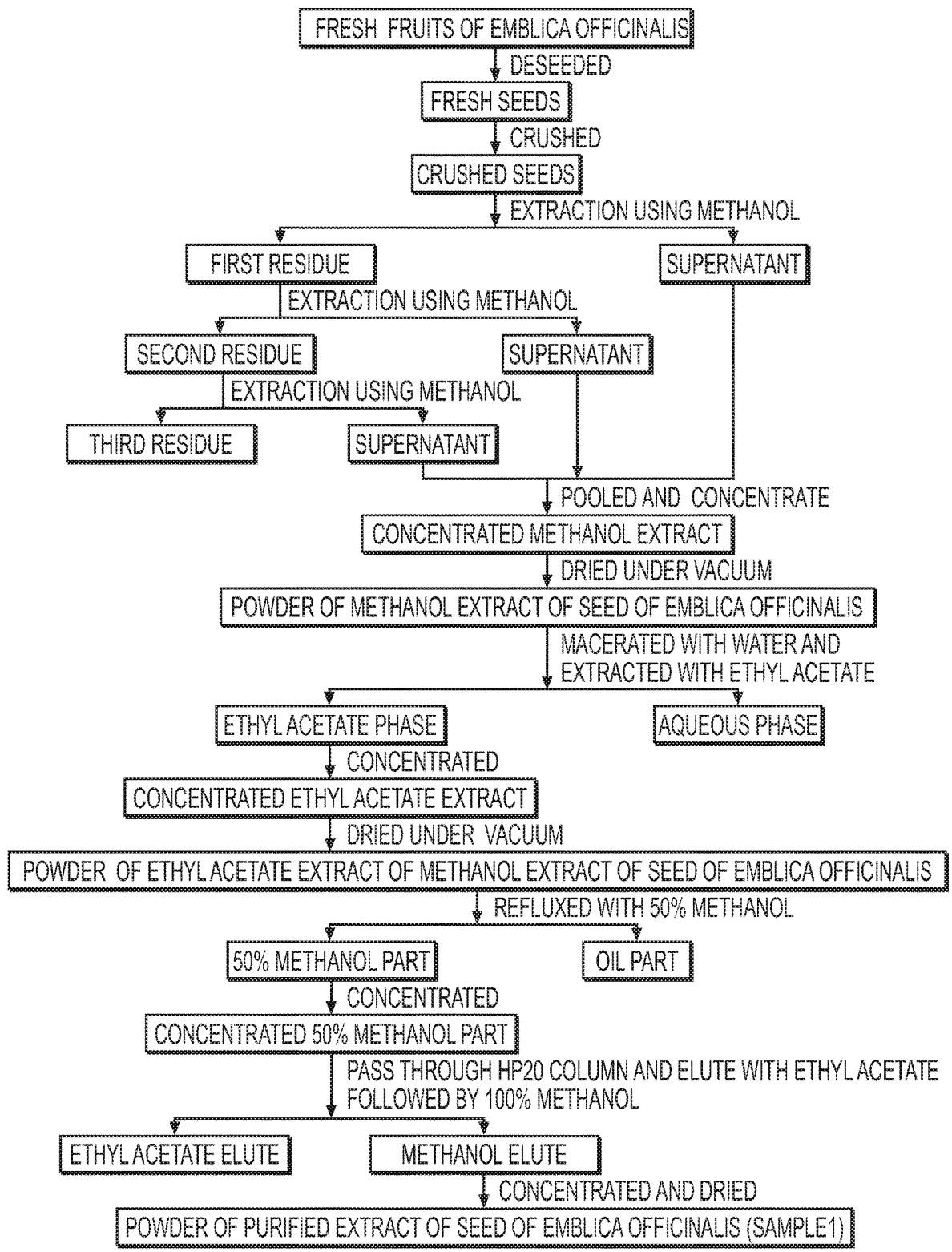
FIGS. 14A and 14B.
Figure 14B:
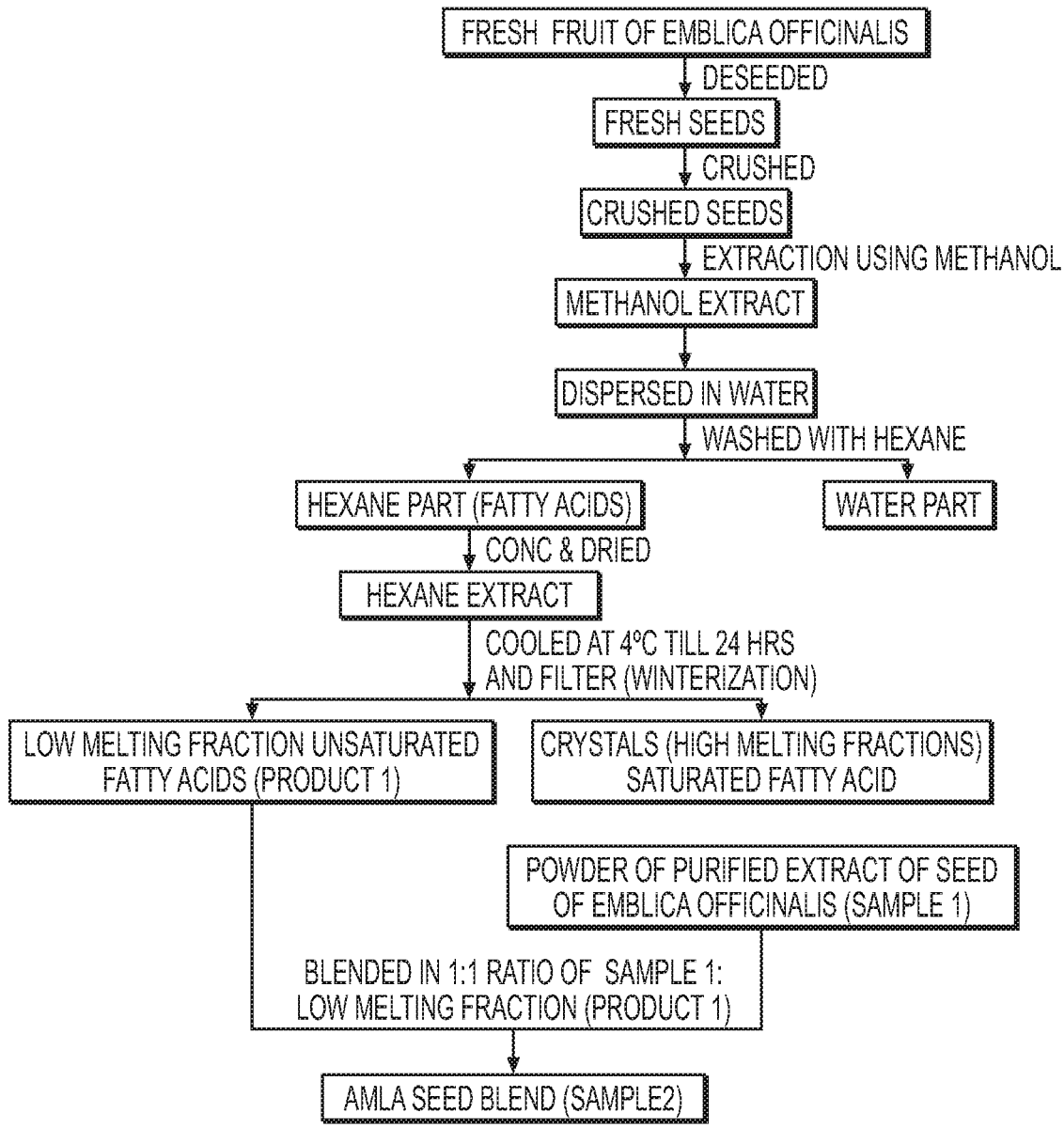

Some embodiments provide a method of preparing a blend of extracts of seeds of *Emblica officinalis*. The blend includes the first extract of seeds of *Emblica officinalis* and a second extract (some embodiments are referred to as product 1) of seeds of *Emblica officinalis*. The method of preparing the blend includes blending the first extract of seeds of *Emblica officinalis* and the second extract of seeds of *Emblica officinalis* in a weight ratio ranging from about 1:60 to about 99:1. The second extract of seeds of *Emblica officinalis* is prepared by a method including deseeding fresh fruits of *Emblica officinalis* to obtain seeds of *Emblica officinalis*. Next the seeds of *Emblica officinalis* are crushed to obtain crushed seeds. The crushed seeds are extracted with 95% methanol to obtain a residue and a supernatant. The supernatant is concentrated to obtain a concentrated methanol extract. The concentrated methanol extract is dried to obtain a powder of methanol extract of seeds of *Emblica officinalis*. The powder of methanol extract of seeds of *Emblica officinalis* is dispersed in water to obtain a dispersion. The dispersion is extracted with hexane to obtain a water phase and a hexane phase. The hexane phase is concentrated to obtain a liquid form of a concentrated hexane extract. The liquid form of the concentrated hexane extract is cooled to obtain precipitates or crystals, and, a liquid portion. The liquid portion is separated from the precipitates or crystals to obtain a liquid. This liquid is the second extract of seeds of *Emblica officinalis*. The second extract of seeds of *Emblica officinalis* includes alpha linolenic acid, linoleic acid and oleic acid. Method of preparing a first extract of seeds of *Emblica officinalis* (also referred to as sample 1), second extract of seeds of *Emblica officinalis* (also referred to as product 1) and a blend of the first extract and the second extract of seeds of *Emblica officinalis* is provided in FIGS. 14A and 14B.

Some embodiments provide a method of lowering total cholesterol by administering the first extract of seeds of *Emblica officinalis*. Some embodiments provide a method of lowering triglycerides by administering the first extract of seeds of *Emblica officinalis*. Some embodiments provide a method of lowering VLDL cholesterol by administering the first extract of seeds of *Emblica officinalis*. Some embodiments provide a method of lowering LDL cholesterol by administering the first extract of seeds of *Emblica officinalis*. Some embodiments provide a method of enhancing HDL cholesterol by administering the first extract of seeds of *Emblica officinalis*. Some embodiments provide a method of increasing a ratio between HDL to total cholesterol by administering the first extract of seeds of *Emblica officinalis*. Some embodiments provide a method of reducing blood glucose level by administering an amla seed blend composition. Some embodiments provide a method of reducing hair fall by administering an amla seed blend composition. Some embodiments provide a method of decreasing atherogenic index of plasma by administering the first extract of seeds of *Emblica officinalis*. Some embodiments provide a method of decreasing risk for coronary heart disease by administering the first extract of seeds of *Emblica officinalis*. Some embodiments provide a method of decreasing atherogenic dyslipidemia by administering the first extract of seeds of *Emblica officinalis*. Some embodiments provide a method of decreasing the ratio of Apo B to Apo A1 by administering the first extract of seeds of *Emblica officinalis*. Some embodiments provide a method of lowering homocysteine level by administering the first extract of seeds of *Emblica officinalis*. Some embodiments provide a method of lowering glycosylated hemoglobin level by administering the first extract of seeds of *Emblica officinalis*. Some embodiments provide a method of modulating TSH levels by administering the first extract of seeds of *Emblica officinalis*. Modulating refers to correcting the abnormal TSH levels to normal range of TSH. For example, if a subject has a lower than normal TSH level, administering the extract would increase TSH but only upto normal range and not to hyperthyroid range. However, if a subject has higher than normal TSH level, extract administration will lower the TSH to normal range but not to the hypothyroid range. In some embodiments, extract administration increases TSH levels. In some embodiments, it decreases TSH levels. And in some embodiments, TSH level is not affected by extract administration. Some embodiments provide a method of lowering HMG-CoA reductase by administering the first extract of seeds of *Emblica officinalis*. In some embodiments a method of lowering total cholesterol without altering CoQ10 level by administering the first extract of seeds of *Emblica officinalis* is provided.

Some embodiments provide a method of lowering total cholesterol by administering a blend of extracts of seeds of *Emblica officinalis*. The blend includes the first extract of *Emblica officinalis* and the second extract of *Emblica officinalis*. A method of lowering triglycerides by administering the blend of extracts of seeds of *Emblica officinalis* is provided. A method of lowering VLDL cholesterol administering the blend of extracts of seeds of *Emblica officinalis*. Some embodiments provide a method of lowering LDL cholesterol by administering the blend of extracts of seeds of *Emblica officinalis*. Some embodiments provide a method enhancing HDL cholesterol by administering the blend of extracts of seeds of *Emblica officinalis*. Methods of increasing a ratio between HDL to total cholesterol by administering the blend of extracts of seeds of *Emblica officinalis* is provided. Some embodiments provide a method of reducing blood glucose level by administering an amla seed blend composition. Some embodiments provide a method of reducing hair fall by administering an amla seed blend composition. Methods of decreasing atherogenic index of plasma by administering the blend of extracts of seeds of *Emblica officinalis* is provided. Methods of decreasing risk for coronary heart disease by administering the blend of extracts of seeds of *Emblica officinalis* is provided. Methods of decreasing atherogenic dyslipidemia by administering the blend of extracts of seeds of *Emblica officinalis* is provided. Method of decreasing ratio of Apo B to Apo A1 by administering the blend of extracts of seeds of *Emblica officinalis* is provided. Methods of lowering homocysteine level by administering the blend of extracts of seeds of *Emblica officinalis* is provided. Methods of lowering glycosylated hemoglobin level by administering the blend of extracts of seeds of *Emblica officinalis* is provided. Methods of modulating TSH by administering the blend of extracts of seeds of *Emblica officinalis* is provided. Methods of lowering HMGCoA reductase by administering the blend of extracts of seeds of *Emblica officinalis* is provided. Methods for lowering total cholesterol without altering CoQ10 level by administering the blend of extracts seeds of *Emblica officinalis* is provided.

It will be readily understood by the skilled artisan that numerous alterations may be made to the examples and instructions given herein. These and other objects and features of the invention will be made apparent from the following examples. The following examples as described are not intended to be construed as limiting the scope of the present invention.

Example 1

Method of Preparation of Ethyl Acetate Extract of Methanol Extract of Seed of *Emblica officinalis*

500 Kg of fresh fruits of *Emblica officinalis* (Amla) were collected. Fruits were deseeded by deseeding machine and 75 Kg of fresh seeds obtained were crushed through roller mill. 95% Methanol in an amount 2 times the quantity of crushed seeds was added to the crushed seeds to form a mixture for methanol extraction. The extraction was performed using an extractor with reflux condenser. The bottom of the extractor was fitted with a polypropylene (100 microns) filter cloth. The mixture was refluxed for one hour at 65° C. to obtain a first residue and supernatant. The residue and supernatants were separated by draining out the supernatant from the extractor bottom through the polypropylene filter cloth using a centrifugal pump. After the first extraction, the first residue was further extracted with two times the quantity of methanol at 65° C. to get second residue and supernatant. The second residue was further extracted with two times the quantity of methanol at 65° C. to get third residue and supernatant. All the supernatants were pooled and concentrated in an Agitated thin film evaporator (ATFE) at a temperature of 65° C. to form concentrated methanol extract. Concentrated methanol extract was dried under vacuum at above 500 mm of mercury to obtain 5 kg of powder of methanol extract of seed of *Emblica officinalis*.

The powder of methanol extract of seed of *Emblica officinalis* was macerated with water and transferred into a liquid-liquid extractor and extracted with ethyl acetate. Ethyl acetate phase and aqueous phase were separated. After extraction ethyl acetate phase was collected. Ethyl acetate phase was concentrated in an Agitated thin film evaporator to form concentrated ethyl acetate extract. Ethyl acetate concentrate was fed into vacuum stripper and dried under vacuum at above 500 mm of mercury to obtain 2.5 kg of powder of ethyl acetate extract of methanol extract of seed of *Emblica Officinalis*. Method of preparing the extract is provided in FIG. 1.

Powder of ethyl acetate extract of methanol extract of seed of *Emblica officinalis* had 9.5% triterpenoids, 4.3% hydroxycinnamic acids and 41.8% fatty acids.

2 Kg powder of ethyl acetate extract of methanol extract of seed of *Emblica officinalis* was blended with 0.45 kg of microcrystalline cellulose in a Double Cone Blender (stainless steel SS-316, capacity 2000 litre, manufacturer: Zebra Pharma, Mumbai) for 1 hour to obtain a total of 2.45 kg blend of powder of ethyl acetate extract of methanol extract of seed of *Emblica officinalis* and microcrystalline cellulose.

2.45 Kg blend composition had 7.8% triterpenoids, 3.5% hydroxycinnamic acids and 34.3% fatty acids.

Example 2

Method of Preparation of Ethyl Acetate Extract of Seed of *Emblica officinalis*

500 Kg of fresh fruits of *Emblica officinalis* were collected. Fruits were deseeded by deseeding machine and 75

Kg fresh seeds obtained were crushed through roller mill. Crushed seeds were filled in the Soxhlet extractor and extracted with ethyl acetate (300 L). The extraction was carried out for 5 hrs at a temperature of about 78° C. After the completion of extraction, the supernatant was filtered and concentrated in an Agitated thin film evaporator (ATFE) at a temperature of 75° C. to form concentrated ethyl acetate extract. Concentrated ethyl acetate extract was dried under vacuum at above 500 mm of mercury to get 2 Kg of powder of ethyl acetate extract of seed of *Emblica officinalis*. Method of preparing the *Emblica officinalis* extract is provided in FIG. 2.

Example 3

Method of Preparation of Pectinase Treated Water Extract of Fruits of *Emblica officinalis*

100 Kg of fresh fruits of *Emblica officinalis* were collected. Fresh fruits of *Emblica officinalis* were pulped with demineralized water to create slurry. The slurry was treated with pectinase and then filtered to obtain a solution. The solution was concentrated and dried under vacuum. 5 Kg of dried product was pulverized and sieved through 30 meshes to obtain a powder of a pectinase treated water extract of *Emblica officinalis*.

Example 4

Method of Preparation of Alcoholic Extract of Fruits of *Emblica officinalis*

100 Kg of fresh fruits of *Emblica officinalis* were collected. Fresh fruits of *Emblica officinalis* were pulverized. 95% Methanol in an amount 2 times the quantity (200 L) of pulverized fruits were added to form a mixture for methanol extraction. The extraction was performed using an extractor with reflux condenser. The bottom of the extractor was fitted with a polypropylene (100 microns) filter cloth. The mixture was refluxed for one hour at 65° C. to obtain a residue and supernatant. The residue and supernatants were separated by draining out the supernatant from the extractor bottom through the polypropylene filter cloth using a centrifugal pump. After the first extraction, the residue was further extracted with two times the quantity of methanol at 65° C. to get a residue and a supernatant. The residue was further extracted with two times the quantity of methanol at 65° C. to get third residue and supernatant. All the supernatants were pooled and concentrated in an Agitated thin film evaporator (ATFE) at a temperature of 65° C. to form concentrated methanol extract. Concentrated methanol extract was dried under vacuum at above 500 mm of mercury to obtain 5 kilograms of powder of methanol extract of fruit of *Emblica Officinalis*. Method of preparing extract is provided in FIG. 4.

Example 5

Method of Preparation of Pectinase Treated Water Extract of Deseeded *Emblica officinalis*

100 Kg of fresh fruits of *Emblica officinalis* were collected. Fresh fruits of *Emblica officinalis* were deseeded by deseeding machine to obtain 85 Kg deseeded fruit. Deseeded *Emblica officinalis* fruits were pulped with demineralized water to create slurry. The slurry was treated with pectinase and then filtered to obtain a solution. The solution was concentrated and dried under vacuum. 4 Kg of dried product was pulverized and sieved through 30 meshes to obtain a powder of a pectinase treated water extract of deseeded *Emblica officinalis*. Method of preparing extract is provided in FIG. 5.

Example 6

Method of Preparation of Alcoholic Extract of Deseeded *Emblica officinalis*

100 Kg of fresh fruits of *Emblica officinalis* were collected. Fresh fruits of *Emblica officinalis* were deseeded by deseeding machine to obtain 85 Kg deseeded *Emblica officinalis* fruits. Deseeded *Emblica officinalis* fruits were pulverized. 95% methanol in an amount 2 times the quantity (170 L) of pulverized fruits was added to form a mixture for methanol extraction. The extraction was performed using an extractor with reflux condenser. The bottom of the extractor was fitted with a polypropylene (100 microns) filter cloth. The mixture was refluxed for one hour at 65° C. to obtain a first residue and supernatant. The residue and supernatants were separated by draining out the supernatant from the extractor bottom through the polypropylene filter cloth using a centrifugal pump. After the first extraction, the first residue was further extracted with two times the quantity of methanol at 65° C. to get second residue and supernatant. The second residue was further extracted with two times the quantity of methanol at 65° C. to get third residue and supernatant. All the supernatants were pooled and concentrated in an Agitated thin film evaporator (ATFE) at a temperature of 65° C. to form concentrated methanol extract. Concentrated methanol extract was dried under vacuum at above 500 mm of mercury to obtain 3.5 kilograms of powder of methanol extract of deseeded fruit of *Emblica officinalis*. Method of preparing extract is provided in FIG. 6.

Example 7

Method of Preparation of Powder of Dried Amla Seed

Figure 7:
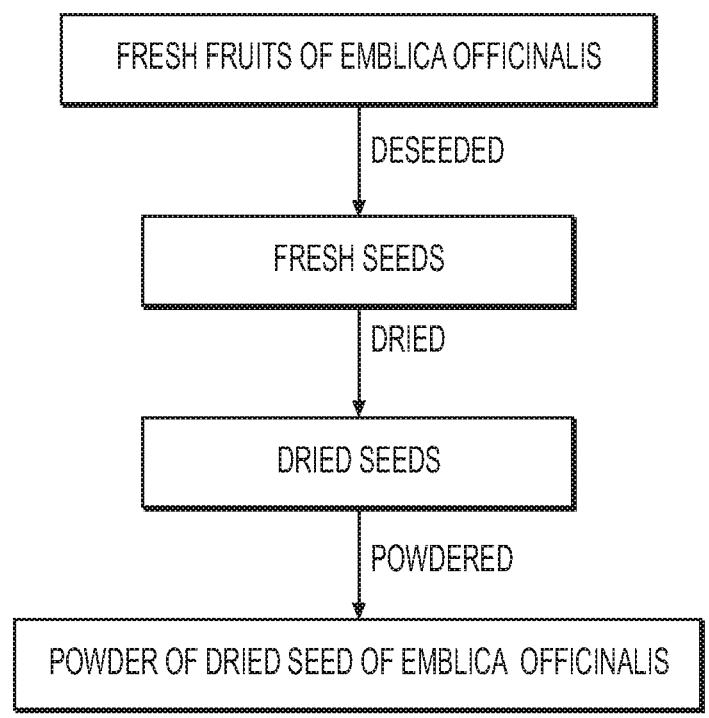
FIG. 7: Flow chart depicting a method of preparation of powder of dried seed of *Emblica officinalis*.

10 Kg of fresh fruits of *Emblica officinalis* (Amla) were collected. Fruits were deseeded by deseeding machine and 1.5 Kg of fresh seeds obtained was dried in tray drier at 40° C. The dried material was powdered to obtain 0.75 Kg powder of dried seed of *Emblica officinalis*. Method of preparing extract is provided in FIG. 7.

Example 8

Method of Preparation of Water Extract of Dried Amla Seed

Figure 8:
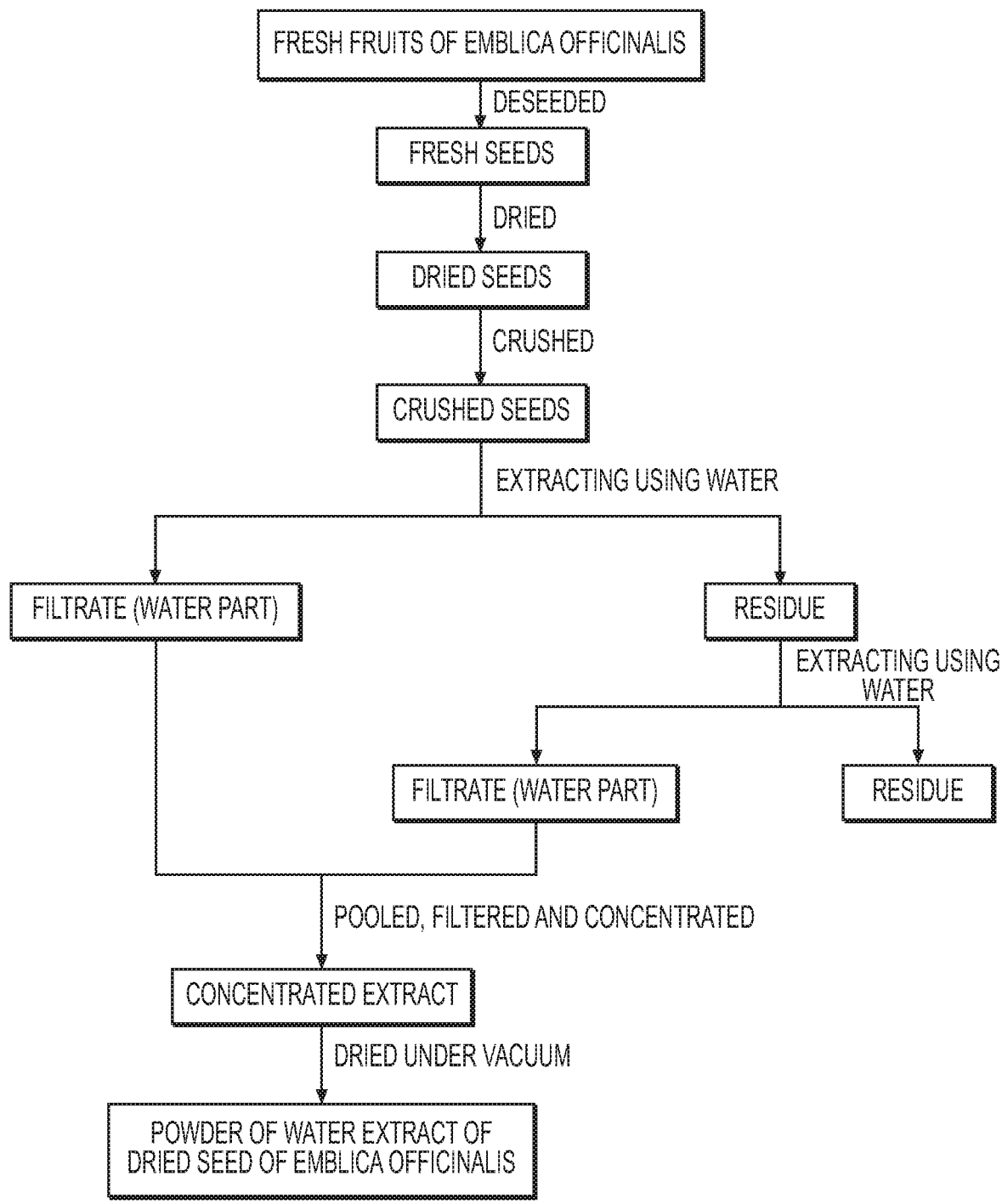
FIG. 8: Flow chart depicting a method of preparation of powder of water extract of dried seed of *Emblica officinalis*.

500 Kg of fresh fruits of *Emblica officinalis* (Amla) were collected. Fruits were deseeded by deseeding machine to obtain 75 Kg fresh seeds. Fresh seeds were dried in tray drier at 40° C. The dried seeds were crushed and charged in to an extractor. Around 200 Litres of water was added into the crushed seed and kept for a contact time of 3 hrs. Then the water part was collected and fresh water was again added into seeds and repeated the extraction thrice. All the water parts were pooled, filtered and concentrated in an evaporator, when the concentrated water extract of dried seed reached the bottom of the vessel, the concentrate was fed into drier and dried under vacuum above 500 mm of mercury. Dried product was discharged from the bottom of the vessel and pulverized to obtain 4 Kg powder of the water extract of dried seed of *Emblica officinalis*. Method of preparing extract is provided in FIG. 8.

Example 9

Method of Preparation of Methanol Extract of Dried Amla Seed

Figure 9:
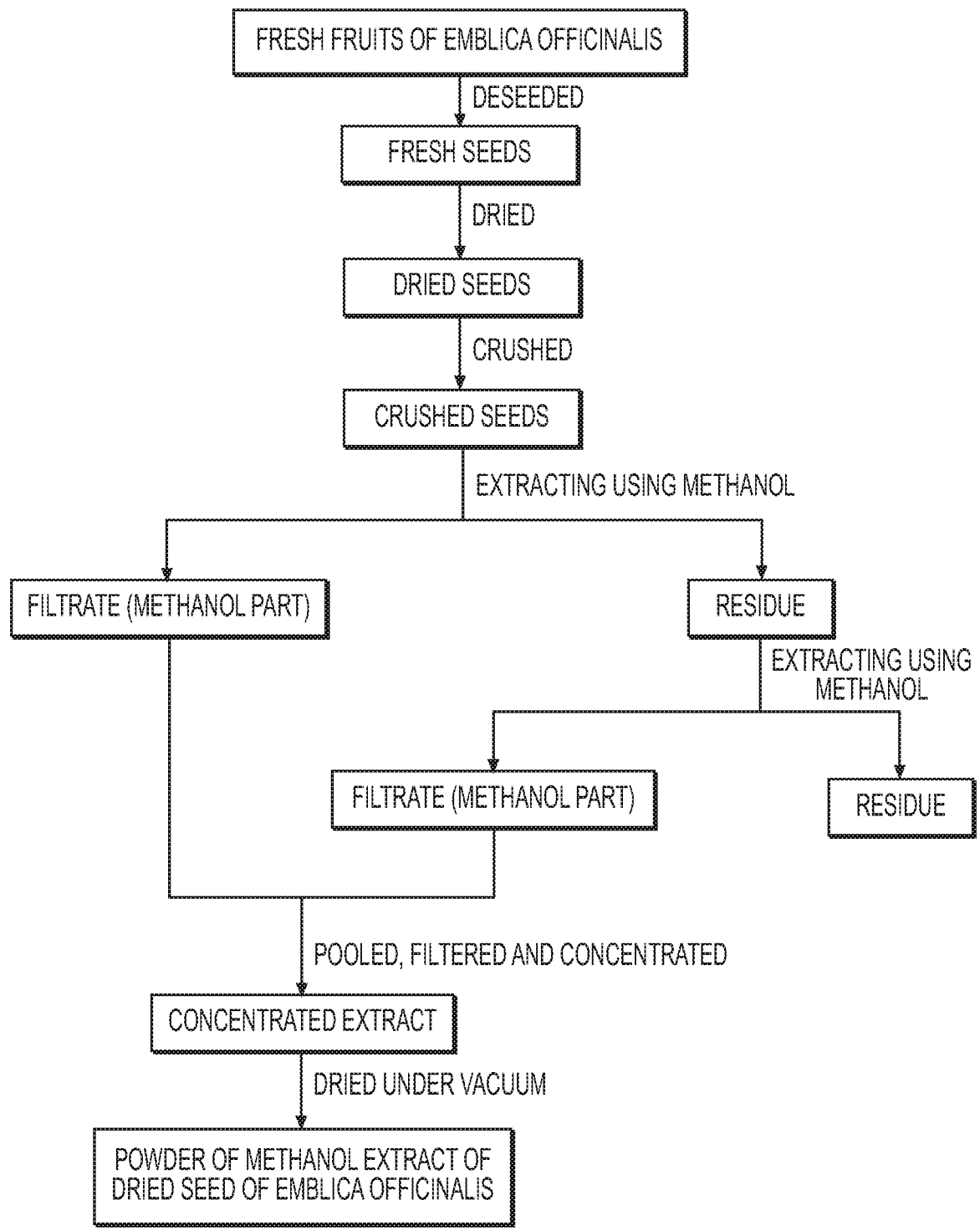
FIG. 9: Flow chart depicting a method of preparation of powder of methanol extract of dried seed of *Emblica officinalis*.

500 Kg of fresh fruits of *Emblica officinalis* (Amla) were collected. Fruits were deseeded by deseeding machine to obtain 75 Kg fresh seeds. Fresh seeds were dried in tray drier at 40° C. The dried seeds were crushed and charged into an extractor. Around 200 litres of 95% methyl alcohol was pumped into the extractor and kept for a contact time of 3 hours. Then the solvent part (methanol part) was collected and fresh methyl alcohol pumped again into the extractor and extraction repeated thrice. All the extracts (methanol part) were pooled, filtered and dried in an Agitated thin film drier (ATFD) which was working under vacuum 700 mm Mercury. Dried product was discharged from the bottom of the vessel and then pulverized to obtain 5 Kg powder of an alcoholic extract of seed of *Emblica officinalis*. The method of preparing extract is provided in FIG. 9.

Example 10

Method of Preparation of Powder of Dried Amla Fruit

Figure 10:
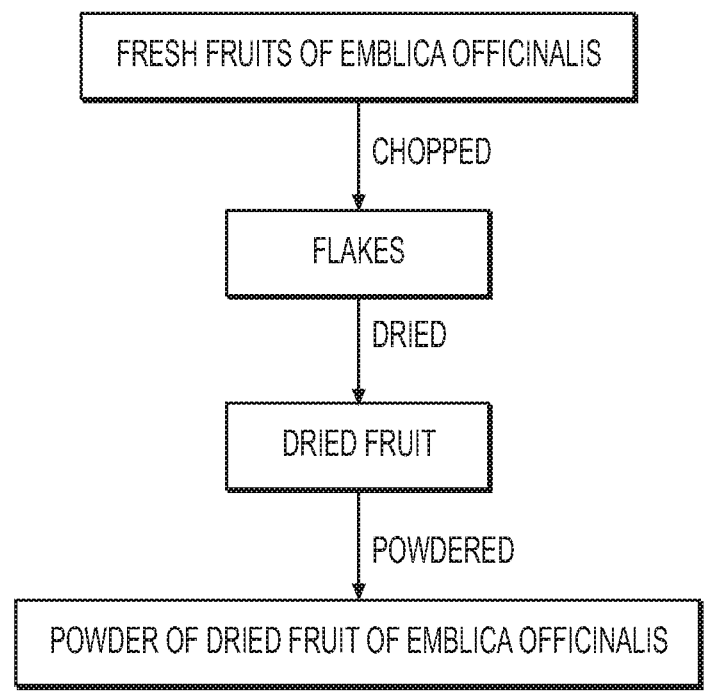
FIG. 10: Flow chart depicting a method of preparation of powder of fruit of *Emblica officinalis*.

Fresh fruits of *Emblica officinalis* 100 kgs were washed and chopped into flakes and dried in a hot air oven at around 110° C. for 10 hours. 9 Kg of dried material was powdered to obtain a powder of dried fruits of *Emblica officinalis*. The method of preparing extract is provided in FIG. 10.

Example 11

Method of Preparation of Water Extract of Dried Amla Fruit

Figure 11:
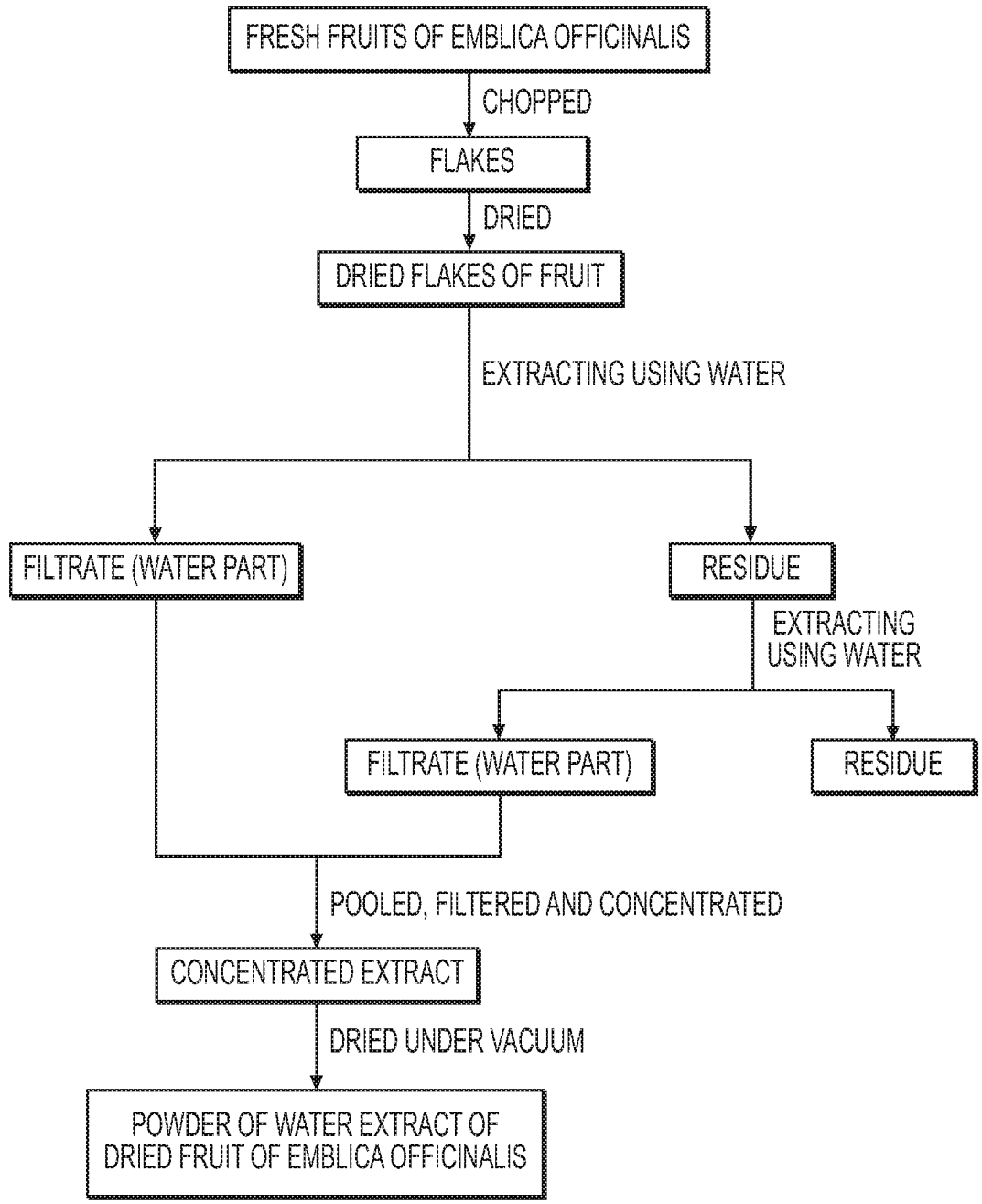
FIG. 11: Flow chart depicting a method of preparation of powder of water extract of fruit of *Emblica officinalis*.

100 Kg of fresh fruits of *Emblica officinalis* were collected. Fresh fruits were washed and chopped into flakes and dried in a hot air oven at around 110° C. for 10 hours. Dried flakes were charged in to an extractor and around 200 Liters of water was added into the dried flakes and kept for a contact time of 3 hrs. Then the water part was collected and water was again added into flakes and repeated thrice. All the water parts were pooled, filtered and concentrated in an evaporator, when the concentrated water extract of dried fruit reached the bottom of the vessel, the concentrate was fed into drier and dried under vacuum above 500 mm of mercury. 6 Kg of dried product was discharged from the bottom of the vessel and pulverized to obtain a powder of the water extract of dried fruits of *Emblica officinalis*. The method of preparing extract is provided in FIG. 11.

Example 12

Method of Preparation of Methanol Extract of Dried Amla Fruit

Figure 12:
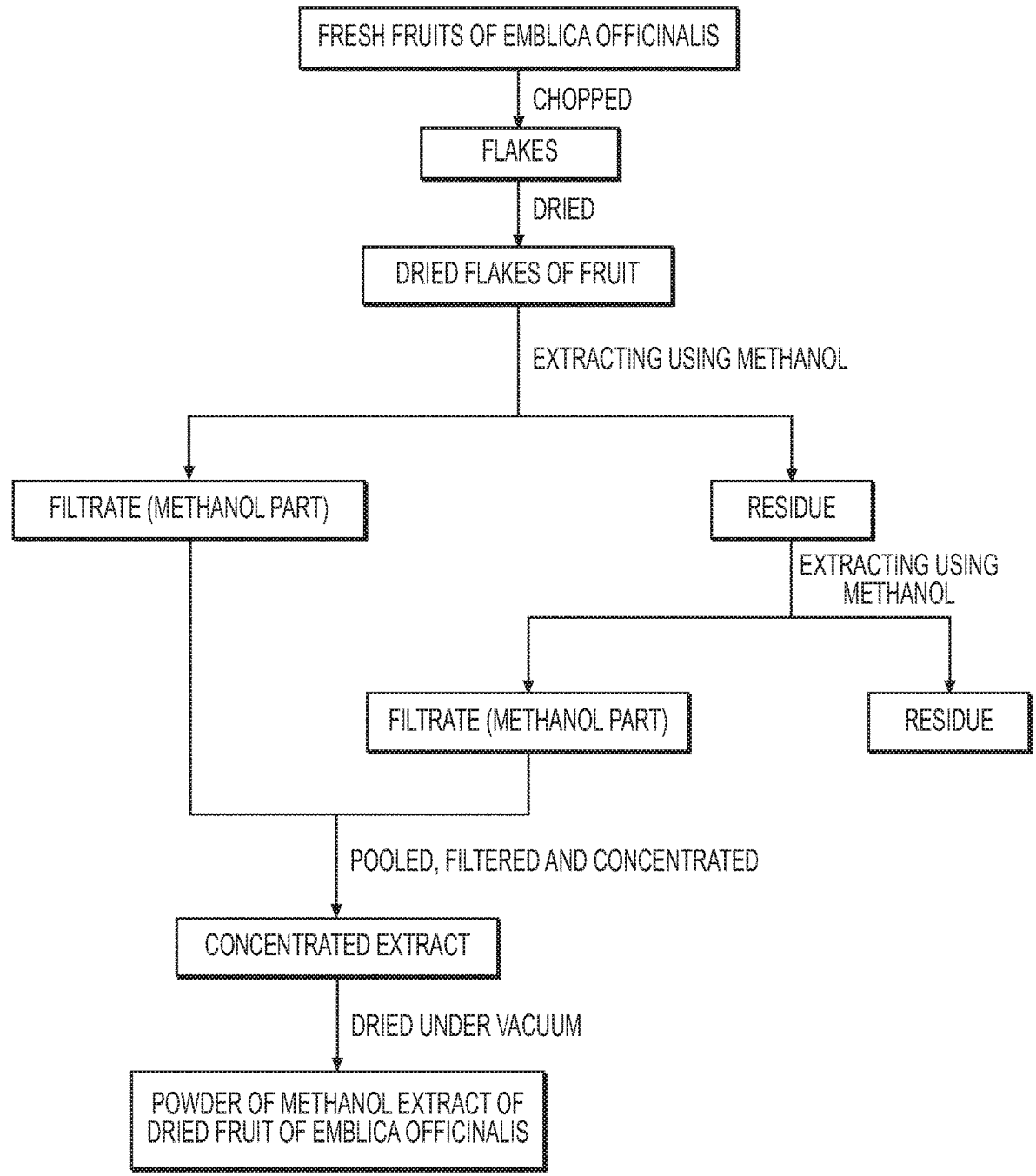
FIG. 12: Flow chart depicting a method of preparation of powder of methanol extract of fruit of *Emblica officinalis*.

100 Kg of fresh fruits of *Emblica officinalis* were collected. Fresh fruits were washed and chopped into flakes and dried in a hot air oven at around 110° C. for 10 hours. Dried flakes were charged in to an extractor and around 200 liters of 95% methyl alcohol was pumped into the extractor and kept for a contact time of 3 hours. Then the solvent part (methanol part) was collected and fresh methyl alcohol pumped again into the extractor and extraction repeated thrice. All the extracts (methanol part) were pooled, filtered and dried in an Agitated thin film drier (ATFD) which was working under vacuum 700 mm Mercury. 5 Kg of dried product was discharged from the bottom of the vessel and then pulverized to obtain of powder of an alcoholic extract of fruits of *Emblica officinalis*. The method of preparing extract is provided in FIG. 12.

Example 13

Method of Enrichment of Triterpinoids and Hydroxycinimic Acid Blending with Fatty Acid in a Amla Seed Extract 500 Kg of fresh fruits of *Emblica officinalis* (Amla) were collected. Fruits were deseeded by deseeding machine to obtain 75 Kg of fresh seeds of amla. The fresh seeds were crushed through roller mill. 95% methanol in an amount 2 times the quantity of crushed seeds was added to the crushed seeds to form a mixture for methanol extraction. The extraction was performed using an extractor with reflux condenser. The bottom of the extractor was fitted with a polypropylene (100 microns) filter cloth. The mixture was refluxed for one hour at 65° C. to obtain a first residue and supernatant. The first residue and supernatant were separated by draining out the supernatant from the extractor bottom through the polypropylene filter cloth using a centrifugal pump. After the first extraction, the first residue was further extracted with two times the quantity of methanol at 65° C. to get a second residue and supernatant. The second residue was further extracted with two times the quantity of methanol at 65° C. to get a third residue and supernatant. All the supernatants were pooled and concentrated in an Agitated thin film evaporator (ATFE) at a temperature of 65° C. to form a concentrated methanol extract. The concentrated methanol extract was dried under vacuum at above 500 mm of mercury to obtain 5 kg of powder of methanol extract of seed of *Emblica officinalis*.

The powder of methanol extract of seed of *Emblica officinalis* was dispersed in water and transferred into a liquid-liquid extractor and extracted with hexane. After extraction hexane phase and aqueous phase separated. Then the hexane phase was collected through side valve. Hexane phase was concentrated in an Agitated thin film evaporator to form 2 Kg of concentrated hexane extract. The concentrated hexane extract was cooled at 4° C. and kept cold for 24 hrs. Some components of the concentrated hexane extract precipitated or crystallized by this cooling. The crystals or precipitates were separated from the liquid cooled concentrated hexane extract by passing the cooled concentrated hexane extract through a filter press. The precipitates or crystals were found to contain high melting point components such as palmitic acid and stearic acid. 1.5 kilograms of liquid (product 1) was obtained after passing through the cooled concentrated hexane extract in the filter press. Product 1 was found to contain 77.5% unsaturated fatty acids such as 34.2% alpha-linolenic acid, 26.3% linolenic acid, and 16.5% oleic acid.

Ethyl acetate was added to aqueous phase in a liquid-liquid extractor for extraction. After extraction ethyl acetate phase and aqueous phase were separated and ethyl acetate phase was collected through side valve. Ethyl acetate phase was concentrated in an Agitated thin film evaporator to form concentrated ethyl acetate extract. Ethyl acetate concentrate was fed into vacuum stripper and dried under vacuum at above 500 mm of mercury to obtain 2.5 kilograms of powder of ethyl acetate extract of methanol extract of seed of *Emblica officinalis*. This extract was found to contain triterpenoids and polyphenols. Polyphenols included hydroxycinnamic acid.

Powder of ethyl acetate extract of methanol extract of seed of *Emblica officinalis* was mixed with water and loaded in a column having a FPX 66 ion-exchange resin (Rohm & Haas, Philadelphia, USA). The column chromatography was performed to further purify the triterpenoids, and, to separate hydroxycinnamic acids from other polyphenols. Column was initially eluted with water and water fraction was collected. Then the column was eluted with different concentrations of methanol (50% methanol and 80% methanol) and collected the different methanol fractions. Water fraction was concentrated and dried under vacuum to form of powder of water elute of ethyl acetate extract of seed of *Emblica officinalis* with an yield of 0.1 Kg denoted as Fraction 1. Fraction 1 was found to contain small amount of triterpenoids which was confirmed by HPLC. The 50% methanol fraction was concentrated and dried under vacuum to form powder of 50% methanol elute of ethyl acetate extract of seed of *Emblica officinalis* with an yield of 1 kg denoted as Fraction 2. Fraction 2 was found to contain triterpenoids and it was confirmed by HPLC.

80% methanol fraction was concentrated and dried under vacuum to form powder of 80% methanol elute of ethyl acetate extract of seed of *Emblica officinalis* with an yield of 0.75 kg denoted as Fraction 3. Fraction 3 was found to contain hydroxycinnamic acids confirmed by HPLC method.

Fractions 1, 2 and 3 were combined to form a product 2. Product 2 was blended with product 1 in a 2:3 ratio to form an amla seed blend product 3 with an yield of 3.35 Kg. The method of preparing extract is provided in FIG. 13. Product 3 had about 20% triterpenoids, about 11.7% hydroxycinnamic acids, about 46.2% unsaturated fatty acids and about 0.3% saturated fatty acids. Product 3 included about 9% beta sito sterol, about 6% beta amyrin, about 5% lupeol, about 7.5% ferulic acid, about 4.2% coumaric acid, about 20.5% alpha linolenic acid, about 15.8% linolenic acid, about 9.9% oleic acid, about 0.2% stearic acid and about 0.1% palmitic acid.

Example 14

Analysis of Triterpenoids by HPLC

The triterpenoids was estimated by high performance liquid chromatography (HPLC-DAD) on a C18 column (250×4.6 mm). The mobile phase was acetonitrile used under isocratic condition with an eluent flow rate of 1 ml/min.

Standard was prepared by weighing 5 mg of standards lupeol, beta amyrin and betasitosterol (95% purity) and was made up to 10 ml with acetonitrile and stored in darkness at 4° C. Sample was prepared by weighing 50 mg of the extract and was made up to 50 ml with acetonitrile and stored in darkness at 4° C. Both the sample and standard were filtered separately through a 0.2 µm membrane filter before injection into the HPLC column. The injection volume was 20 µl. The triterpenoids was detected at 210 nm. By comparing the area of standard and sample, the percentage of triterpenoids present in the sample was quantified. (Separation and identification of some common isomeric plant triterpenoids by thin-layer chromatography and high-performance liquid chromatography, Mitja et al, J Chromatogr A 2009 Sep. 18; 1216(38):6662-70. doi: 0.1016/j.chroma.2009.07.038. Epub 2009 Jul. 29.).

Example 15

Analysis of Hydroxycinnamic Acids by HPLC

The hydroxycinnamic acids were estimated by high performance liquid chromatography (HPLC-DAD) on a C18 column (250×4.6 mm). The mobile phase was Solvent A-1% acetic acid in water, solvent B-1% acetic acid/water/acetonitrile (2:68:30). Gradient: 0 min. 7% B increased to 90% B. Flow rate 1 ml/min. Detection at 320 nm.

Standard was prepared by weighing 5 mg of standards ferulic acid and p-coumaric acid (95% purity) and was made up to 10 ml with methanol and stored in darkness at 4° C. Sample was prepared by weighing 50 mg of extract and was made up to 50 ml with methanol and stored in darkness at 4° C. Both the sample and standard were filtered separately through a 0.2 µm membrane filter before injection into the HPLC column. The injection volume was 20 µl. The hydroxycinnamic acids were detected at 320 nm. By comparing the area of standard and sample, the percentage of hydroxycinnamic acids present in the sample was quantified. (A "Novel Protocol for the Analysis of Hydroxycinnamic Acids in Leaf Tissue of Chicory (*Cichorium intybus L., Asteraceae*), http://www.hindawi.com/45870319/Meriem Bahri et al, the scientific world journal, volume 2012, Article ID 142983.)

Example 16

Analysis of Fatty Acids by GC

Fatty acids were analysed by gas chromatography method. 250 mg of standard oil fatty acid methyl ester was weighed in 25 ml standard flask and made up to 25 ml with isooctane. 1 microlitre of the standard solution was injected in GC. Retention time of each component was found out.

0.3 gm of the sample (extract) was weighed into a 100 ml RB flask and 1.5 ml of 0.5 N methanolic NaOH was added. Sample was kept in a boiling water bath with a water condenser and heated at 100° C. for 5 minute. Cooled and 2 ml of boron tri fluoride (BF3)-Methanol solution was added and heated at 100° C. for 30 minutes. Cooled to 30-40° C. and 5 ml isooctane was added and shook vigorously for 30 seconds.

5 ml of saturated NaCl solution was added immediately and shook vigorously and cooled to room temperature. Iso-octane layer was separated and aqueous layer was again extracted with iso-octane. Isooctane layers were mixed and dried. Then made up the residue to 25 ml with iso-octane and 2 micro litre was injected in GC. Retention time of each component was found out and compared with components of standard with the same retention time. By comparing the area of standard and sample, the percentage of fatty acids present in the sample was quantified. (European Pharmacopoeia, fifth edition, vol 1, ISBN: 92-871-5281-0, p-110).

Example 17

Determination of Polyphenol Content

The polyphenol was estimated by high performance liquid chromatography (HPLC-DAD) on a C18 column (250×4.6 mm). The mobile phase was Solvent A-0.1% Trifluro acetic acid in water, solvent B-Methanol. Isocratic (90:10) Flow rate 1 ml/min. Detection at 254 nm.

Standard was prepared by weighing 5 mg of standards gallic acid and ellagic acid (95% purity) and was made up to 10 ml with methanol and stored in darkness at 4° C. Sample was prepared by weighing 50 mg of the extract and was made up to 50 ml with methanol and stored in darkness at 4° C. Both the sample and standard were filtered separately through a 0.2 μm membrane filter before injection into the HPLC column. The injection volume was 20 μl. The polyphenol was detected at 254 nm. By comparing the area of standard and sample, the percentage of polyphenol present in the sample was quantified. (HPLC Profiles of Standard Phenolic Compounds Present in Medicinal Plants, Gupta et al, International Journal of Pharmacognosy and Phytochemical Research 2012; 4(3); 162-167.)

Example 18

Screening of Hypolipidemic Activity of Amla Seed Extract Using Triton WR 1339 Induced Dyslipidemia Model Twenty four male Albino rats (Sprague Dawley strain) weighing approximate 250-300 gm were selected for the study. The animals were kept in the animal house maintained at temp 24±2° C., 65% relative humidity and 12 hr light/dark cycle. The rats were acclimatized for two weeks and during this period they had access to standard pellet diet and water ad libitum. After two weeks of acclimatization, all the rats were fasted overnight before injecting Triton WR 1339 (Tyloxapol) and administration of test extracts/standard. The animals were divided into four groups Following treatment was given to overnight fasted rats:
Group I: Normal control (vehicle only).
Group II: Triton WR 1339 (300 mg/kg, intraperitoneal).
Group III: Triton WR 1339 (300 mg/kg, intraperitoneal) followed by amla seed extract prepare as per example 1 (10 mg/kg, per oral).
Group IV: Triton WR 1339 (300 mg/kg, intraperitoneal) followed by Atorvastatin (10 mg/kg, per oral).

The animals were deprived of food for next 24 hours but had free access to water ad libitum. After 24 hour of drug treatment 2 ml blood samples were collected from the retro orbital plexus. The blood was allowed to clot and then centrifuged at 3000 rpm for 10 min and the serum was carefully drawn and collected into separate tubes. The serum was analyzed for total cholesterol, triglycerides, high density lipoproteins (HDL), low density lipoproteins (LDL) and very low density lipoproteins (VLDL) levels using autoanalyzer.

TABLE 1(A)

Lipid profile (mg/dl) of rats treated with Amla seed extract.

| Groups | TC | | TG | | HDL | |
|---|---|---|---|---|---|---|
| | Before | After | Before | After | Before | After |
| Normal control. | 111.87 | 134.77 | 52.20 | 62.03 | 37.80 | 58.03 |
| Triton only. | 108.3 | 265.6 | 43.06 | 692.7 | 36.13 | 49.5 |
| Triton + Amla seed extract (10 mg/Kg). | 117.2 | 120.87 | 58.63 | 152.23 | 39.4 | 47.27 |

TABLE 1(A)-continued

Lipid profile (mg/dl) of rats treated with Amla seed extract.

| Groups | TC | | TG | | HDL | |
|---|---|---|---|---|---|---|
| | Before | After | Before | After | Before | After |
| Triton + Atorvastatin (10 mg/kg). | 100.4 | 131.9 | 44.26 | 109.67 | 29.13 | 32.37 |

TABLE 1(B)

Lipid profile (mg/dl) of rats treated with Amla seed extract.

| Groups | LDL | | VLDL | |
|---|---|---|---|---|
| | Before | After | Before | After |
| Normal control. | 63.69 | 64.37 | 10.44 | 12.41 |
| Triton only. | 63.59 | 77.59 | 8.62 | 138.55 |
| Triton + Amla seed extract (10 mg/Kg). | 66.03 | 43.15 | 11.72 | 30.44 |
| Triton + Atorvastatin (10 mg/kg). | 62.43 | 77.61 | 8.85 | 21.93 |

Results indicated that before treatment the baseline value of total cholesterol, triglyceride, HDL, LDL and VLDL in all groups were comparable. Injecting Triton alone (Group II) significantly increased the total cholesterol level to 265.6 mg/dl. Whereas in Group III, simultaneous oral administration of amla seed extract in triton injected rats, cholesterol level was 120.87 mg/dl which was 2.2 times lower as compared to triton alone group.

In group II triton injection increased the triglyceride level to 692.7 mg/dl. Whereas in Group III, simultaneous oral administration of amla seed extract in triton injected rats, triglyceride level was 152.23 mg/dl which was 4.5 times lower as compared to triton alone group.

In triton alone group after triton injection the ratio of HDL to total cholesterol was 0.18. Whereas in Group III, simultaneous oral administration of amla seed extract in triton injected rats, the ratio of HDL cholesterol to total cholesterol was 0.39 which was 2.2 times higher as compared to triton alone group.

In group II triton injection increased the LDL level to 77.59 mg/dl. Whereas in Group III, simultaneous oral administration of amla seed extract in triton injected rats, LDL level was 43.15 mg/dl which was 1.8 times lower as compared to triton alone group.

In group II triton injection increased the VLDL level to 138.55 mg/dl. Whereas in Group III, simultaneous oral administration of amla seed extract in triton injected rats, VLDL level was 30.44 mg/dl which was 4.6 times lower as compared to triton alone group.

The standard drug Atorvastatin was also effective in lowering the cholesterol as well as triglyceride level. These results clearly indicate the hypolipidemic activity of amla seed extract in triton induced hyperlipidemia in rats.

Example 19

Hypolipidemic Activity of Amla Seed Extracts in Different Doses Using Triton WR 1339 Induced Dyslipidemia Model Sixty male Albino rats (Sprague Dawley strain) weighing approximate 250-300 gm were selected for the study. The animals were kept in the animal house maintained at temp 24±2° C., 65% relative humidity and 12 hr light/dark cycle. The rats were acclimatized for two weeks and during this period they had access to standard pellet diet and water ad libitum. After two weeks of acclimatization, all the rats were fasted overnight before injecting Triton WR 1339 (Tyloxapol) and administration of test extracts/standard. The animals were divided into ten groups. Following treatment was given to overnight fasted rats:

Group I: Normal control (vehicle only).
Group II: Triton WR 1339 (300 mg/kg, intraperitoneal).
Group III: Triton WR 1339 (300 mg/kg, intraperitoneal) followed by amla seed extract prepare as per example 1 (10 mg/kg, per oral).
Group IV: Triton WR 1339 (300 mg/kg, intraperitoneal) followed by amla seed extract prepare as per example 1 (7.5 mg/kg, per oral).
Group V: Triton WR 1339 (300 mg/kg, intraperitoneal) followed by amla seed extract prepare as per example 1 (5 mg/kg, per oral).
Group VI: Triton WR 1339 (300 mg/kg, intraperitoneal) followed by amla seed extract prepare as per example 1 (2.5 mg/kg, per oral).
Group VII: Triton WR 1339 (300 mg/kg, intraperitoneal) followed by amla seed extract prepare as per example 1 (2 mg/kg, per oral).
Group VIII: Triton WR 1339 (300 mg/kg, intraperitoneal) followed by amla seed extract prepare as per example 1 (1 mg/kg, per oral).
Group IX: Triton WR 1339 (300 mg/kg, intraperitoneal) followed by amla seed extract prepare as per example 1 (0.5 mg/kg, per oral).
Group X: Triton WR 1339 (300 mg/kg, intraperitoneal) followed by atorvastatin (10 mg/kg, per oral).

The animals were deprived of food for next 24 hours but had free access to water ad libitum. After 24 hour of drug treatment 2 ml blood samples were collected from the retro orbital plexus. The blood was allowed to clot and then centrifuged at 3000 rpm for 10 min and the serum was carefully drawn and collected into separate tubes. The serum was analyzed for total cholesterol, triglycerides, high density lipoproteins (HDL), low density lipoproteins (LDL) and very low density lipoproteins (VLDL) levels using autoanalyzer.

TABLE 2(A)

Lipid profile (mg/dl) of rats treated with amla seed extract in different doses.

| Groups | TC | | TG | | HDL | |
|---|---|---|---|---|---|---|
| | Before | After | Before | After | Before | After |
| Normal control. | 105.52 | 111.36 | 49.38 | 40.55 | 30.12 | 33.67 |
| Triton only. | 110.53 | 233.76 | 50.5 | 504.3 | 46.3 | 54.66 |
| Triton + amla seed extract 10 mg/Kg. | 111.1 | 108.23 | 51.23 | 91.1 | 45.46 | 48.66 |
| Triton + amla seed extract 7.5 mg/Kg. | 91.9 | 114 | 62.53 | 171.18 | 30.41 | 36.51 |
| Triton + amla seed extract 5 mg/Kg. | 85.46 | 112.26 | 45.61 | 120.43 | 29.68 | 40.33 |
| Triton + amla seed extract 2.5 mg/Kg. | 104.66 | 116.25 | 55.28 | 116.31 | 36.41 | 43.28 |
| Triton + amla seed extract 2 mg/Kg. | 96.35 | 118.54 | 49.53 | 105.56 | 38.55 | 41.26 |
| Triton + amla seed extract 1 mg/Kg. | 101.25 | 121.55 | 58.33 | 125.56 | 40.25 | 42.58 |
| Triton + amla seed extract 0.5 mg/Kg. | 110.66 | 126.61 | 55.48 | 122.28 | 46.26 | 47.41 |
| Triton + atorvastatin 10 mg/kg. | 87.43 | 120.83 | 39.9 | 103.86 | 31.66 | 39.83 |

TABLE 2(B)

Lipid profile (mg/dl) of rats treated with amla seed extract in different doses.

| Groups | LDL | | VLDL | |
|---|---|---|---|---|
| | Before | After | Before | After |
| Normal control. | 67.55 | 71.64 | 9.85 | 8.09 |
| Triton only. | 47.46 | 78.24 | 10.09 | 100.86 |
| Triton + amla seed extract 10 mg/Kg. | 55.4 | 38.76 | 10.24 | 18.13 |
| Triton + amla seed extract 7.5 mg/Kg. | 49.03 | 43.25 | 12.50 | 34.06 |
| Triton + amla seed extract 5 mg/Kg. | 46.68 | 47.85 | 9.12 | 24.08 |
| Triton + amla seed extract 2.5 mg/Kg. | 57.23 | 49.73 | 11.05 | 23.26 |
| Triton + amla seed extract 2 mg/Kg. | 47.9 | 56.17 | 9.90 | 21.11 |
| Triton + amla seed extract 1 mg/Kg. | 49.34 | 53.86 | 11.66 | 25.11 |
| Triton + amla seed extract 0.5 mg/Kg. | 53.31 | 54.75 | 11.09 | 24.45 |
| Triton + atorvastatin 10 mg/kg. | 47.75 | 60.23 | 7.98 | 20.77 |

Results indicated that intraperitoneal injection of triton significantly increased the total cholesterol level about 2 times over the baseline value. Similarly, triglyceride level also increased to very high level (Group II) following triton injection. Simultaneous oral administration of various doses of amla seed extract in triton injected rats lowered the cholesterol increase to almost normal level (Group III to IX). Triglyceride level was also lowered by all the doses of triton with amla seed extract as compared to triton alone group. The standard drug atorvastatin was also effective in lowering the cholesterol as well as triglyceride level (Group X). These results clearly indicate the hypolipidemic activity of amla seed extract at various dose levels in triton induced hyperlipidemia in rats.

Example 20

Hypolipidemic Activity of Amla Seed Extract Compared with Other Amla Extracts Using Triton WR 1339 Induced Dyslipidemia Model Forty eight male Albino rats (Sprague Dawley strain) weighing approximate 250-300 gm were selected for the study. The animals were kept in the animal house maintained at temp 24±2° C., 65% relative humidity and 12 hr light/dark cycle. The rats were acclimatized for two weeks and during this period they had access to standard pellet diet and water ad libitum. After two weeks of acclimatization, all the rats were fasted overnight before injecting Triton WR 1339

(Tyloxapol) and administration of test extracts/standard. The animals were divided into eight groups. Following treatment was given to overnight fasted rats:

Group I: Normal control (vehicle only).
Group II: Triton WR 1339 (300 mg/kg, intraperitoneal).
Group III: Triton WR 1339 (300 mg/kg, intraperitoneal) followed by amla seed extract prepared as per example 1 (2.5 mg/kg, per oral).
Group IV: Triton WR 1339 (300 mg/kg, intraperitoneal) followed by amla extract prepared as per example 3 (40 mg/kg, per oral).
Group V: Triton WR 1339 (300 mg/kg, intraperitoneal) followed by amla extract prepared as per example 4 (40 mg/kg, per oral).
Group VI: Triton WR 1339 (300 mg/kg, intraperitoneal) followed by amla extract prepared as per example 5 (40 mg/kg, per oral).
Group VII: Triton WR 1339 (300 mg/kg, intraperitoneal) followed by amla extract prepared as per example 6 (40 mg/kg, per oral).
Group VIII: Triton WR 1339 (300 mg/kg, intraperitoneal) followed by atorvastatin (10 mg/kg, per oral).

The animals were deprived of food for next 24 hours but had free access to water ad libitum. After 24 hour of drug treatment 2 ml blood samples were collected from the retro orbital plexus. The blood was allowed to clot and then centrifuged at 3000 rpm for 10 min and the serum was carefully drawn and collected into separate tubes. The serum was analyzed for total cholesterol, triglycerides, high density lipoproteins (HDL), low density lipoproteins (LDL) and very low density lipoproteins (VLDL) levels using auto-analyzer.

TABLE 3(A)

Lipid profile (mg/dl) of rats treated with Amla seed extract and Amla fruit extracts.

| Groups | TC Before | TC After | TG Before | TG After | HDL Before | HDL After |
|---|---|---|---|---|---|---|
| Normal control. | 95.52 | 99.36 | 42.38 | 48.51 | 31.02 | 32.11 |
| Triton only. | 102.52 | 348.87 | 61.51 | 614.21 | 41.90 | 51.22 |
| Triton + amla seed extract prepared as per example 1 (2.5 mg/Kg). | 108.22 | 112.23 | 61.23 | 95.88 | 39.46 | 47.51 |
| Triton + amla extract prepared as per example 3 (40 mg/kg). | 96.52 | 128.25 | 54.55 | 102.34 | 44.25 | 48.35 |
| Triton + amla extract prepared as per example 4 (40 mg/kg). | 108.24 | 124.55 | 59.32 | 115.36 | 41.26 | 46.52 |
| Triton + amla extract prepared as per example 5 (40 mg/kg). | 100.66 | 135.36 | 65.25 | 132.22 | 38.66 | 40.11 |
| Triton + amla extract prepared as per example 6 (40 mg/kg). | 97.56 | 132.66 | 60.21 | 125.54 | 34.59 | 36.54 |
| Triton + atorvastatin (10 mg/kg). | 97.33 | 132.58 | 48.99 | 218.66 | 35.11 | 33.84 |

TABLE 3(B)

Lipid profile (mg/dl) of rats treated with amla seed extract and amla fruit extracts.

| Groups | LDL Before | LDL After | VLDL Before | VLDL After |
|---|---|---|---|---|
| Normal control. | 56.03 | 57.54 | 8.47 | 9.70 |
| Triton only. | 48.32 | 174.80 | 12.30 | 122.84 |
| Triton + amla seed extract prepared as per example 1 (2.5 mg/Kg). | 56.52 | 45.55 | 12.24 | 19.17 |
| Triton + amla extract prepared as per example 3 (40 mg/kg). | 41.36 | 59.43 | 10.91 | 20.46 |
| Triton + amla extract prepared as per example 4 (40 mg/kg). | 55.11 | 54.95 | 11.86 | 23.07 |
| Triton + amla extract prepared as per example 5 (40 mg/kg). | 48.95 | 68.80 | 13.05 | 26.44 |
| Triton + amla extract prepared as per example 6 (40 mg/kg). | 50.92 | 71.01 | 12.04 | 25.10 |
| Triton + atorvastatin (10 mg/kg). | 52.43 | 55.00 | 9.79 | 43.73 |

In this study, effectiveness of amla seed extract (2.5 mg of extract/kg of subject) was compared with other amla extracts made as in Examples 3 to 6.

Results indicated that before treatment the baseline value of total cholesterol, triglyceride, HDL, LDL and VLDL in all groups were comparable. Injecting Triton alone (Group II) significantly increased the total cholesterol level to 348.87 mg/dl. Whereas in Group III, simultaneous oral administration of amla seed extract in triton injected rats, cholesterol level was 112.23 mg/dl which was 3.1 times lower as compared to triton alone group.

In group II triton injection increased the triglyceride level to 614.21 mg/dl. Whereas in Group III, simultaneous oral administration of amla seed extract in triton injected rats, triglyceride level was 95.88 mg/dl which was 6.4 times lower as compared to triton alone group.

In triton alone group after triton injection, the ratio of HDL to total cholesterol was 0.14. Whereas in Group III, simultaneous oral administration of amla seed extract in triton injected rats, the ratio of HDL cholesterol to total cholesterol was 0.42 which was 3 times higher as compared to triton alone group.

In group II triton injection increased the LDL level to 174.8 mg/dl. Whereas in Group III, simultaneous oral administration of amla seed extract in triton injected rats, LDL level was 45.55 mg/dl which was 3.8 times lower as compared to triton alone group.

In group II triton injection increased the VLDL level to 122.84 mg/dl. Whereas in Group III, simultaneous oral administration of amla seed extract in triton injected rats, VLDL level was 19.17 mg/dl which was 6.4 times lower as compared to triton alone group.

The other amla extracts (prepared in example 3 to 6) at 40 mg/kg were also able to decrease the cholesterol and triglyceride level but these were less effective than amla seed extract prepared in example 1. The standard drug Atorvastatin was also effective in lowering the cholesterol as well as triglyceride levels (Group VIII).

Example 21

Single Dosage Study for Evaluating Hypolipidemic Activity of Amla Seed Extract Compared with Other Amla Extracts Using Triton WR 1339 Induced Dyslipidemia Model Forty eight male Albino rats (Sprague Dawley strain) weighing approximate 250-300 gm were selected for the study. The animals were kept in the animal house maintained at temp 24±2° C., 65% relative humidity and 12 hr light/dark cycle. The rats were acclimatized for two weeks and during this period they had access to standard pellet diet and water ad libitum. After two weeks of acclimatization, all the rats were fasted overnight before injecting Triton WR 1339 (Tyloxapol) and administration of test extracts/standard. The animals were divided into eight groups. Following treatment was given to overnight fasted rats:

Group I: Normal control (vehicle only).

Group II: Triton WR 1339 (300 mg/kg, intraperitoneal).

Group III: Triton WR 1339 (300 mg/kg, intraperitoneal) followed by amla seed extract prepared as per example 1 (2.5 mg/kg, per oral).

Group IV: Triton WR 1339 (300 mg/kg, intraperitoneal) followed by amla extract prepared as per example 3 (2.5 mg/kg, per oral).

Group V: Triton WR 1339 (300 mg/kg, intraperitoneal) followed by amla extract prepared as per example 4 (2.5 mg/kg, per oral).

Group VI: Triton WR 1339 (300 mg/kg, intraperitoneal) followed by amla extract prepared as per example 5 (2.5 mg/kg, per oral).

Group VII: Triton WR 1339 (300 mg/kg, intraperitoneal) followed by amla extract prepared as per example 6 (2.5 mg/kg, per oral).

Group VIII: Triton WR 1339 (300 mg/kg, intraperitoneal) followed by atorvastatin (10 mg/kg, per oral).

The animals were deprived of food for next 24 hours but had free access to water ad libitum. After 24 hour of drug treatment 2 ml blood samples were collected from the retro orbital plexus. The blood was allowed to clot and then centrifuged at 3000 rpm for 10 min and the serum was carefully drawn and collected into separate tubes. The serum was analyzed for total cholesterol, triglycerides, high density lipoproteins (HDL), low density lipoproteins (LDL) and very low density lipoproteins (VLDL) levels using auto-analyzer.

TABLE 4(A)

Lipid profile (mg/dl) of rats treated with amla seed extract and amla fruit extracts in same dosage level

| Groups | TC Before | TC After | TG Before | TG After | HDL Before | HDL After |
|---|---|---|---|---|---|---|
| Normal control. | 102.25 | 101.56 | 56.33 | 54.96 | 39.65 | 42.51 |
| Triton only. | 91.55 | 385.54 | 55.69 | 644.65 | 44.52 | 59.54 |
| Triton + amla seed extract prepared as per example 1 (2.5 mg/Kg). | 94.66 | 108.25 | 60.23 | 111.36 | 38.41 | 46.23 |
| Triton + amla extract prepared as per example 3 (2.5 mg/kg). | 100.58 | 145.24 | 51.63 | 140.63 | 41.55 | 42.65 |
| Triton + amla extract prepared as per example 4 (2.5 mg/kg). | 106.52 | 139.66 | 49.36 | 131.33 | 42.36 | 46.31 |
| Triton + amla extract prepared as per example 5 (2.5 mg/kg). | 95.66 | 159.65 | 68.55 | 151.33 | 35.65 | 37.63 |
| Triton + amla extract prepared as per example 6 (2.5 mg/kg). | 98.69 | 152.36 | 67.96 | 148.65 | 37.55 | 39.54 |
| Triton + atorvastatin (10 mg/kg). | 99.83 | 122.54 | 46.59 | 211.06 | 39.51 | 36.66 |

TABLE 4(B)

Lipid profile (mg/dl) of rats treated with amla seed extract and amla fruit extracts in same dosage level.

| Groups | LDL Before | LDL After | VLDL Before | VLDL After |
|---|---|---|---|---|
| Normal control. | 51.33 | 48.06 | 11.26 | 10.99 |
| Triton only. | 35.89 | 197.07 | 11.13 | 128.93 |
| Triton + amla seed extract prepared as per example 1 (2.5 mg/Kg). | 44.20 | 39.75 | 12.04 | 22.27 |
| Triton + amla extract prepared as per example 3 (2.5 mg/kg). | 48.70 | 74.47 | 10.32 | 28.12 |
| Triton + amla extract prepared as per example 4 (2.5 mg/kg). | 54.28 | 67.09 | 9.87 | 26.26 |
| Triton + amla extract prepared as per example 5 (2.5 mg/kg). | 46.3 | 91.76 | 13.71 | 30.26 |
| Triton + amla extract prepared as per example 6 (2.5 mg/kg). | 47.54 | 83.09 | 13.59 | 29.73 |
| Triton + atorvastatin (10 mg/kg). | 51.00 | 43.67 | 9.31 | 42.21 |

In this study, amla seed extract (2.5 mg extract/kg of subject) was compared with other amla extracts made as in example 3 to 6 at the same dose level, i.e. 2.5 mg of extract/kg of subject.

Results indicated that before treatment the baseline value of total cholesterol, triglyceride, HDL, LDL and VLDL in all groups were comparable. Injecting Triton alone (Group II)

significantly increased the total cholesterol level to 385.54 mg/dl. Whereas in Group III, simultaneous oral administration of amla seed extract in triton injected rats, cholesterol level was 108.25 mg/dl which was 3.6 times lower as compared to triton alone group.

In group II triton injection increased the triglyceride level to 644.65 mg/dl. Whereas in Group III, simultaneous oral administration of amla seed extract in triton injected rats, triglyceride level was 111.36 mg/dl which was 5.8 times lower as compared to triton alone group.

In triton alone group after triton injection, the ratio of HDL to total cholesterol was 0.15. Whereas in Group III, simultaneous oral administration of amla seed extract in triton injected rats, the ratio of HDL cholesterol to total cholesterol was 0.42 which was 2.8 times higher as compared to triton alone group.

In group II triton injection increased the LDL level to 197.07 mg/dl. Whereas in Group III, simultaneous oral administration of amla seed extract in triton injected rats, LDL level was 39.75 mg/dl which was 4.9 times lower as compared to triton alone group.

In group II triton injection increased the VLDL level to 128.93 mg/dl. Whereas in Group III, simultaneous oral administration of amla seed extract in triton injected rats, VLDL level was 22.27 mg/dl which was 5.8 times lower as compared to triton alone group.

The other amla extracts (prepared in example 3 to 6) at 2.5 mg/kg were able to decrease the cholesterol and triglyceride level to a certain extent only but these are not as effective as amla seed extract at same dose levels. The studies carried out indicate that the standard drug Atorvastatin was effective in lowering the cholesterol as well as triglyceride levels (Group VIII) but less effective when compared with the amla seed extract.

Example 22

Antidiabetic Activity of Amla Seed Extract in Streptozotocin Induced Diabetic Rats The amla seed extract as prepared in example 1 was evaluated for antidiabetic activity in experimental rats. Male/Female albino wistar rats were maintained as per standard guidelines: housed in polypropylene cages, under 12 hour artificial light and dark cycles at a temperature of 24±2° C., given a standard pellet diet and water ad libitum. The animals were acclimatized to the animal house conditions for a week before beginning the experiment.

Diabetes was induced by injecting streptozotocin 35 mg/kg dissolved in 0.1M citrate buffer of pH 4.5, intraperitoneally. Five days after induction of diabetes (day 1 of the study), animals were fasted for 12 hours and the fasting blood glucose level (FBG) was estimated for diagnosing diabetic rats. Animals with FBG above 200 mg/dl were considered diabetic. The diabetic animals were randomly divided into three groups of six animals each.

Following table 5 shows the treatment schedule given to the respective group of animals for 28 days.

TABLE 5

Treatment schedule.

| Groups | Drugs administered |
|---|---|
| Group I | Vehicle for 28 days. |
| Group II | Glibenclamide (0.5 mg/kg) for 28 days. |
| Group III | Amla seed extract as per Example 1 (10 mg/kg) for 28 days. |

Fasting blood glucose level and body weight of rats was measured initially and then at Day 7, Day 14, Day 21 and Day 28 of the study. The plasma CRP level was measured initially and then at Day 28 of the study.

TABLE 6

Fasting blood glucose (FBG) level of diabetic rats treated with amla seed extract.

| | | Fasting Blood Glucose level (mg/dl) | | | | |
|---|---|---|---|---|---|---|
| Groups | Treatment | Day 1 (Initial) | Day 7 | Day 14 | Day 21 | Day 28 |
| Group I | Vehicle. | 355 | 382 | 391 | 411 | 431 |
| Group II | Glibenclamide. | 406 | 211 | 179 | 136 | 109 |
| Group III | Amla seed extract as per Example 1. | 369 | 266 | 211 | 172 | 135 |

TABLE 7

CRP level of diabetic rats treated with amla seed extract.

| | | CRP level (mg/L) | |
|---|---|---|---|
| Groups | Treatment | Day 1 (Initial) | Day 28 (Final) |
| Group I | Vehicle. | 10.3 | 11.3 |
| Group II | Glibenclamide. | 10.8 | 9.6 |
| Group III | Amla seed extract as per Example 1. | 9.9 | 6.3 |

As shown in the results, a single ip injection of streptozotocin increased the blood glucose level to very high level and made the rats diabetic. Treatment of diabetic rats with amla seed extract significantly lowered the blood glucose level in 28 days. That corresponds to a 2.7 times reduction in fasting blood glucose level in diabetic rats as compared to baseline (Day 1) after administration of amla seed extract for 28 days. Treatment with glibenclamide also decreased the blood glucose level to nearly normal in 28 days. Body weight of diabetic rats treated with amla seed extract recovered significantly as compared to vehicle group. The CRP level decreased significantly in amla seed extract fed group but glibenclamide failed to decrease the CRP level significantly as compared to initial CRP value. 28 days treatment with Amla seed extract to diabetic rats decreased the CRP level 1.6 times than initial level.

Example 23

Hypolipidemic Activity of Amla Seed Extract in Cholesterol Fed Rabbits

The amla seed extract as prepared in example 1 was evaluated for hypolipidemic activity in experimental rabbits. Male NZ white rabbits weighing 1.5-2.0 kg were used for the experiment. They were housed in a temperature-controlled room (25±2° C.) in clean stainless steel cages with '12 h light and 12 h dark' cycles and fed with normal pellet diet and water ad libitum.

After the acclimatization period of 10 days, blood samples were collected from marginal ear vein of all the rabbits. The blood was allowed to clot and then centrifuged at 3000 rpm for 10 min and the serum was carefully drawn and collected into separate tubes. The serum was analyzed for total cholesterol, triglycerides, high density lipoproteins (HDL), low density lipoproteins (LDL) and very low density lipoproteins (VLDL) levels using auto-analyzer.

After taking baseline lipid profile the animals were divided into four groups having six animals in each group. Following treatment was given to the animals for the three months:

TABLE 8

Treatment schedule.

| Groups | Drugs administered |
|---|---|
| Group I | Vehicle for 3 months. |
| Group II | Cholesterol (100 mg/kg) + Vehicle for 3 months. |
| Group III | Cholesterol (100 mg/kg) + Amla seed extract as per example 1 (10 mg/kg) for 3 months. |
| Group IV | Cholesterol (100 mg/kg) + Atorvastatin (10 mg/kg) for 3 months. |

Blood samples were collected from all the rabbits after 3 months of treatment and serum was analyzed for lipid profile. After blood collection the animals were sacrificed after injecting pentobarbitone and aorta was dissected out, washed with saline and preserved in 10% formalin for histopathology. The sections were cut using microtome and stained with heamatoxylin & eosin dye and mounted on glass slides. The slides were observed under microscope and aortic intima media thickness (IMT) was measured by histomorphometry.

TABLE 9 (A)

Lipid profile (mg/dl) of rabbits treated with amla seed extract.

| | TC | | TG | | HDL | |
|---|---|---|---|---|---|---|
| Groups | Before | After | Before | After | Before | After |
| Normal control (vehicle only). | 58.23 | 56.77 | 62.25 | 60.05 | 16.81 | 15.89 |
| Cholesterol + vehicle. | 54.88 | 219.81 | 59.26 | 188.25 | 14.58 | 11.5 |
| Cholesterol + amla seed extract. | 56.36 | 94.18 | 60.61 | 83.23 | 15.42 | 37.27 |
| Cholesterol + atorvastatin. | 53.69 | 118.9 | 58.28 | 78.67 | 14.15 | 20.37 |

TABLE 9 (B)

Lipid profile (mg/dl) of rabbits treated with amla seed extract.

| | LDL | | VLDL | |
|---|---|---|---|---|
| Groups | Before | After | Before | After |
| Normal control (vehicle only). | 28.97 | 28.37 | 12.45 | 12.01 |
| Cholesterol + vehicle. | 28.45 | 170.66 | 11.85 | 37.65 |
| Cholesterol + amla seed extract. | 28.82 | 40.26 | 12.12 | 16.65 |
| Cholesterol + atorvastatin. | 27.88 | 82.8 | 11.66 | 15.73 |

TABLE 10

Aortic intima media thickness (IMT) of rabbits treated with amla seed extract.

| Groups | Aortic intima media thickness (μm) |
|---|---|
| Normal control (vehicle only). | 49.52 |
| Cholesterol + vehicle. | 123.24 |
| Cholesterol + amla seed extract. | 66.21 |
| Cholesterol + atorvastatin. | 112.36 |

Results show that, before treatment the baseline value of total cholesterol, triglyceride, HDL, LDL and VLDL in all groups were comparable. Feeding cholesterol for three months increased the total cholesterol and triglyceride levels to very high.

Administration of Cholesterol alone (Group II) significantly increased the total cholesterol level to 219.81 mg/dl. Whereas in Group III, oral administration of cholesterol+ amla seed extract, total cholesterol level was 94.18 mg/dl which was 2.3 times lower as compared to cholesterol alone group.

In group II cholesterol administration increased the triglyceride level to 188.25 mg/dl. Whereas in Group III, oral administration of cholesterol+ amla seed extract, triglyceride level was 83.23 mg/dl which was 2.3 times lower as compared to cholesterol alone group.

In group III, administration of cholesterol+ amla seed extract increased the HDL (good cholesterol) level significantly from a baseline value of 15.42 to 37.27 after 3 months treatment. That was a 2.4 times increase in the HDL cholesterol after 3 month treatment.

After cholesterol administration the cholesterol alone group showed a ratio of HDL to total cholesterol was 0.05. Whereas in Group III, oral administration of cholesterol+ amla seed extract, the ratio of HDL cholesterol to total cholesterol was 0.39 which was 7.8 times higher as compared to cholesterol alone group.

In group II administration of cholesterol alone increased the LDL level to 170.66 mg/dl. Whereas in Group III, oral administration of cholesterol+ amla seed extract, LDL level was 40.26 mg/dl which was 4.2 times lower as compared to triton alone group.

In group II administration of cholesterol alone increased the VLDL level to 37.65 mg/dl. Whereas in Group III, oral administration of cholesterol+ amla seed extract, VLDL level was 16.65 mg/dl which was 2.3 times lower as compared to cholesterol alone group.

Atorvastatin also decreased the total cholesterol and triglyceride level significantly as compared to untreated control group but amla seed extract was better especially in increasing the HDL level.

Moreover, administration of amla seed extract showed a 1.9 times reduction in the intima media thickness of aorta of rabbits as compared to untreated control group.

Example 24

Hair Fall Prevention and Hair Growth Promoting Activity of Amla Seed Extract in Humans Method:

10 human subjects suffering with alopecia and severe hair fall (as detected by a dermatologist) were randomly divided into two groups having 5 subjects in each group.

Group I—Amla seed extract group prepared as per example 1.
Group II—Placebo group.

All the subjects were prohibited to take any kind of medicines (oral or topical) having hair growth promotion like minoxidil, finasteride etc. for one month prior to the study initiation. The subjects of group I applied 5 ml coconut oil containing 5% amla seed extract twice daily on the affected area and also took 100 mg of amla seed extract capsules twice daily. The subjects of placebo group were given coconut oil (without amla seed extract) to be applied twice daily on affected area and were provided with placebo capsules to be taken twice daily. The treatment was continued for 3 months and observations were taken by a dermatologist before and after the study period. Length and thickness of randomly plucked five hairs from each subject was also determined.

Results:

The hairs of subjects treated with amla seed extract were shiny, lustrous and denser as compared to placebo group. The hair fall was almost arrested in the subjects treated with amla seed extract. In contrast, the subjects of placebo group observed hair fall at the same rate as it was before starting the treatment. The average length of hairs of subjects treated with amla seed extract was about 25% more than the subjects of placebo group. Thickness of the hairs was also about 20% more in amla seed extract group as compared to subjects in placebo group. Therefore, amla seed extract was helpful in decreasing the hair fall as well as in promoting hair growth. Amla seed extract also made the hairs lustrous and shiny.

Example 25

Hypolipidemic Activity of Amla Seed Extract Compared with Other Amla Extracts Using Triton WR 1339 Induced Dyslipidemia Model Forty eight male Albino rats (Sprague Dawley strain) weighing approximate 250-300 gm were selected for the study. The animals were kept in the animal house maintained at temp 24±2° C., 65% relative humidity and 12 hr light/dark cycle. The rats were acclimatized for two weeks and during this period they had access to standard pellet diet and water ad libitum. After two weeks of acclimatization, all the rats were fasted overnight before injecting Triton WR 1339 (Tyloxapol) and administration of test extracts/standard. The animals were divided into twelve groups. Following treatment was given to overnight fasted rats:
Group I: Normal control (vehicle only).
Group II: Triton WR 1339 (300 mg/kg, intraperitoneal).
Group III: Triton WR 1339 (300 mg/kg, intraperitoneal) followed by ethyl acetate of methanol extract of amla seed prepared as per example 1 (2.5 mg/kg, per oral).
Group IV: Triton WR 1339 (300 mg/kg, intraperitoneal) followed by water part of methanol extract of amla seed prepared as per example 1 (2.5 mg/kg, per oral).
Group V: Triton WR 1339 (300 mg/kg, intraperitoneal) followed by ethyl acetate extract of amla seed prepared as per example 2 (2.5 mg/kg, per oral).
Group VI: Triton WR 1339 (300 mg/kg, intraperitoneal) followed by powder of dried amla seed prepared as per example 7 (2.5 mg/kg, per oral).
Group VII: Triton WR 1339 (300 mg/kg, intraperitoneal) followed by water extract of dried amla seed powder prepared as per example 8 (2.5 mg/kg, per oral).
Group VIII: Triton WR 1339 (300 mg/kg, intraperitoneal) followed by methanol extract of dried amla seed powder prepared as per example 9 (2.5 mg/kg, per oral).
Group IX: Triton WR 1339 (300 mg/kg, intraperitoneal) followed by powder of dried amla fruit prepared as per example 10 (2.5 mg/kg, per oral).
Group X: Triton WR 1339 (300 mg/kg, intraperitoneal) followed by water extract of dried Amla fruit powder prepared as per example 11 (2.5 mg/kg, per oral).
Group XI: Triton WR 1339 (300 mg/kg, intraperitoneal) followed by methanol extract of dried amla fruit powder prepared as per example 12 (2.5 mg/kg, per oral).
Group XII: Triton WR 1339 (300 mg/kg, intraperitoneal) followed by atorvastatin (2.5 mg/kg, per oral).

The animals were deprived of food for next 24 hours but had free access to water ad libitum. After 24 hour of drug treatment 2 ml blood samples were collected from the retro orbital plexus. The blood was allowed to clot and then centrifuged at 3000 rpm for 10 min and the serum was carefully drawn and collected into separate tubes. The serum was analyzed for total cholesterol, triglycerides, high density lipoproteins (HDL), low density lipoproteins (LDL) and very low density lipoproteins (VLDL) levels using autoanalyzer.

TABLE 11(A)

Lipid profile (mg/dl) of rats treated with amla seed extract and amla fruit extracts in same dosage level.

| Groups | TC | | TG | | HDL | |
| --- | --- | --- | --- | --- | --- | --- |
| | Before | After | Before | After | Before | After |
| Normal control. | 90.15 | 94.16 | 58.18 | 61.65 | 30.12 | 31.01 |
| Triton only. | 98.92 | 288.18 | 60.15 | 581.42 | 35.59 | 42.62 |
| Triton + EtOAc extract amla seed prepared as per example 1 (2.5 mg/Kg). | 101.12 | 106.41 | 62.42 | 90.47 | 34.14 | 48.15 |
| Triton + water part of amla seed prepared as per example 1 (2.5 mg/kg). | 102.54 | 266.25 | 54.57 | 556.35 | 32.24 | 37.54 |
| Triton + EtOAc extract of amla seed prepared as per example 2 (2.5 mg/kg). | 99.35 | 122.25 | 55.87 | 99.5 | 36.25 | 42.51 |
| Triton + powder of dried amla seed prepared as per example 7 (2.5 mg/kg). | 97.54 | 275.56 | 58.65 | 541.35 | 31.25 | 36.65 |

TABLE 11(A)-continued

Lipid profile (mg/dl) of rats treated with amla seed extract and amla fruit extracts in same dosage level.

| Groups | TC Before | TC After | TG Before | TG After | HDL Before | HDL After |
|---|---|---|---|---|---|---|
| Triton + water extract of amla seed powder prepared as per example 8 (2.5 mg/kg). | 89.2 | 257.6 | 46 | 548 | 31 | 34 |
| Triton + methanol extract of amla seed powder prepared as per example 9 (2.5 mg/kg). | 96.55 | 251.64 | 55.69 | 552.36 | 35.68 | 39.41 |
| Triton + powder of dried amla fruit prepared as per example 10 (2.5 mg/kg). | 95.64 | 253.14 | 59.68 | 575.36 | 33.54 | 37.74 |
| Triton + water extract of amla fruit powder prepared as per example 11 (2.5 mg/kg). | 101.22 | 265.33 | 59.85 | 547.96 | 31.54 | 41.52 |
| Triton + methanol extract of amla seed powder prepared as per example 12 (2.5 mg/kg). | 99.64 | 254.39 | 60.77 | 577.63 | 34.88 | 40.57 |
| Triton + Atorvastatin (2.5 mg/kg). | 104.44 | 123.14 | 49.54 | 195.25 | 36.54 | 39.56 |

TABLE 11(B)

Lipid profile (mg/dl) of rats treated with amla seed extract and amla fruit extracts in same dosage level.

| Groups | LDL Before | LDL After | VLDL Before | VLDL After |
|---|---|---|---|---|
| Normal control. | 48.39 | 50.82 | 11.64 | 12.33 |
| Triton only. | 51.3 | 129.28 | 12.03 | 116.28 |
| Triton + EtOAc extract amla seed prepared as per example 1 (2.5 mg/Kg). | 54.5 | 40.17 | 12.48 | 18.09 |
| Triton + water part of amla seed prepared as per example 1 (2.5 mg/kg). | 59.39 | 117.44 | 10.91 | 111.27 |
| Triton + EtOAc extract of amla seed prepared as per example 2 (2.5 mg/kg). | 51.93 | 59.84 | 11.17 | 19.9 |
| Triton + powder of dried amla seed prepared as per example 7 (2.5 mg/kg). | 54.56 | 130.64 | 11.73 | 108.27 |
| Triton + water extract of amla seed powder prepared as per example 8 (2.5 mg/kg). | 59.16 | 131.86 | 12.25 | 114.29 |
| Triton + methanol extract of amla seed powder prepared as per example 9 (2.5 mg/kg). | 49.73 | 101.76 | 11.14 | 110.47 |
| Triton + powder of dried amla fruit prepared as per example10 (2.5 mg/kg). | 50.16 | 100.33 | 11.94 | 115.07 |
| Triton + water extract of amla fruit powder prepared as per example 11 (2.5 mg/kg). | 57.71 | 114.22 | 11.97 | 109.59 |
| Triton + methanol extract of amla seed powder prepared as per example 12 (2.5 mg/kg). | 52.61 | 98.29 | 12.15 | 115.53 |
| Triton + Atorvastatin (2.5 mg/kg). | 57.99 | 44.53 | 9.91 | 39.05 |

In this study, amla seed extract (2.5 mg extract/kg body weight) made in example 1 and 2 were compared with other amla extracts made as in example 7 to 12 at the same dose level, i.e. 2.5 mg of extract/kg body weight.

Results show that, before treatment the baseline value of total cholesterol, triglyceride, HDL, LDL and VLDL in all groups were comparable.

Injecting Triton alone (Group II) significantly increased the total cholesterol level to 288.18 mg/dl. Whereas in Group III, simultaneous oral administration of amla seed extract prepared as per example 1 in triton injected rats, cholesterol level was 106.41 mg/dl which was 2.7 times lower as compared to triton alone group.

In group II triton injection increased the triglyceride level to 581.42 mg/dl. Whereas in Group III, simultaneous oral administration of amla seed extract prepared as per Example 1 in triton injected rats, triglyceride level was 90.47 mg/dl which was 6.4 times lower as compared to triton alone group.

In triton alone group after triton injection the ratio of HDL to total cholesterol was 0.15. Whereas in Group III, simultaneous oral administration of amla seed extract prepared as per example 1 in triton injected rats, the ratio of HDL cholesterol to total cholesterol was 0.45 which was 3 times higher as compared to triton alone group.

In group II triton injection increased the LDL level to 129.28 mg/dl. Whereas in Group III, simultaneous oral administration of amla seed extract (prepares as per example 1) in triton injected rats, LDL level was 40.17 mg/dl which was 3.2 times lower as compared to triton alone group.

In group II triton injection increased the VLDL level to 116.28 mg/dl. Whereas in Group III, simultaneous oral administration of amla seed extract (prepared as per example 1) in triton injected rats, VLDL level was 18.09 mg/dl which was 6.4 times lower as compared to triton alone group.

The ethyl acetate extract of amla seeds (prepared in example 2) at 2.5 mg/kg were also able to decrease the cholesterol and triglyceride level to a certain extent (Group V).

Results show that, before treatment the baseline value of total cholesterol, triglyceride, HDL, LDL and VLDL in all groups were comparable.

Injecting Triton alone (Group II) significantly increased the total cholesterol level to 288.18 mg/dl. Whereas in Group III, simultaneous oral administration of amla seed extract prepared as per example 2 in triton injected rats, cholesterol level was 122.25 mg/dl which was 2.3 times lower as compared to triton alone group.

In group II triton injection increased the triglyceride level to 581.42 mg/dl. Whereas in Group III, simultaneous oral administration of amla seed extract prepared as per Example 2 in triton injected rats, triglyceride level was 99.5 mg/dl which was 5.8 times lower as compared to triton alone group.

In triton alone group after injection the ratio of HDL to total cholesterol was 0.15. Whereas in Group III, simultaneous oral administration of amla seed extract prepared as per example 2 in triton injected rats, the ratio of HDL cholesterol to total cholesterol was 0.35 which was 2.3 times higher as compared to triton alone group.

In group II triton injection increased the LDL level to 129.28 mg/dl. Whereas in Group III, simultaneous oral administration of amla seed extract (prepares as per example 2) in triton injected rats, LDL level was 59.84 mg/dl which was 2.1 times lower as compared to triton alone group.

In group II triton injection increased the VLDL level to 116.28 mg/dl. Whereas in Group III, simultaneous oral administration of amla seed extract (prepared as per example 2) in triton injected rats, VLDL level was 19.9 mg/dl which was 5.8 times lower as compared to triton alone group.

The water part of methanol extract (prepared in example 1), amla seed powder and other water and methanol extracts (prepared in example 7 to 12) were not active in reducing cholesterol or triglyceride levels. Though the standard drug atorvastatin was effective in lowering the cholesterol as well as triglyceride levels (Group XII) but less effective when compared with the ethyl acetate part of amla seed methanol extract (as per example 1) or ethyl acetate extract of amla seeds (as per example 2).

Example 26

Hypolipidemic Activity of Amla Seed Extract (Product 3) Compared with Amla Seed Powder Using Triton WR 1339 Induced Dyslipidemia Model Twenty eight male Albino rats (Sprague Dawley strain) weighing approximately 250-300 gm were selected for the study. The animals were maintained at temperature of 24±2° C., 65% relative humidity and 12 hr light/dark cycle. The rats were acclimatized for two weeks and during this period they had access to standard pellet diet and water ad libitum. After two weeks of acclimatization, all the rats were fasted overnight before injecting Triton WR 1339 (Tyloxapol) and administration of test extracts/standard. The animals were divided into seven groups. Following treatment was given to overnight fasted rats:

Group I: Normal control (vehicle only)
Group II: Triton WR 1339 (300 mg/kg, intraperitoneal)
Group III: Triton WR 1339 (300 mg/kg, intraperitoneal) followed by administering product of amla seed extract (product 3) on the same day of triton administration (0.5 mg/kg, per oral)
Group IV: Triton WR 1339 (300 mg/kg, intraperitoneal) followed by product 2 (50% methanol fraction+ 80% methanol fraction+ water fraction) of amla seed extract on the same day that Triton was administered (0.5 mg/kg, per oral)
Group V: Triton WR 1339 (300 mg/kg, intraperitoneal) followed by product 1 (Hexane fraction) of amla seed extract on the same day that Triton was administered (0.5 mg/kg, per oral)
Group VI: Triton WR 1339 (300 mg/kg, intraperitoneal) followed by powder of dried amla seed prepared as per Example 7 (0.5 mg/kg, per oral). The powder of dried amla seed was administered on the same day as triton was administered.
Group VII: Triton WR 1339 (300 mg/kg, intraperitoneal) followed by atorvastatin administration (10 mg/kg, per oral), on the same day.

The animals were deprived of food for next 24 hours but had free access to water ad libitum. After 24 hours of drug treatment, 2 ml of blood sample was collected from the retro orbital plexus. The blood was allowed to clot and then centrifuged at 3000 rpm for 10 min and the serum was carefully drawn and collected into separate tubes. The serum was analyzed for total cholesterol, triglycerides, high density lipoproteins (HDL), low density lipoproteins (LDL) and very low density lipoproteins (VLDL) levels using autoanalyzer.

TABLE 12(A)

Lipid profile (mg/dl) of rats treated with amla seed extracts (product 3) and different fractions (product 1 and product 2).

| | TC | | TG | | HDL | |
|---|---|---|---|---|---|---|
| Groups | Before | After | Before | After | Before | After |
| Group I Normal control. | 91.05 | 95.11 | 57.16 | 60.47 | 29.31 | 30.11 |
| Group II Triton only. | 109.55 | 386.4 | 49.5 | 583.33 | 32.5 | 43.2 |
| Group III Triton + amla seed product 3 (0.5 mg/Kg). | 90.2 | 95.6 | 44.66 | 62.4 | 28.78 | 49.36 |

TABLE 12(A)-continued

Lipid profile (mg/dl) of rats treated with amla seed extracts (product 3) and different fractions (product 1 and product 2).

| Groups | TC Before | TC After | TG Before | TG After | HDL Before | HDL After |
|---|---|---|---|---|---|---|
| Group IV Triton + amla seed product 2 (0.5 mg/Kg). | 96.5 | 132.36 | 46.8 | 103.5 | 27.4 | 41.03 |
| Group V Triton + amla seed product 1 (0.5 mg/Kg). | 95.7 | 184.5 | 50.12 | 119.4 | 30.9 | 47.97 |
| Group VI Triton + powder of dried amla seed prepared as per Example 7 (0.5 mg/kg). | 96.85 | 345.6 | 59.65 | 542.54 | 32.35 | 34.45 |
| Group VII Triton + atoryastatin (10 mg/kg). | 103.47 | 121.21 | 48.54 | 192.25 | 35.54 | 38.46 |

TABLE 12(B)

Lipid profile (mg/dl) of rats treated with Amla seed extracts (product 3) and different fractions (Product 1 and product 2).

| Groups | LDL Before | LDL After | VLDL Before | VLDL After |
|---|---|---|---|---|
| Group I Normal control | 50.31 | 52.91 | 50.31 | 52.91 |
| Group II Triton only | 67.15 | 226.53 | 67.15 | 226.53 |
| Group III Triton + amla seed product 3 (0.5 mg/Kg) | 60.81 | 33.76 | 60.81 | 33.76 |
| Group IV Triton + amla seed product 2 (0.5 mg/Kg) | 62.3 | 70.63 | 62.3 | 70.63 |
| Group V Triton + amla seed product 1 (0.5 mg/Kg) | 65.4 | 112.65 | 65.4 | 112.65 |
| Group VI Triton + powder of dried amla seed prepared as per example 7 (0.5 mg/kg) | 52.57 | 202.64 | 52.57 | 202.64 |
| Group VII Triton + atorvastatin (10 mg/kg) | 58.22 | 44.30 | 58.22 | 44.30 |

Injecting Triton alone (Group II) significantly increased the total cholesterol level to 386.4 mg/dl. Whereas in Group III, following oral administration of product 3 of amla seed extract to triton injected rats, the cholesterol level was 95.6 mg/dl. Therefore, administering product 3 (Group III) resulted in 4 times lower level of cholesterol as compared to triton alone treatment (Group II).

In Group II triton injection increased the triglyceride level to 583.33 mg/dl. Whereas in Group III, oral administration of product 3 to triton injected rats, the triglyceride level was 62.4 mg/dl, which was 9.3 times lower as compared to triton alone group (Group 2).

In triton alone group after triton injection the ratio of HDL to total cholesterol was 0.11. Whereas in Group III, the ratio of HDL cholesterol to total cholesterol was 0.51, which was 4.6 times higher as compared to triton alone group.

In group II triton injection increased the LDL level to 226.53 mg/dl. Whereas in Group III, LDL level was 33.76 mg/dl, which was 6.7 times lower as compared to triton alone group.

In group II triton injection increased the VLDL level to 116.67 mg/dl. Whereas in Group III, the VLDL level was 12.48 mg/dl, which was 9.3 times lower as compared to triton alone group.

Injecting Triton alone (Group II) significantly increased the total cholesterol level to 386.4 mg/dl. Whereas in Group IV (Triton followed by Product 2 administration), cholesterol level was 132.36 mg/dl, which was 2.9 times lower as compared to triton alone group.

In Group II Triton injection increased the triglyceride level to 583.33 mg/dl. Whereas in Group IV, oral administration of product 2 to triton injected rats, triglyceride level was 103.5 mg/dl, which was 5.6 times lower as compared to triton alone group.

In triton alone group after triton injection the ratio of HDL to total cholesterol was 0.11. Whereas in Group IV, oral administration of amla seed extract (product 2) to triton injected rats, the ratio of HDL cholesterol to total cholesterol was 0.30 which was 2.7 times higher as compared to triton alone group.

In Group II, Triton injection increased the LDL level to 226.53 mg/dl. Whereas in Group IV, oral administration of product 2 to triton injected rats, LDL level was 70.63 mg/dl, which was 3.2 times lower as compared to triton alone group.

In Group II, triton injection increased the VLDL level to 116.67 mg/dl. Whereas in Group IV, oral administration of product 2 to triton injected rats, VLDL level was 20.7 mg/dl, which was 5.6 times lower as compared to triton alone group (Group II).

Injecting Triton alone (Group II) significantly increased the total cholesterol level to 386.4 mg/dl. Whereas in Group V, simultaneous oral administration of product 1 prepared as per example 13 in triton injected rats, cholesterol level was 184.5 mg/dl which was 2.09 times lower as compared to triton alone group.

In group II triton injection increased the triglyceride level to 583.33 mg/dl. Whereas in Group V, simultaneous oral administration of product 1 in triton injected rats, triglyceride level was 119.4 mg/dl which was 4.9 times lower as compared to triton alone group.

In triton alone group after injection the ratio of HDL to total cholesterol was 0.11. Whereas in Group V, simultaneous oral administration of product 1 prepared as per example 13 in triton injected rats, the ratio of HDL cholesterol to total cholesterol was 0.26 which was 2.4 times higher as compared to triton alone group.

In group II triton injection increased the LDL level to 226.53 mg/dl. Whereas in Group V, simultaneous oral administration of product 1 prepared as per example 13 in triton injected rats, LDL level was 112.65 mg/dl which was 2 times lower as compared to triton alone group.

In group II triton injection increased the VLDL level to 116.67 mg/dl. Whereas in Group V, simultaneous oral administration of product 1 prepared as per example 13 in triton injected rats, VLDL level was 23.88 mg/dl which was 4.9 times lower as compared to triton alone group.

Example 27

Method of Preparation of Extract of Seed of *Emblica officinalis* Enriched with Triterpenoids 500 Kg of fresh fruits of *Emblica officinalis* (Amla) were collected. Fruits were deseeded by deseeding machine and 75 Kg of fresh seeds were crushed through roller mill. 95% Methanol in an amount 2 times the quantity of crushed seeds was added to the crushed seeds to form a mixture for methanol extraction. The extraction was performed using an extractor with reflux condenser. The bottom of the extractor was fitted with a polypropylene (100 microns) filter cloth. The mixture was refluxed for one hour at 65° C. to obtain a residue and a first supernatant. The residue and the first supernatant were separated by draining out the supernatant from the extractor bottom through the polypropylene filter cloth using a centrifugal pump. After the first extraction, the remaining residue was further extracted with two times the quantity of methanol at 65° C. to again obtain a residue and a second supernatant. This residue was further extracted with two times the quantity of methanol at 65° C. to obtain another residue and a third supernatant. The first, second and third supernatants were pooled and the resulting mixture was concentrated in an Agitated thin film evaporator (ATFE) at a temperature of 65° C. to form a concentrated methanol extract. The concentrated methanol extract was dried under vacuum at above 500 mm of mercury to obtain 5 kg of powder. This powder is referred to as methanol extract powder of seed of *Emblica officinalis*.

The methanol extract powder of seed of *Emblica officinalis* was macerated with water and transferred into a liquid-liquid extractor and extracted with ethyl acetate. Ethyl acetate phase and aqueous phase were separated. After extraction ethyl acetate phase was collected. Ethyl acetate phase was concentrated in an Agitated thin film evaporator to form concentrated ethyl acetate extract. Ethyl acetate concentrate was fed into vacuum stripper and dried under vacuum at above 500 mm of mercury to obtain 2.5 kg of powder. This powder is referred to as ethyl acetate extract powder from methanol extract powder of seed of *Emblica Officinalis*.

50% Methanol (10 L) was added to 2.5 kg of ethyl acetate extract powder from methanol extract powder of seed of *Emblica officinalis* to form a mixture for methanol extraction. The extraction was performed using an extractor with reflux condenser. After refluxing the oil part formed was separated from the methanol-water part. Oil part was discarded and methanol-water part was concentrated to form concentrated methanol part with a yield of 1.8 Kg.

Concentrated methanol-water part was loaded on a HP20 column. Column was eluted with ethyl acetate and 100% methanol. Each fraction was collected and concentrated. Concentrated methanol fraction was dried under vacuum to form powder of seed of *Emblica officinalis* with a yield of 0.8 kg. This powder was referred to as Sample 1. Sample 1 was found to have about 63.5% triterpenoids and about 27% hydroxycinnamic acids.

A blend was prepared with Sample 1 as the first extract of seed of *Emblica officinalis* and a second extract of amla seed (also referred to as product 1) which was attained by the method of Example 13. A method of preparing the first extract of seeds of *Emblica officinalis* is provided in FIG. 14A. Method for preparing second extract of amla seed and blend of the first and second extract of seeds of *Emblica officinalis* is provided in FIG. 14B.

0.8 Kg of powder of seed of *Emblica officinalis* (sample 1) was combined with 0.8 Kg of product 1 prepared in example 13 in a 1:1 ratio to form an amla seed blend with a yield of 1.6 Kg. The blend is also referred to as Sample 2.

Sample 2 had about 32% triterpenoids, about 13.5% hydroxycinnamic acids, about 38.6% unsaturated fatty acids and about 0.3% saturated fatty acids.

Example 28

Hypolipidemic Activity of Enriched Amla Seed Extract Compared with Other Amla Extract Using Triton WR 1339 Induced Dyslipidemia Model Fifty two male Albino rats (Sprague Dawley strain) weighing approximately 250-300 gm were selected for the study. The animals were maintained at temperature of 24±2° C., 65% relative humidity and 12 hr light/dark cycle. The rats were acclimatized for two weeks and during this period they had access to standard pellet diet and water ad libitum. After two weeks of acclimatization, all the rats were fasted overnight before injecting Triton WR 1339 (Tyloxapol) and administration of test extracts/standard. The animals were divided into thirteen groups. Following treatment was given to overnight fasted rats:

Group I: Normal control (vehicle only).
Group II: Triton WR 1339 (300 mg/kg, intraperitoneal).
Group III: Triton WR 1339 (300 mg/kg, intraperitoneal) followed by administering sample 1 of Amla seed extract prepared as per example 27 on the same day of triton administration (0.5 mg/kg, per oral).
Group IV: Triton WR 1339 (300 mg/kg, intraperitoneal) followed by Amla seed extract prepared as per example 1 (0.5 mg/kg, per oral).
Group V: Triton WR 1339 (300 mg/kg, intraperitoneal) followed by sample 2 which is a 1:1 combination of amla seed extract (sample 1) prepared as per example 27 and product 1 (Hexane fraction) of amla seed extract prepared as per example 13 on the same day that Triton was administered (0.5 mg/kg, per oral).
Group VI: Triton WR 1339 (300 mg/kg, intraperitoneal) followed by administering product of amla seed extract (product 3) prepared as per example 13 on the same day of triton administration (0.5 mg/kg, per oral).
Group VII: Triton WR 1339 (300 mg/kg, intraperitoneal) followed by product 2 (50% methanol fraction+ 80% methanol fraction+ water fraction) of amla seed extract prepared as per example 13 on the same day that triton was administered (0.5 mg/kg, per oral).
Group VIII: Triton WR 1339 (300 mg/kg, intraperitoneal) followed by product 1 (hexane fraction) of amla seed extract prepared as per example 13 on the same day that triton was administered (0.5 mg/kg, per oral).
Group IX: Triton WR 1339 (300 mg/kg, intraperitoneal) followed by water extract of dried amla seed powder prepared as per example 8 (0.5 mg/kg, per oral).

Group X: Triton WR 1339 (300 mg/kg, intraperitoneal) followed by methanol extract of dried amla seed powder prepared as per example 9 (0.5 mg/kg, per oral).

Group XI: Triton WR 1339 (300 mg/kg, intraperitoneal) followed by water extract of dried amla fruit powder prepared as per example 11 (0.5 mg/kg, per oral).

Group XII: Triton WR 1339 (300 mg/kg, intraperitoneal) followed by methanol extract of dried amla fruit powder prepared as per example 12 (0.5 mg/kg, per oral).

Group XIII: Triton WR 1339 (300 mg/kg, intraperitoneal) followed by atorvastatin administration (10 mg/kg, per oral), on the same day.

The animals were deprived of food for next 24 hours but had free access to water ad libitum. After 24 hours of drug treatment, 2 ml of blood sample was collected from the retro orbital plexus. The blood was allowed to clot and then centrifuged at 3000 rpm for 10 min and the serum was carefully drawn and collected into separate tubes. The serum was analyzed for total cholesterol, triglycerides, high density lipoproteins (HDL), low density lipoproteins (LDL) and very low density lipoproteins (VLDL) levels using auto-analyzer.

TABLE 13(A)

Lipid profile (mg/dl) of rats treated with different Amla seed extracts.

| Groups | TC Before | TC After | TG Before | TG After | HDL Before | HDL After |
|---|---|---|---|---|---|---|
| Group I Normal control | 90.6 | 94.4 | 55 | 61 | 31.9 | 30.5 |
| Group II Triton only | 100.32 | 397.4 | 47.6 | 545 | 30.5 | 41.8 |
| Group III Triton + Amla seed sample 1 (0.5 mg/Kg) | 82.04 | 97.98 | 49.2 | 104.9 | 30.2 | 43.2 |
| Group IV Triton + Amla seed extract prepared as per example 1 (0.5 mg/Kg) | 94.76 | 116.06 | 50.3 | 125.3 | 29.3 | 39 |
| Group V Triton + Amla seed (sample 2) (0.5 mg/Kg) | 91.44 | 91.1 | 48.2 | 64.5 | 30.1 | 48.5 |
| Group VI Triton + Amla seed (produc t3) (0.5 mg/kg) | 90.46 | 97 | 46.8 | 70 | 29.6 | 46 |
| Group VII Triton + Amla seed (product 2) (0.5 mg/kg) | 95.64 | 134.55 | 47.2 | 109.8 | 27.2 | 37.09 |
| Group VIII Triton + Amla seed (product 1) (0.5 mg/kg) | 93.58 | 251.8 | 47.9 | 124 | 28 | 32 |
| Group IX Triton + water extract of dried Amla seed powder (0.5 mg/kg). | 89.2 | 257.6 | 46 | 548 | 31 | 34 |
| Group X Triton + methanol extract of dried Amla seed powder (0.5 mg/kg). | 92.6 | 245.2 | 43.1 | 521 | 33 | 35 |
| Group XI Triton + water extract of dried Amla fruit powder (0.5 mg/kg). | 87.8 | 240.2 | 43 | 546 | 27.2 | 31 |
| Group XII Triton + methanol extract of dried Amla fruit powder (0.5 mg/kg). | 90.4 | 248.8 | 42 | 559 | 29 | 33 |
| Group XIII Triton + Atorvastatin (10 mg/kg) | 104.21 | 124.54 | 50.54 | 200.25 | 32.41 | 35.1 |

TABLE 13(B)

Lipid profile (mg/dl) of rats treated with different Amla seed extracts.

| Groups | LDL Before | LDL After | VLDL Before | VLDL After |
|---|---|---|---|---|
| Group I Normal control | 47.7 | 51.7 | 11 | 12.2 |
| Group II Triton only | 60.3 | 246.6 | 9.52 | 109 |

TABLE 13(B)-continued

Lipid profile (mg/dl) of rats treated with different Amla seed extracts.

| Groups | LDL Before | LDL After | VLDL Before | VLDL After |
|---|---|---|---|---|
| Group III<br>Triton + Amla seed sample 1 (0.5 mg/Kg) | 42 | 33.8 | 9.84 | 20.98 |
| Group IV<br>Triton + Amla seed extract prepared as per example 1 (0.5 mg/Kg) | 55.4 | 52 | 10.06 | 25.06 |
| Group V<br>Triton + Amla seed sample 2 (0.5 mg/Kg) | 51.7 | 29.7 | 9.64 | 12.9 |
| Group VI<br>Triton + Amla seed (product 3) (0.5 mg/kg) | 51.5 | 37 | 9.36 | 14 |
| Group VII<br>Triton + Amla seed (product 2) (0.5 mg/kg) | 59 | 75.5 | 9.44 | 21.96 |
| Group VIII<br>Triton + Amla seed (product 1) (0.5 mg/kg) | 56 | 195 | 9.58 | 24.8 |
| Group IX<br>Triton + water extract of dried Amla seed powder (0.5 mg/kg). | 49 | 114 | 9.2 | 109.6 |
| Group X<br>Triton + methanol extract of dried Amla seed powder (0.5 mg/kg). | 51 | 106 | 8.6 | 104.2 |
| Group XI<br>Triton + water extract of dried Amla fruit powder (0.5 mg/kg). | 52 | 100 | 8.6 | 109.2 |
| Group XII<br>Triton + methanol extract of dried Amla fruit powder (0.5 mg/kg). | 53 | 104 | 8.4 | 111.8 |
| Group XIII<br>Triton + Atorvastatin (10 mg/kg) | 61.7 | 49.39 | 10 | 40.06 |

Injecting Triton alone (Group II) significantly increased the total cholesterol level to 397.4 mg/dl, whereas in Group V, following oral administration of blend of Amla seed extract (sample 1) and product 1 to triton injected rats, the cholesterol level remained about 91.1 mg/dl even after 24 hours of testing. Therefore, administering Group V resulted in 4.4 times lower level of cholesterol as compared to triton alone treatment (Group II).

In Group II triton injection increased the triglyceride level to 545 mg/dl. Whereas in Group V, oral administration of blend of amla seed extract (sample 1) and product 1 to triton injected rats, the triglyceride level was 64.5 mg/dl, which is 8.5 times lower as compared to triton alone group (Group 2).

In triton alone group after triton injection the ratio of HDL to total cholesterol was 0.11. Whereas in Group V, the ratio of HDL cholesterol to total cholesterol was 0.53, which is 4.8 times higher as compared to triton alone group.

In group II, triton injection increased the LDL level to 246.6 mg/dl. Whereas in Group V, LDL level was 29.7 mg/dl, which is 8.3 times lower as compared to triton alone group.

In group II, triton injection increased the VLDL level to 109 mg/dl. Whereas in Group V, the VLDL level was 12.9 mg/dl, which is 8.5 times lower as compared to triton alone group.

Injecting Triton alone (Group II) significantly increased the total cholesterol level to 397.4 mg/dl. Whereas in Group VI (Triton followed by product 3 administration), cholesterol level was 97 mg/dl, which is 4 times lower as compared to triton alone group.

In Group II Triton injection increased the triglyceride level to 545 mg/dl. Whereas in Group VI, oral administration of product 3 to triton injected rats, triglyceride level was 70 mg/dl, which is 7.7 times lower as compared to triton alone group.

In triton alone group after triton injection the ratio of HDL to total cholesterol was 0.11. Whereas in Group VI, oral administration of amla seed extract (product 3) to triton injected rats, the ratio of HDL cholesterol to total cholesterol was 0.47 which is 4.2 times higher as compared to triton alone group.

In Group II, Triton injection increased the LDL level to 246.6 mg/dl. Whereas in Group VI, oral administration of Product 3 to triton injected rats, LDL level was 37 mg/dl, which is 6.6 times lower as compared to triton alone group.

In Group II, triton injection increased the VLDL level to 109 mg/dl. Whereas in Group VI, oral administration of product 3 to triton injected rats, VLDL level was 14 mg/dl, which is 7.8 times lower as compared to triton alone group (Group II).

In group IX, X, XI and XII, oral administration of water extract of Amla fruit and seed, and methanol extract of amla fruit and seed showed slight activity in reducing total cholesterol, triglyceride, HDL, LDL and VLDL. In comparison to activity in Group V, the activity in group IX to XII was negligible.

Group V, fed with a blend of amla seed extract (sample 1) and product 1 has shown a significantly higher efficacy in comparison to oil part of the seed, that is Group VIII, as well as methanol extract of seed as in Group X.

Example 29

Effect of Amla Seed Extract in Patients with Dyslipidaemia

A total of 50 subjects were divided into two groups of 25 subjects each. Both male and female patients having Triglycerides (TG) greater than 200 mg/dL, LDL cholesterol greater than 130 mg/dL, total cholesterol greater than 200 mg/dL and HDL-C below 40 mg/dL for men and 50 mg/dL for women were selected for the study. Patients were not taking any medication (including herbal product) for management of dyslipidaemia. The subjects were given one 500 mg capsule of Amla seed extract prepared as per example 1 or placebo daily after food for 12 weeks.

Efficacy of the study medication was assessed by serum lipid parameters including triglycerides, total Cholesterol, LDL and VLDL. Other parameters measured were fasting plasma glucose, glycosylated haemoglobin, Apo lipoproteins A1, Apo lipoproteins B, homocysteine, Coenzyme Q10, high sensitivity C-reactive protein (hs-CRP), HMG CoA reductase inhibitory activity and TSH.

TABLE 1

Lipid profile (mg/dl) of subjects treated with Amla seed extract and Placebo.

| Parameters | Amla seed extract | | Placebo | |
|---|---|---|---|---|
| | Baseline | After 12 weeks | Baseline | After 12 weeks |
| Total cholesterol (mg/dl) | 230 | 177 | 224 | 222 |
| Triglycerides (mg/dl) | 261 | 150 | 244 | 245 |
| High Density Lipoproteins (mg/dl) | 43 | 55 | 43 | 42 |
| Low Density Lipoproteins (mg/dl) | 136 | 92 | 132 | 131 |
| Very Low Density Lipoproteins (mg/dl) | 52 | 30 | 49 | 49 |
| Atherogenic index of Plasma | 0.44 | 0.09 | 0.41 | 0.42 |

Twelve weeks treatment with amla seed extract decreased the total cholesterol 23% when compared with baseline value whereas in placebo group the reduction was near to only 1%. In case of triglycerides the reduction was 43% in amla seed extract group whereas in placebo group, reduction in triglycerides was 0.4% only. There was significant increase of 28% in HDL level of amla seed extract group whereas HDL level of placebo group was decreased by 2%. Decrease in LDL was very significant and it was 32% in amla seed extract group whereas in placebo the decrease in LDL was 0.8% only. VLDL was decreased about 42% in amla seed extract group whereas in placebo group there was no difference in VLDL level compared to baseline.

As a marker of plasma atherogenecity Atherogenic index of the plasma (AIP) is used, AIP is the logarithmically transformed ratio of molar concentrations of triglycerides (TGs) to HDL-cholesterol (log (TG/HDL [mmol]). AIP increases in people at higher risk for coronary heart disease and is inversely correlated with LDL particle size.

AIP values of –0.3 to 0.1 are associated with low, 0.1 to 0.24 with medium and above 0.24 with high cardiovascular risk. In present study reduction in AIP is observed from 0.44 to 0.09 in amla seed extract group whereas in placebo group very minor increase in AIP is observed. That is amla seed extract decreased the atherogenic index of plasma by 80% in 12 weeks treatment whereas in placebo group the change in AIP was only 2%.

TABLE 2

Apo lipoprotein A1, Apo lipoprotein B, hs-CRP, Homocysteine, Glycosylated Haemoglobin, TSH, HMGCoA reductase inhibitory activity and CoQ10 of subjects treated with Amla seed extract and Placebo.

| Parameters | Amla Seed extract | | Placebo | |
|---|---|---|---|---|
| | Baseline | After 12 weeks | Baseline | After 12 weeks |
| Apo lipoprotein A1 g/L | 1.05 | 1.32 | 1.01 | 1.02 |
| Apo lipoprotein B g/L | 1.52 | 1.11 | 1.49 | 1.48 |
| Ratio of Apo lipoprotein B to Apo lipoprotein A1 | 1.45 | 0.84 | 1.48 | 1.45 |
| hs-CRP mg/L | 3.83 | 2.56 | 3.95 | 4.0 |
| Homocysteine µmol/L | 23.58 | 15.61 | 21.1 | 20.5 |
| Glycosylated Haemoglobin % | 6.70 | 5.59 | 6.35 | 6.35 |
| TSH µIU/ml | 2.43 | 3.19 | 2.53 | 2.45 |
| HMGCoA reductase inhibitory activity ng/ml | 62.4 | 54.8 | 63.4 | 63.4 |
| CoQ10 ng/ml | 47.3 | 46.9 | 48.7 | 49.6 |

Apo A-1 is a protein that has a specific role in the metabolism of lipids and is the main protein component in HDL, the "good cholesterol". Deficiencies in Apo A-1 correlate with an increased risk of developing Cardio vascular disease (CVD). The reference range of Apo-A1 varies by sex, as follows: Men: Greater than 120 mg/dL (1.2 g/L) and Women: Greater than 140 mg/dL (1.4 g/L). In this study, the Apo A-1 has been increased from 1.05 g/L to 1.32 g/L in amla seed extract group whereas in placebo group there was no change. That is an increase of 26% in Apo A-1 after 12 weeks of treatment with amla seed extract. This indicates the benefits of amla seed extract in reducing the risk of CVD.

Apolipoprotein B (Apo B) is an important component of many lipoproteins that are involved in atherosclerosis and cardiovascular disease. Usually, 85-90 percent of Apo B represents LDL particles. The reference range of Apo B levels in adults is less than 130 mg/dL (1.3 g/L). In this study, the Apo B has been reduced from 1.52 g/L to 1.11 g/L in amla seed extract group whereas in placebo group there was no change. There was a decrease of 27% in Apo B level in amla seed extract group whereas decrease in placebo group was about 1%. This indicates the benefits of amla seed extract in reducing the risk of CVD.

Ratio of the apoB/apoA1 is more effective at predicting heart attack risk, than either the apoB or apoA1 measure alone. The normal values are 0.5 to 1.0. In this study, the ratio of Apo B to Apo A-1 has been decreased from 1.45 g/L to 0.84 g/L in amla seed extract group whereas in placebo group there was no change. That is ratio of Apo B to Apo A-1 was decreased by 42% in amla seed extract group whereas the decrease was only 2% in placebo group. This indicates the benefits of amla seed extract in reducing the risk of CVD.

From the results it was observed that there was a decrease of 33% hs-CRP value of amla seed extract group whereas in placebo group hs-CRP was comparable with baseline value.

Homocysteine is an amino acid and breakdown product of protein metabolism that, when present in high concentrations, has been linked to an increased risk of heart attacks and strokes. Homocysteine levels are typically higher in men than women, and increase with age. Common levels are in range of 10-15 µmol/L in plasma. In our study, the homocysteine level has been reduced from 23.58 to 15.61 µmol/L in amla seed extract group whereas in placebo group, there was no change as compared to baseline value. That is twelve weeks treatment with amla seed extract decreased the homocysteine level 33% when compared with baseline value whereas in placebo group the reduction was only about 2%. This indicates the benefits of amla seed extract in managing cardiovascular health and preventing the risk of stroke, heart attack and other related risks.

HbA1c is a measure of the beta-N-1-deoxy fructosyl component of hemoglobin. Normal levels of glucose produce a normal amount of glycated hemoglobin. Excessive formation of early glycation products may adversely affect several functions of blood vessels, lipid metabolism and prone to develop diabetic complications. HbA1c level below 5.7 percent is considered normal whereas between 5.7 and 6.4 percent signals pre-diabetes. In our study, the level of HbA1c has been reduced from 6.7% to 5.59% in amla seed extract group whereas in placebo group, there was no change in HbA1c level. In case of glycosylated Hb the reduction was 16% in amla seed extract group whereas there was no change in placebo group when compared with the baseline value. This indicates the benefits of amla seed extract in managing the blood sugar level and preventing diabetes.

Thyroid function regulates a wide array of metabolic parameters. Thyroid function significantly affects lipoprotein metabolism as well as some cardiovascular disease (CVD) risk factors, thus influencing overall CVD risk. Thyroid hormones induce the 3-hydroxy-3-methylglutaryl-coenzyme A (HMG-CoA) reductase, which is the first step in cholesterol biosynthesis. Normal TSH level ranges from 0.4 to 4 µIU/ml. In our study, the amla seed extract administration increased the TSH level from 2.43 to 3.19, thus increasing the lipoprotein lipase which reflects in decreasing the TGs. In placebo group there was slight decrease in TSH level. Increase in the TSH level was 31% in amla seed extract group whereas TSH level of placebo group was decreased by 3%.

Coenzyme Q10 is the coenzyme for mitochondrial enzyme complexes involved in oxidative phosphorylation in the production of ATP. A deficiency of CoQ10 in the blood and the heart muscle has been documented in congestive heart failure. Primary and secondary deficiencies of CoQ10 result in a number of neurologic and myopathic syndromes. HMG-CoA reductase (3-hydroxy-3-methyl-glutaryl-coenzyme A reductase) is the rate-controlling enzyme of the mevalonate pathway, the metabolic pathway that produces cholesterol and other isoprenoids. Normally in mammalian cells this enzyme is suppressed by cholesterol derived from the internalization and degradation of low density lipoprotein (LDL) via the LDL receptor as well as oxidized species of cholesterol. In this study, highly significant reduction in HMGCoA reductase enzyme by Amla seed extract explains its mechanism of decreasing blood cholesterol and management of cardio vascular health. At the same time, no change in CoQ10 level puts an advantage of Amla seed extract over statin therapy and makes it better choice than statins for treatment of dyslipidemia.

Decrease in HMGCoA reductase activity was 12% in amla seed extract group and at the same time there was no change in CoQ10 level. There was no change in HMGCoA reductase activity and CoQ10 level in placebo group after 12 weeks of treatment.

TABLE 3

Fasting Plasma Glucose (FPG) mg/dl of subjects treated with Amla seed extract and Placebo.

| Parameters | Amla seed extract | | Placebo | |
|---|---|---|---|---|
| | Baseline | After 12 weeks | Baseline | After 12 weeks |
| Fasting Plasma Glucose mg/dl | 90.6 | 84.4 | 91.9 | 100.4 |

Fasting plasma glucose (FPG) was decreased by 7% after 12 weeks of treatment with amla seed extract whereas there was an increase of 9% in FPG of placebo group compared to baseline value.

Example 30

HMG-CoA Reductase Inhibition Assay of Amla Seed Extract

Amla seed extract prepared as per example 1 and water extract of dried Amla seed prepared as per example 8 was weighed separately and each extract was dissolved in dimethyl sulfoxide (DMSO) to prepare a stock of 400 mg/ml stock solution of each. From this stock, different dose levels were prepared in DMSO for further experimental use.

| Sample | 1× Assay buffer | Inhibitor/test sample | NADPH | HMGCoA | HMG-CoA Reductase (HMGR) |
|---|---|---|---|---|---|
| Blank | 920 µl | — | 20 µl | 60 µl | — |
| Activity | 915 µl | — | 20 µl | 60 µl | 5 µl |
| Inhibition | 910 µl | 5 µl | 20 µl | 60 µl | 5 µl |

The optical density (OD) values were recorded using spectrophotometer at regular time intervals. Specific activity was calculated based on the obtained OD values using the following formula, $$\text{Units/mg } P = \frac{(DA340/\min \text{ sample} - DA340/\min \text{ blank}) \times TV}{12.44 \times V \times 0.6 \times LP}$$

Where:

12.44=εmM—the extinction coefficient for NADPH at 340 nm is 6.22 mM-1 cm-1. 12.44 represents the 2 NADPH consumed in the reaction.

TV=Total volume of the reaction in ml (1 ml for cuvettes and 0.2 ml for plates)

V=volume of enzyme used in the assay (ml)

0.6=Enzyme concentration in mg-protein (mgP)/ml (0.50-0.70 mgP/ml)

LP=Light path in cm (1 cm for cuvettes).

Based on the specific activity values from all the test doses, EC50 (Effective Concentration 50) were determined by plotting a curve between Specific activity Vs. Test concentration. EC50 values (µg/ml) and IC50 (µM) were determined by interpolation method by using Graph pad prism, version 5.01.

TABLE 1

| HMGR inhibitory activity of Amla seed extract. | | | | |
|---|---|---|---|---|
| Test | % Inhibition over control | | Test | % Inhibition over control |
| concentration (μg/ml) | Amla Seed extract | Water extract of dried amla seed | concentration (μM) | LOVASTATIN |
| 200 | 98.51 | 66.57 | 100 | 98.51 |
| 100 | 91.49 | 49.37 | 80 | 86.56 |
| 50 | 47.13 | 35.92 | 60 | 76.55 |
| 25 | 41.75 | 8.29 | 40 | 55.64 |
|  |  |  | 20 | 41.45 |
|  |  |  | 10 | 37.72 |
|  |  |  | 5 | 37.57 |
|  |  |  | 2.5 | 36.97 |
| IC50 | 31.07 | 142.6 |  | 29.7 |

The IC50 value for amla seed extract was about 31 μM which was almost equivalent to the IC50 value (29.7 μM) of standard lovastatin. This indicates that amla seed extract has almost similar percentage inhibition of HMG CoA reductase as lovastatin. Water extract of dried amla seed was less effective and IC50 value was noted as 142.6 μM.

Example 31

Triterpenoid.Hydroxycinnamic Acid and Fatty Acid Ratios in Amla Seed Extracts

TABLE 1

| Ratios of components in Amla seed extracts | | | | | | |
|---|---|---|---|---|---|---|
| | | percentage | | | | |
| | | Triterpenoids (T) | Hydroxycinnamic acid (H) | Fatty acids (F) | Ratio T:H:F | |
| Amla seed powder | Percentage | 0.06% | 0.3% | 2% | 1:5:33 | |
| EA extract of methanol extract of Amla seed [Example 1] | Percentage | 9.5% | 4.3% | 41.8% | 2:1:10 | |
| product 1 (Example 13) | Percentage |  |  | 77.5% |  | |
| product 2 (Example 13) | Percentage | 50% | 29.3% |  |  | |
| product 3 = Product 1 blended with Product 2 in 3:2 ratio. [Example 13] | Percentage | 20% | 11.7% | 46.5% | 2:1:4 | |
| Sample 1 [Example 27] | Percentage | 63.5% | 27% |  |  | |
| (Sample 2) Amla seed extract enriched with triterpenoids i.e. Sample 1 blended with Product 1 in 1:1 ratio [Example 27] | Percentage | 32% | 13.5% | 38.6% | 2:1:3 | |

In amla seed powder, triterpenoids was about 0.06%, hydroxycinnamic acid was about 0.3% and fatty acid was about 2%. Based on this, in amla seed powder, the ratio of triterpenoids to hydroxycinnamic acid to fatty acid was about 1:5:33. Fatty acid content was higher in the amla seed powder compared to triterpenoids and hydroxycinnamic acid.

In the present product 3 (from Example 13), which was prepared by blending two extracts (product 1 from Example 13 and product 2 from Example 13 in a ratio of 3:2), triterpenoids and hydroxycinnamic acid were significantly enriched compared to fatty acids. The ratio of triterpenoids to hydroxycinnamic acid to fatty acids in Product 3 was about 2:1:4, which is clearly different from the ratio found for amla seed powder.

In amla seed blend composition (sample 2 from Example 27), the ratio of triterpenoids to hydroxycinnamic acid to fatty acid was 2:1:3, which is very different from the ratio obtained in amla seed powder.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

I claim:

1. A method of lowering HMGCoA reductase in a subject in need thereof, the method comprising administering a blend of extracts of seeds of *Emblica officinalis*, the blend comprising a first extract of seeds of *Emblica officinalis* and a second extract of seeds of *Emblica officinalis*, the first extract comprising:
   a) about 20% to about 70% triterpenoids; and,
   b) about 10% to about 40% hydroxycinnamic acids, and, the second extract of seeds of *Emblica officinalis* comprising alpha linolenic acid, linoleic acid and oleic acid, wherein a weight ratio of the first extract of *Emblica Officinalis* to the second extract of *Emblica officinalis* in the blend ranges from about 1:60 to about 99:1.

2. A method of lowering HMGCoA reductase in a subject in need thereof, the method comprising administering an extract of seeds of *Emblica officinalis*, the extract comprising:

about 0.5% to about 20% triterpenoids,
about 0.5% to about 5% of hydroxycinnamic acids, and,
about 25% to about 50% fatty acids.

* * * * *